United States Patent
Gleason et al.

(10) Patent No.: US 9,428,447 B2
(45) Date of Patent: Aug. 30, 2016

(54) BIS-(ARYL/HETEROARYL)-METHYLENE COMPOUNDS, PHARMACEUTICAL COMPOSITIONS CONTAINING SAME AND THEIR USE FOR TREATING CANCER

(71) Applicant: The Royal Institution For The Advancement of Learning/McGill University, Montréal (CA)

(72) Inventors: James L. Gleason, Westmount (CA); John H. White, Town of Mount Royal (CA); Dainis Kaldre, Montréal (CA); Joshua Fischer, Wollstonecraft (AU)

(73) Assignee: The Royal Institution for the Advancement of Learning/McGill University, Montreal, Quebec (CA)

( * ) Notice: Subject to any disclaimer, the term of this patent is extended or adjusted under 35 U.S.C. 154(b) by 109 days.

(21) Appl. No.: 14/367,375

(22) PCT Filed: Dec. 20, 2012

(86) PCT No.: PCT/CA2012/001188
§ 371 (c)(1),
(2) Date: Jun. 20, 2014

(87) PCT Pub. No.: WO2013/091082
PCT Pub. Date: Jun. 27, 2013

(65) Prior Publication Data
US 2014/0315965 A1 Oct. 23, 2014

Related U.S. Application Data

(60) Provisional application No. 61/578,471, filed on Dec. 21, 2011.

(51) Int. Cl.
| | | |
|---|---|---|
| *A61K 31/42* | (2006.01) | |
| *C07C 259/06* | (2006.01) | |
| *C07D 263/32* | (2006.01) | |
| *C07D 209/18* | (2006.01) | |
| *C07D 333/16* | (2006.01) | |
| *C07D 333/24* | (2006.01) | |
| *C07D 209/12* | (2006.01) | |

(52) U.S. Cl.
CPC .......... *C07C 259/06* (2013.01); *C07D 209/12* (2013.01); *C07D 209/18* (2013.01); *C07D 263/32* (2013.01); *C07D 333/16* (2013.01); *C07D 333/24* (2013.01)

(58) Field of Classification Search
CPC C07C 259/06; C07D 209/12; C07D 209/18; C07D 333/24; C07D 333/16; C07D 263/32
USPC .............. 514/374, 575, 415, 438; 549/77; 548/503, 236; 562/621
See application file for complete search history.

(56) References Cited

U.S. PATENT DOCUMENTS

| | | |
|---|---|---|
| 7,601,850 B2 | 10/2009 | Dahnke et al. |
| 7,750,184 B2 | 7/2010 | Gajewski et al. |
| 2006/0135484 A1 | 6/2006 | Nagpal et al. |

FOREIGN PATENT DOCUMENTS

| | | |
|---|---|---|
| WO | 00/63197 A1 | 10/2000 |
| WO | 2006/069153 A2 | 6/2006 |

OTHER PUBLICATIONS

Kashiwagi et al (Bioorganic & Medicinal Chemistry, 2011, 19, 4721-4729).*

Akutsu, N. et al. "Regulation of Gene Expression by 1x,25-Dihdroxyvitamin D3 and its Analog EB1089 Under Growth-Inhhibitory Conditions in Squamous Carcinoma Cells", Molecular Endocrinology, vol. 15, 2001, pp. 1127-1139.

Banwell, C.M. et al."Targeting 1x,25-Dihydroxyvitamin D3 Antiproliferative Insesitivity in Breast Cancer Cells by Co-Treatment With Histone Deacetylation Inhibitors", J Steriod Biochem Mol. 2004, pp. 89-90: 245-249.

Boehm, Marcus F. et al., "Novel Nonsecosteroidal Vitamin D Mimics Exert VDR-Moduling Activities With Less Calcium Mobilization Than 1,25-Dihdroxyvitamin D3" Chemistry & Biology. vol. 6, No. 5. 1999. pp. 265-275.

Bouillon, Roger, et al., "Structure-Function Relationship in the Vitamin D Endocrine System", Endocrine Reviews. vol. 16, No. 2, 1995. pp. 200-257.

Fischer, J. et al., "Synthetically Accessible Non-Secosteriod Hybrid Molecules Combing Vitamin D Receptor Agonism and Histone Deacetylase Inhibition", Chemistry & Biology, Vo. 19, Aug. 24, 2012, pp. 963-971.

Gleason, James L. "Development of Novel Hybrid VDR Agonist/ HDAC Inhibitors for Cancer Treatment", Calgary, May 28, 2012.

(Continued)

*Primary Examiner* — Jason Sims
*Assistant Examiner* — Ibrahim D Bori
(74) *Attorney, Agent, or Firm* — Buchanan Ingersoll & Rooney P.C.

(57) ABSTRACT

The present disclosure relates to novel compounds having vitamin D receptor agonist and histone deacetylase inhibitory efficacy as well as methods for reducing or inhibiting the proliferation of cancer cells or for treating cancer.

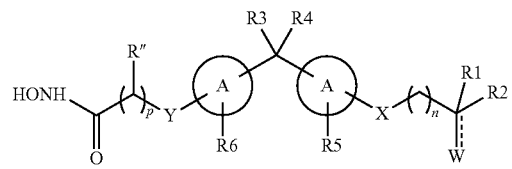

18 Claims, 22 Drawing Sheets

(56) References Cited

OTHER PUBLICATIONS

Gleason, James L., "Hybridizing Natural Products for Cancer Treatment". FloHet, Mar. 6, 2012.
Gleason, James L. "Hybridization for HDACI for Improved Therapies". Boston, Oct. 1, 2012.
Gleason, James L. et al., Hybridizing Chemical Agents for Cancer Treatment. Keystone, Mar. 20, 2012 (Poster).
Jones, Glenville et al. "Current Understanding of the Molecular Actions of Vitamin D". Physiological Reviews, vol. 78, No. 1998, pp. 1193-1231.
Jones, Glenville, "Vitamin D Analogs", Endocrinol Metab Clin N Am. vol. 39, 2010, pp. 447-472.
Khanim, F.L. et al."Altered SMRT Levels Disrupt Vitamin D3 Receptor Signalling in Prostate Cancer Cells" Oncogene, vol. 23, 2004, pp. 6712-6725.
Lamblin, M. et al."Vitamin D Receptor Agonist/Histone Deacetylase Inhibitor Molecular Hybrids" Bioorganic & Medicinal Chemistry, vol. 18, 2010, pp. 4119-4137.
Lin, R. et al. "Expression Profiling in Squamous Carcinoma Cells Reveals Pleiotropic Effects of Vitamin D3 Analog EB1089 Signaling on Cell Proliferation, Differentiation, and Immune System Regulation" Molecular Endocrinology, vol. 16, 2002, pp. 1243-1256.
Ma, Yanfei et al. "Indentification and Characterization of Noncalcemic, Tissue-Selective, Nonsecosteroidal Vitamin D Receptor Modulators", The Journal of Clinical Investigation, vol. 116, No. 4, 2006, pp. 892-904.
Perakyla, Mikael et al. "Gene Regulatory Potential of Nonsteroidal Vitamin D Receptor Ligands" Mol. Endocrinol, 19(8), 2005, pp. 2060-2073.
Prodencio, J. et al. "Action of Low Calcemic 1x,25-Dihydroxyvitamin D3 Analoge EB1089 in Head and Neck Squamous Cell Carcinoma" Journal of the national Cancer Institute, vol. 93, 2001, pp. 745-753.
Swann, Steve L. et al. "Structure-Based Design of Slective Agonists for a Rickets-Associated Mutant of the Vitamin D Receptor", J. Am. Chem. Soc. vol. 124, 2002, pp. 13795-13805.
Tavera-Mendoza, L.E. et al. "Incorporated of Histone Deacetylase Inhibition Into the Structure of a Nuclear Receptor Agonist" Proceedings of the National Academy of Sciences of the United States of America. vol. 105, 2008, pp. 8250-8255.
Wang, T.T. et al. Cutting Edge: 1,25-Dihydroxyvitamin D3 is a Direct Inducer of Antimicrobial Peptide Gene Expression: J. Immunol, vol. 173, 2004, pp. 2909-2912.

* cited by examiner

BIS-(ARYL/HETEROARYL)-METHYLENE COMPOUNDS, PHARMACEUTICAL COMPOSITIONS CONTAINING SAME AND THEIR USE FOR TREATING CANCER

FIELD OF THE DISCLOSURE

The present disclosure relates to novel compounds having vitamin D receptor agonist and histone deacetylase inhibitory efficacy as well as methods for reducing or inhibiting the proliferation of cancer cells or for treating cancer.

BACKGROUND OF THE DISCLOSURE

The active form of vitamin D, 1,25-dihydroxyvitamin D (1,25D), has attracted broad interest because of its anticancer properties. However, 1,25D and several analogues have failed as therapies because of poor efficacy or acquired resistance. Preclinical studies in cancer revealed combinatorial effects of combining 1,25D analogues with histone deacetylase inhibitors (HDACi). Hormonal 1,25D activates the vitamin D receptor (VDR), which functions as a ligand-regulated transcription factor.

The capacity of 1,25D, and its analogues, to inhibit proliferation of head and neck squamous carcinoma cells (HNSCC) has been studied (see Lin, R. et al. *Molecular Endocrinology* (2002) 16:1243-1256; Akutsu, N. et al. *Molecular Endocrinology* (2001) 15:1127-1139; Prudencio, J. et al *Journal of the National Cancer Institute* (2001) 93:745-753). Whereas proliferation of well-differentiated human SCC25 cells is arrested in G0/G1, poorly differentiated SCC4 cells are 1,25D-resistant. However, this resistance can be overcome by coadministration of the histone deacetylase inhibitor (HDACi) trichostatin A (TSA). Indeed, SCC4 cells are particularly sensitive to the combination of 1,25D and TSA, consistent with combinatory effects on prostate and breast cancer cell proliferation and survival (see Khanim, F. L. et al *Oncogene* (2004) 23:6712-6725 and Banwell, C. M. et al *J Steroid Biochem Mol Biol* (2004) 89-90:245-249. Nuclear HDACs can modulate gene transcription by controlling DNA-histone interactions in the nucleosome and through regulation of components of the transcription machinery. HDACi's, such as trichostatin A (TSA) and suberoylanilide hydroxamic acid (SAHA), have been investigated as anti-cancer agents and, similar to VDR agonists, HDACi's induce cell cycle arrest, cellular differentiation and/or apoptosis.

Triciferol, has a merged the secosteroidal backbone with a side chain derived from TSA and has shown both a VDR agonist and an HDACi in cells in culture, and was more efficacious in vitro than 1,25D in inhibition of SCC4 cell proliferation (see Tavera-Mendoza, L. E., et al. *Proceedings of the National Academy of Sciences of the United States of America* (2008) 105:8250-8255).

SUMMARY

In an aspect of the disclosure, there is provided a compound represented by formula

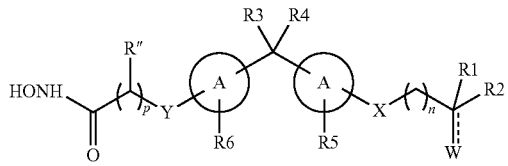

or a pharmaceutically acceptable salt thereof, wherein
the dotted line is an optional double bond;
A and B are each independently an aryl or heteroaryl;
R1 is hydrogen, an alkyl or cycloalkyl;
R2 is absent when the dotted line is a double bond or R2 is hydrogen, an alkyl or cycloalkyl when the dotted line is absent;
W is OH when the dotted line is absent or W is O when the dotted line is a double bond;
X is O, $CH_2$, CHR7 or CR7R7, where R7 is in an alkyl or fluoroalkyl;
Y is NR10(CO), (CO)NR10, O, $CH_2$, CHR7 or CR7R7, where R7 is in an alkyl or fluoroalkyl and R10 is H or an alkyl;
R3 and R4 are each independently hydrogen, an alkyl or fluoroalkyl;
R5 and R6 are each independently an optional substituent;
when p is greater than 0, R" is H and one of said R" is optionally OH;
n and p are each an integer from 0 to 6.

In yet another aspect of the disclosure, there is provided a method, use or composition for treating or preventing cancer comprising administering an effective amount of at least one compounds as defined herein.

In yet another aspect of the disclosure, there is provided a pharmaceutical composition comprising a compound as defined herein or a pharmaceutically acceptable salt thereof, and an acceptable excipient.

In yet another aspect of the disclosure, there is provided a method, use or composition for inhibiting a histone deacetylase (HDAC).

In yet another aspect of the disclosure, there is provided a method, use or composition for reducing or stopping the proliferation of cancer cells.

DESCRIPTION OF THE EMBODIMENTS

Figure 1A:
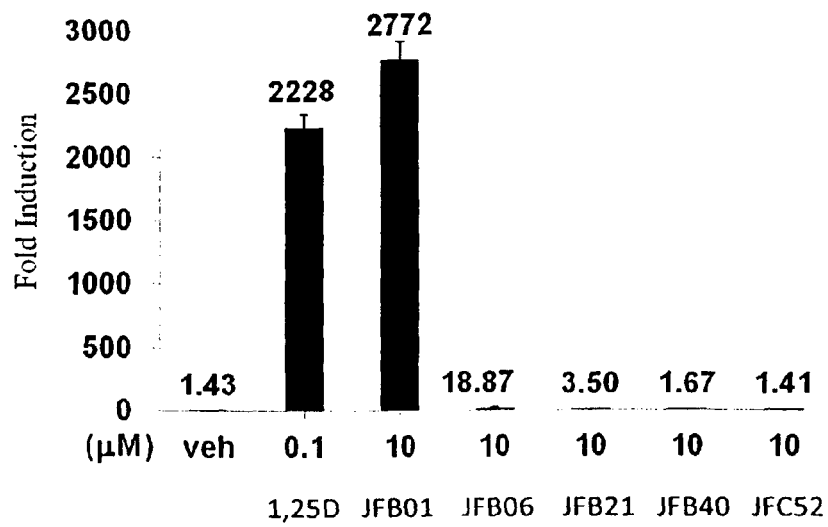
FIG. 1*a*-1*d* is a representation of the activity in a VDR agonism model by analysis of induction of CYP24 gene expression in 1,25D-sensitive human SCC25 cells.

In one embodiment, there is provided a compound represented by formula A compounds of formula

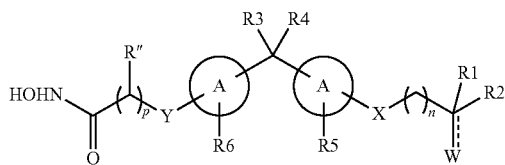

or a pharmaceutically acceptable salt thereof, wherein
the dotted line is an optional double bond;
A and B are each independently an aryl or heteroaryl;
R1 is hydrogen, an alkyl or cycloalkyl;
R2 is absent when the dotted line is a double bond or R2 is hydrogen, an alkyl or cycloalkyl when the
dotted line is absent;
W is OH when the dotted line is absent or W is O when the dotted line is a double bond;
X and Y are each independently is O, $CH_2$, CHR7 or CR7R7, where R7 is an alkyl or fluoroalkyl;
R3 and R4 are each independently hydrogen, an alkyl or fluoroalkyl;
R5 and R6 are each independently an optional substituent;
n and p are each an integer from 1 to 5.

In one embodiment, A and B are each independently a phenyl and a 5-6 membered heteroaryl.

In one embodiment, A and B are both a phenyl.

In one embodiment, A and B are both a 5-6 membered heteroaryl.

In one embodiment, A is a phenyl and B is a 5-6 membered heteroaryl.

In one embodiment, A is a phenyl and B is a 5 membered heteroaryl.

In one embodiment, A is a phenyl and B is a 6 membered heteroaryl.

In one embodiment, A is a 5-6 membered heteroaryl and B is a phenyl.

In one embodiment, A is a 5 membered heteroaryl and B is a phenyl.

In one embodiment, A is a 6 membered heteroaryl and B is a phenyl.

In one embodiment, A and B are both a 8 to 10 membered bicyclic heteroaryl.

In one embodiment, A is a phenyl and B is 8 to 10 membered bicyclic heteroaryl.

In one embodiment, A is a 8 to 10 membered bicyclic heteroaryl and B is a phenyl.

In one embodiment, the compound has the formula:

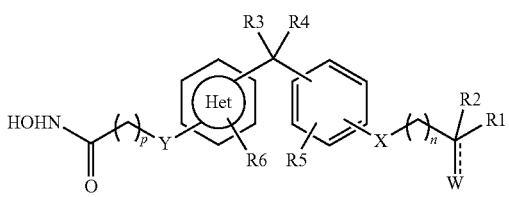

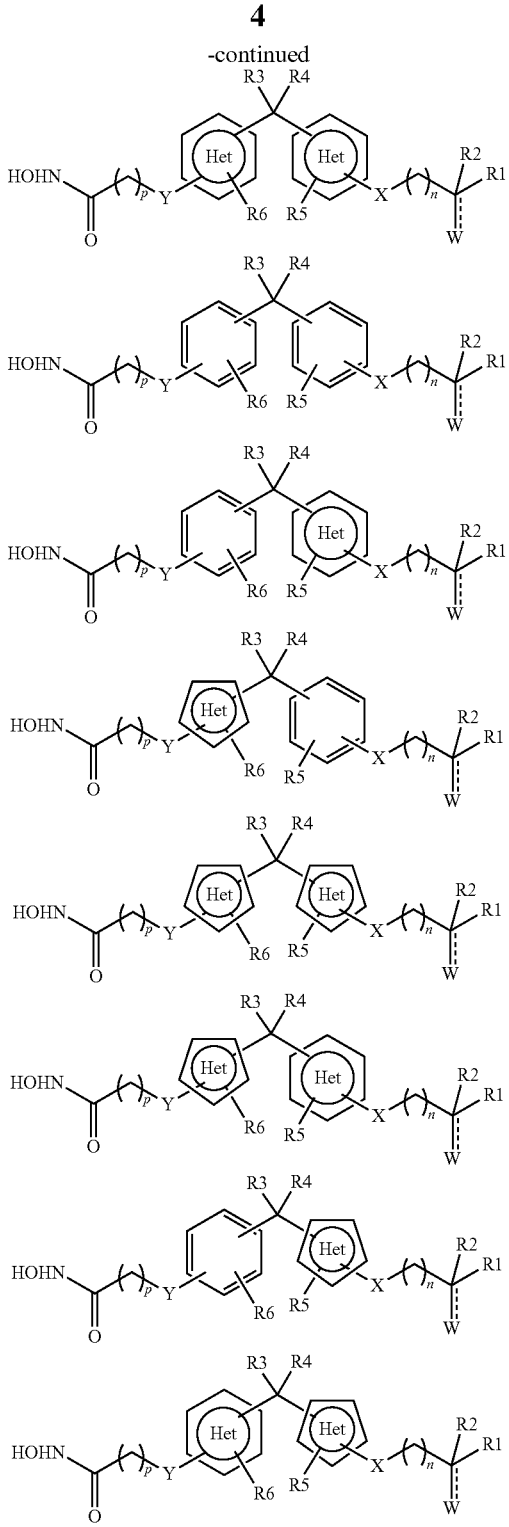

wherein the symbol

with the 5-6 membered ring represents a 5-6 membered heteroaryl.

In one embodiment, the compound has the formula:

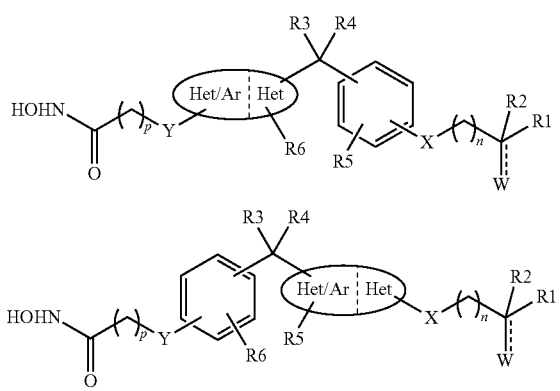

wherein the symbol

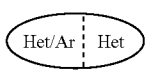

means a fused bicyclic heteroraryl wherein Het/Ar means an heteroaryl or aryl ring and Het is a heteroaryl ring. X, Y, R5 and R6 as well as the carbon bearing R3 and R4 can be independently attached to the Het/Ar or Het portion of the heteroaryl.

In one embodiment, when A and/or B represent a phenyl, one or both of the residues connected through X and Y are in a para relationship to the phenyl carbon substituted by CR3R4.

In one embodiment, when A and/or B represent a heteroaryl, the residues connected through X and Y and the carbon substituted by CR3R4 are attached to a carbon atom of said heteroaryl.

In one embodiment, when A and/or B represent a 5-membered ring heteroaryl, one or both of the residues connected through X and Y are in a 1-3 relationship to the heteroaryl carbon substituted by CR3R4:

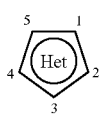

In one embodiment, when A and/or B represent a 6-membered ring heteroaryl, one or both of the residues connected through X and Y are in a 1-4 relationship to the heteroaryl carbon substituted by CR3R4:

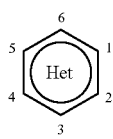

In one embodiment, the compound has the formula:

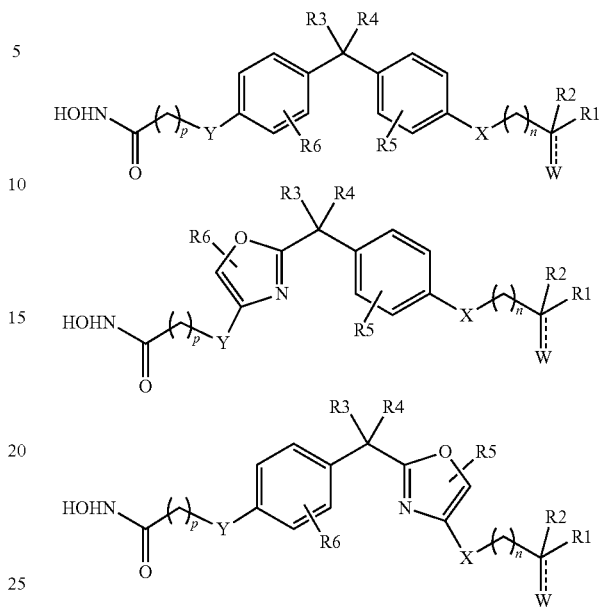

In one embodiment, in the compounds described herein X and Y are both O.

In one embodiment, in the compounds described herein X and Y are both $CH_2$.

In one embodiment, in the compounds described herein X is O and Y is $CH_2$.

In one embodiment, in the compounds described herein X is $CH_2$ and Y is O.

In one embodiment, in the compounds described herein, X is O and Y is O or NR10(CO).

In one embodiment, in the compounds described herein dotted line is absent and W is OH.

In one embodiment, in the compounds described herein dotted line is a double bond and W is O.

In one embodiment, in the compounds described herein R1 is an alkyl or cycloalkyl and R2 is hydrogen, an alkyl or cycloalkyl.

In one embodiment, in the compounds described herein R1 is an alkyl and R2 is hydrogen or an alkyl.

In one embodiment, in the compounds described herein R1 is an alkyl and R2 is hydrogen.

In one embodiment, in the compounds described herein R1 is a C1-4 alkyl and R2 is hydrogen.

In one embodiment, in the compounds described herein R1 and R2 are each independently an alkyl.

In one embodiment, in the compounds described herein R1 and R2 are each independently a C1-4 alkyl.

In one embodiment, in the compounds described herein R1 and R2 are each independently a C1-2 linear alkyl.

In one embodiment, in the compounds described herein R1 and R2 are each independently a C3-4 branched alkyl.

In one embodiment, in the compounds described herein R3 and R4 are independently hydrogen, an alkyl or fluoroalkyl.

In one embodiment, in the compounds described herein R3 and R4 are the same and are both hydrogen, an alkyl or fluoroalkyl.

In one embodiment, in the compounds described herein R3 and R4 are both hydrogen.

In one embodiment, in the compounds described herein R3 and R4 are both an alkyl.

In one embodiment, in the compounds described herein R3 and R4 are both fluoroalkyl.

In one embodiment, in the compounds described herein R3 and R4 are both a C1-4alkyl.

In one embodiment, in the compounds described herein R3 and R4 are both a C1-4fluoroalkyl.

In one embodiment, in the compounds described herein R3 and R4 are each independently a methyl, ethyl or propyl.

In one embodiment, in the compounds described herein R3 and R4 are the same and are a methyl, ethyl or propyl.

In one embodiment, in the compounds described herein the total of n and p is 2-6.

In one embodiment, in the compounds described herein the total of n and p is 2-4.

In further embodiments, in the compounds described herein:
n=1 and p is 1-3; n=1 and p is 1-2; n=1 and p is 1; n=1 and p is 2; n=1 and p is 3; p=1 and n is 1- 3; p=1 and n is 1-2; p=1 and n is 1; p=1 and n is 2 or p=1 and n is 3.

In one embodiment, R5 and R6 are each independently an alkyl or cycloalkyl; preferably an alkyl, preferably a C1-3 alkyl.

In one embodiment, in the compounds described herein, the formula is

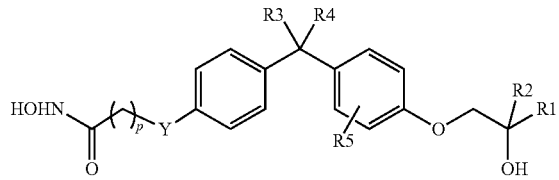

wherein R1, R2, R3 and R4 are each independently a C1-4 alkyl; R5 is a C1-3 alkyl and p is 1-5.

In one embodiment, in the compounds described herein, the formula is

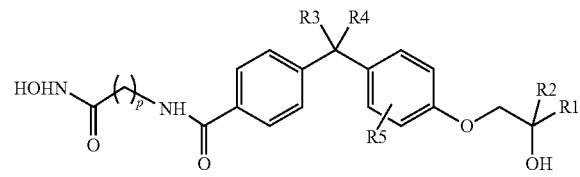

wherein R1, R2, R3 and R4 are each independently a C1-4 alkyl; R5 is a C1-3 alkyl and p is 1-5.

The term "alkyl" represents a linear or branched moiety. Examples of "alkyl" groups include but are not limited to methyl, ethyl, propyl, isopropyl, butyl, isobutyl, sec-butyl, tert-butyl, pentyl, isopentyl, neopentyl, tert-pentyl, hexyl, isohexyl or neohexyl. The term "alkyl" is also meant to include alkyls in which one or more hydrogen atoms are replaced by a halogen, ie. an alkylhalide. In this application, fluoroalkyls are also particularly contemplated as alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl.

The term "cycloalkyl" represents a carbocyclic moiety having 3 to 7 members, preferably 3-6. Examples of "cycloalkyl" groups include but are not limited to cyclopropyl, cyclobutyl, cyclopentyl, cyclohexyl and cycloheptyl.

The terms "alkoxy," and "cycloalkoxy" represent an alkyl, cycloalkyl, moiety, respectively, which is covalently bonded to the adjacent atom through an oxygen atom. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy, neohexyloxy, cyclopropyloxy, cyclobutyloxy, cyclopentyloxy, cyclohexyloxy.

As used herein, amino include amino which are unsubstituted such as —NH$_2$, or substituted with one or two C1-6alkyl or aryl such as —NH(C$_{1-6}$alkyl), —N(C$_{1-6}$alkyl)$_2$, —N(C$_{1-6}$alkyl)(aryl) and —N (aryl)$_2$.

The term "aryl" represents a carbocyclic moiety containing at least one benzenoid-type ring (i.e., may be monocyclic or polycyclic), Examples include but are not limited to phenyl, tolyl, dimethylphenyl, aminophenyl, anilinyl, naphthyl, anthryl, phenanthryl or biphenyl.

The term "aryloxy" represents an aryl moiety, which is covalently bonded to the adjacent atom through an oxygen atom. Examples include but are not limited to phenoxy, dimethylphenoxy, aminophenoxy, anilinoxy, naphthoxy, anthroxy, phenanthroxy or biphenoxy.

The term "arylalkyl" represents an aryl group attached to the adjacent atom by an alkyl, alkenyl or alkynyl. Examples include but are not limited to benzyl, benzhydryl, trityl, phenethyl, 3-phenylpropyl, 2-phenylpropyl, 4-phenylbutyl and naphthylmethyl.

The term "arylalkyloxy" represents an arylalkyl moiety, which is covalently bonded to the adjacent atom through an oxygen atom. Examples include but are not limited to benzyloxy, benzhydroxy, trityloxy, phenethyloxy, 3-phenylpropoxy, 2-phenylpropoxy, 4-phenylbutoxy and naphthylmethoxy.

The term "heteroaryl" represents a 5 or 6 membered optionally substituted, aromatic cyclic moiety wherein said cyclic moiety is interrupted by at least one heteroatom selected from oxygen (O), sulfur (S) or nitrogen (N). Examples of heteroaryls include but are not limited to, furanyl, isoxazolyl, isothiazolyl, imidazolyl, oxadiazolyl, oxazolyl, pyrazinyl, pyridazinyl, pyrimidinyl, pyridinyl, pyrazolyl, pyrrolyl, tetrazolyl, triazolyl, thiazolyl, thienyl, triazinyl, and thiazinyl.

The term "heteroaryl" also represents a fused bicyclic 8 to 10 membered heteroaryl, optionally substituted. Examples of bicyclic heteroaryl include but are not limited to furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, indolyl, furopyrimidinyl, furopyridyl, benzofuranyl, isobenzofuranyl, thienopyrimidinyl, thienopyridyl, benzothienyl, benzoxazinyl, benzothiazinyl, quinazolinyl, naphthyridinyl, quinolinyl, isoquinolinyl, benzopyranyl, pyridopyridazinyl and pyridopyrimidinyl.

When the heteroaryl moeity is a bicyclic ring, the rings comprise at least one ring comprising the heteroatom and the other rings may be acyl or heteroaryl and the point of attachment may be on any available atom.

"Halogen atom" is specifically a fluorine atom, chlorine atom, bromine atom or iodine atom.

The terms "optionally substituted" or "optional substituent" represent at each occurrence and independently, one or more halogen, amino, amidino, amido, azido, cyano, guanido, hydroxyl, nitro, nitroso, urea, OS(O)$_2$Rm (wherein Rm is selected from C1-6alkyl, C6-10aryl or 3-10 membered heterocycle), OS(O)$_2$ORn (wherein Rn is selected from H, C1-6alkyl, C6-10aryl or 3-10 membered heterocycle), S(O)$_2$ORp (wherein Rp is selected from H, C1-6alkyl, C6-10aryl and 3-10 membered heterocycle), S(O)$_{0-2}$Rq (wherein Rq is selected from H, C1-6alkyl, C6-10aryl or 3-10 membered heterocycle), OP(O)ORsORt, P(O)ORsORt (wherein Rs and Rt are each independently selected from H or C1-6alkyl), C1-6alkyl, hydroxyC1-6alkyl, C1-6heteroalkyl, C3-7cycloalkyl, C3-7cycloalkenyl, C6-10aryl-C1-6alkyl, C6-10aryl, C1-6alkoxy, C3-7cycloalkyloxy, C3-7cycloalkenyloxy, C6-10aryl-C1-6alkyloxy, C6-10aryloxy, 3-10 membered heterocycle, C(O)Ru (wherein Ru is selected from H, C1-6alkyl, C6-10aryl, C6-10aryl-C1-6alkyl or 3-10 membered heterocycle), C(O)ORv (wherein Rv is selected from H, C1-6alkyl, C6-10aryl, C6-10aryl-C1-6alkyl or 3-10 membered heterocycle), NRx-C(O)Rw (wherein Rx is H or C1-6alkyl and Rw is selected from H, C1-6alkyl, C6-10aryl, C6-10aryl-C1-6alkyl or 3-10 membered heterocycle, or Rx and Rw are taken together with the atoms to which they are attached to form a 3 to 10 membered heterocycle) or SO$_2$NRyRz (wherein Ry and Rz are each independently selected from H, C1-6alkyl, C6-10aryl, C3-10heterocycle or C6-10aryl-C1-6alkyl). In another embodiment, the term "optionally substituted" represents halogen, C1-6alkyl, C1-6heteroalkyl, C2-6alkenyl, C2-6alkynyl, C3-7cycloalkyl, C3-7cycloalkenyl, C6-10aryl-C1-6alkyl, C6-10aryl, C1-6 alkoxy, C2-6alkenyloxy, C2-6alkynyloxy, C3-7cycloalkyloxy, C3-7cycloalkenyloxy, C6-10aryl-C1-6alkyloxy, C6-10aryloxy, —NR4OR41, —C(O)NR40R41, —NR40COR41, carboxy, azido, cyano, hydroxyl, nitro, nitroso, —OR40, —SR40, —S(O)$_{0-2}$R40, —C(O)R40, —C(O)OR40 and —SO$_2$NR4OR41; wherein R40 and R41 are each independently H, halogen, C1-6alkyl, C2-6alkenyl or C2-6alkynyl.

The terms "alkyl", "cycloalkyl", "alkoxy", "cycloalkoxy", "aryl", "aryloxy", "arylalkyl", "arylalkyloxy", and "heterocycle" defined herein may be, when compatible, further substituted in accordance with the definition above.

The term "independently" means that a substituent can be the same or a different definition for each item.

When there is a sulfur atom present, the sulfur atom can be at different oxidation levels, ie. S, SO, or SO$_2$. All such oxidation levels are within the scope of the present invention.

When there is a nitrogen atom present, the nitrogen atom can be at different oxidation levels, i.e. N or NO. All such oxidation levels are within the scope of the present invention.

The excipient(s) must be "pharmaceutically acceptable" in the sense of being compatible with the other ingredients of the formulation and not being deleterious to the recipient thereof.

In one embodiment, there is provided compounds as illustrated in the following table.

| Compound | |
|---|---|
| (JF-B59) |  |
| (JF-B01) |  |
| (JF-C71) |  |
| (JF-C72) |  |

| Compound | |
|---|---|
| (JF-B53) | 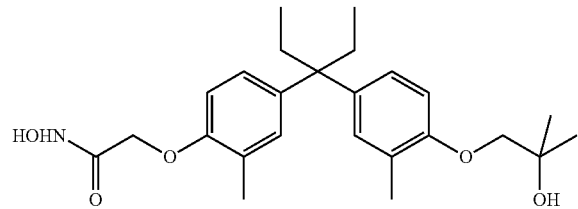 |
| (JF-B54) | 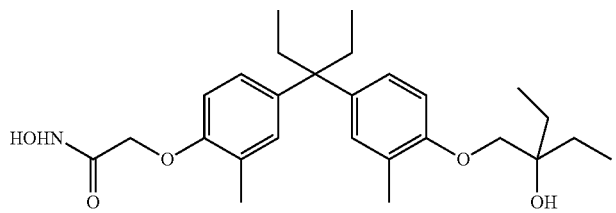 |
| (DK-65) | 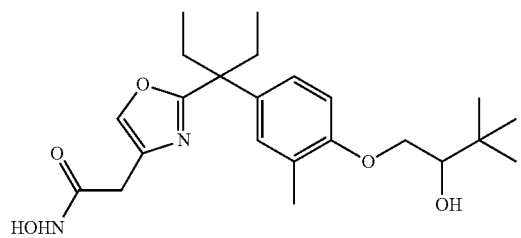 |
| (DK-71) | 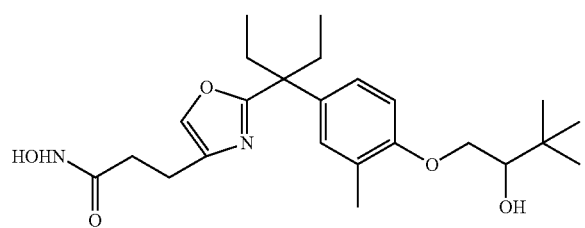 |
| (DK-90) | 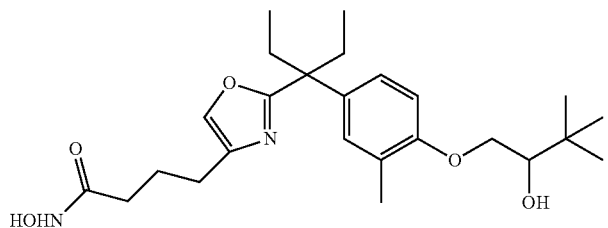 |
| (DK-91) | 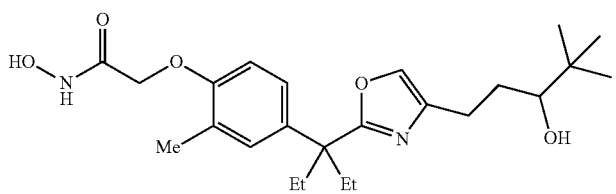 [SMILES: CCC(CC)(c1ccc(OCC(=O)NO)c(C)c1)c1nc(CCC(O)C(C)(C)C)co1] |
| (JFD-15) | 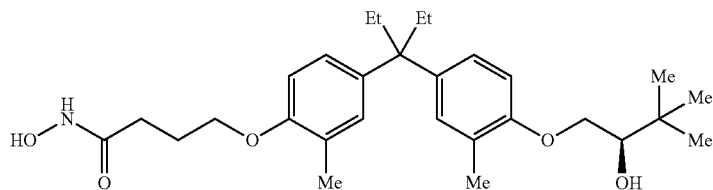 [SMILES: CCC(CC)(c1ccc(OCCCC(=O)NO)c(C)c1)c1ccc(OC[C@H](O)C(C)(C)C)c(C)c1] |

-continued
| Compound | |
|---|---|
| (JFD-50) | 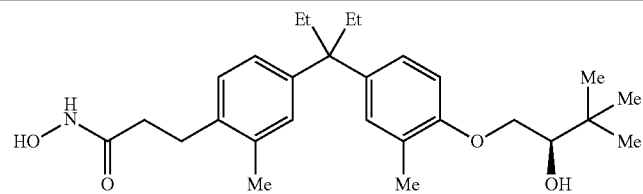 [SMILES: CCC(CC)(c1ccc(CCC(=O)NO)c(C)c1)c1ccc(OC[C@H](O)C(C)(C)C)c(C)c1] |
| (DK-178) | 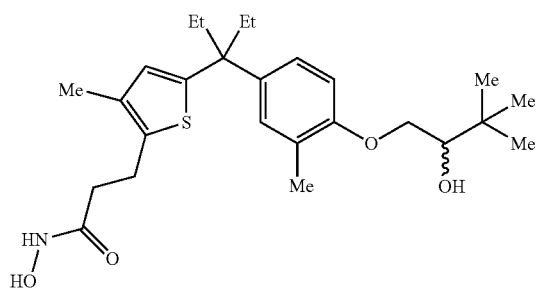 [SMILES: CCC(CC)(c1ccc(OCC(O)C(C)(C)C)c(C)c1)c1cc(C)c(CCC(=O)NO)s1] |
| (DK-201) | 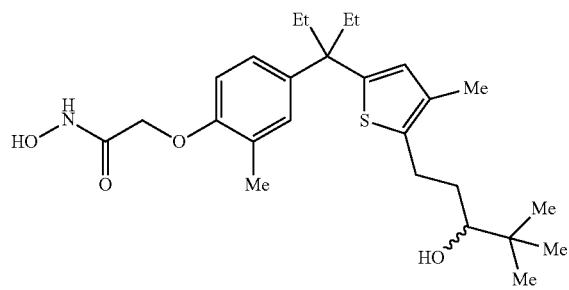 [SMILES: CCC(CC)(c1ccc(OCC(=O)NO)c(C)c1)c1cc(C)c(CCC(O)C(C)(C)C)s1] |
| (DK-222) | 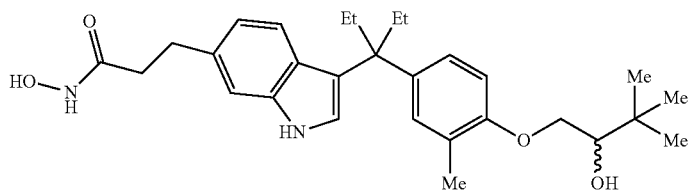 [SMILES: CCC(CC)(c1ccc(OCC(O)C(C)(C)C)c(C)c1)c1c[nH]c2cc(CCC(=O)NO)ccc12] |
| (DK-234) | 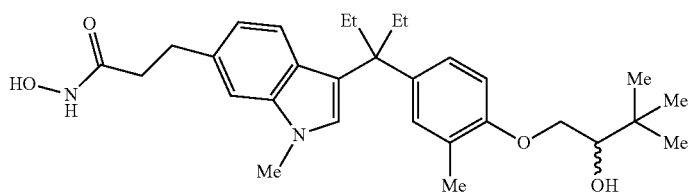 [SMILES: CCC(CC)(c1ccc(OCC(O)C(C)(C)C)c(C)c1)c1cn(C)c2cc(CCC(=O)NO)ccc12] |
| (DK-305) | 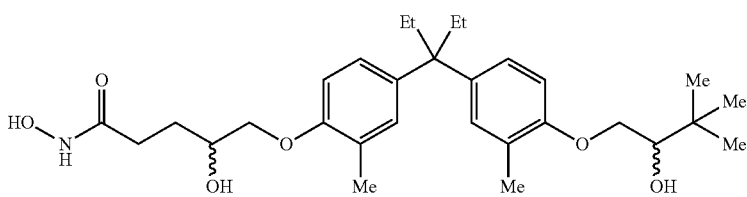 [SMILES: CCC(CC)(c1ccc(OCC(O)CCC(=O)NO)c(C)c1)c1ccc(OCC(O)C(C)(C)C)c(C)c1] |
| (DK-309) | 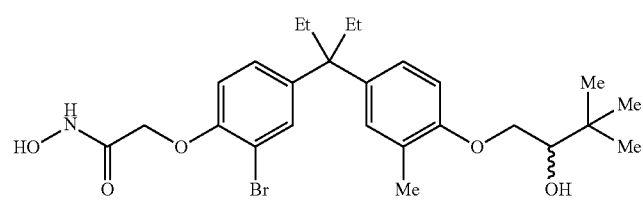 [SMILES: CCC(CC)(c1ccc(OCC(O)C(C)(C)C)c(C)c1)c1ccc(OCC(=O)NO)c(Br)c1] |

-continued
Compound
(DK-319)
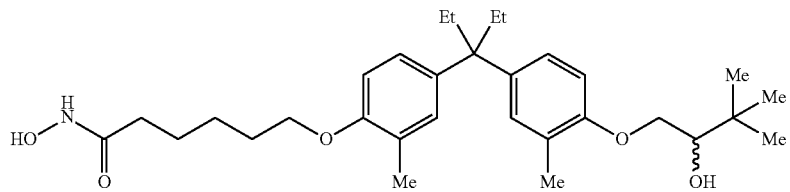 [SMILES: CCC(CC)(c1ccc(OCCCCCC(=O)NO)c(C)c1)c1ccc(OCC(O)C(C)(C)C)c(C)c1]
(DK-320)
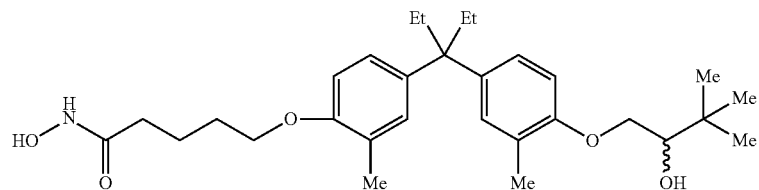 [SMILES: CCC(CC)(c1ccc(OCCCCC(=O)NO)c(C)c1)c1ccc(OCC(O)C(C)(C)C)c(C)c1]
(DK-331)
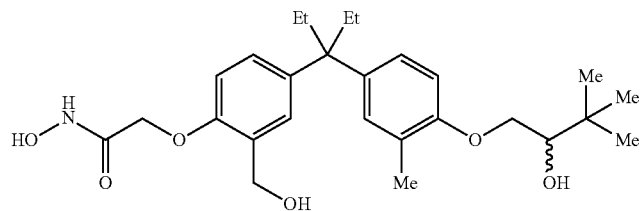 [SMILES: CCC(CC)(c1ccc(OCC(O)C(C)(C)C)c(C)c1)c1ccc(OCC(=O)NO)c(CO)c1]
(DK-341)
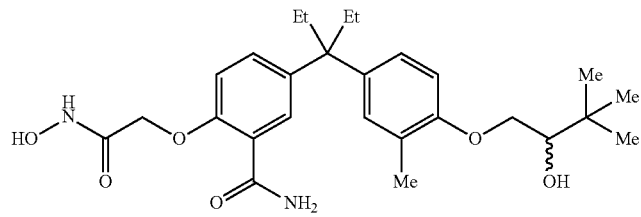 [SMILES: CCC(CC)(c1ccc(OCC(O)C(C)(C)C)c(C)c1)c1ccc(OCC(=O)NO)c(C(N)=O)c1]
(DK-347)
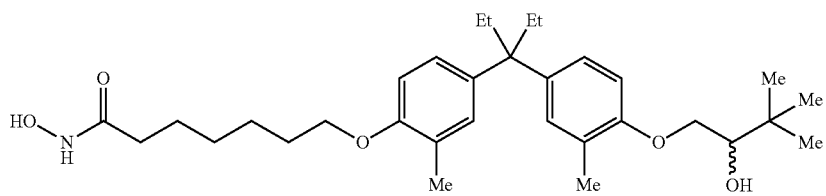 [SMILES: CCC(CC)(c1ccc(OCCCCCCC(=O)NO)c(C)c1)c1ccc(OCC(O)C(C)(C)C)c(C)c1]
(DK-361)
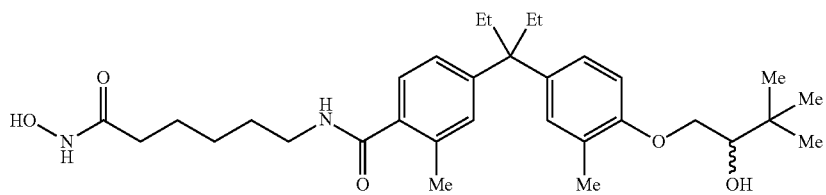 [SMILES: CCC(CC)(c1ccc(OCC(O)C(C)(C)C)c(C)c1)c1ccc(C(=O)NCCCCCC(=O)NO)c(C)c1]
(DK-362)
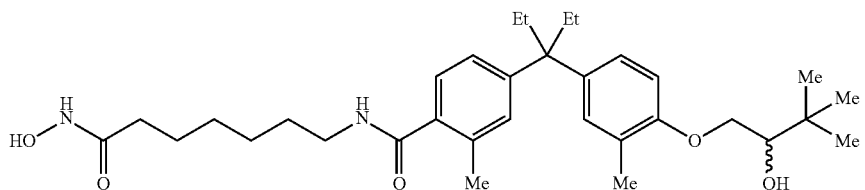 [SMILES: CCC(CC)(c1ccc(OCC(O)C(C)(C)C)c(C)c1)c1ccc(C(=O)NCCCCCCC(=O)NO)c(C)c1]

| Compound |
| --- |

(DK-366) [chemical structure]

(DK-367) [chemical structure]

(DK-381) [chemical structure]

(DK-405) [chemical structure]

(DK-406) [chemical structure]

In one embodiment, the present disclosure provides a method, use or composition for treating cancer comprising administering an effective amount of at least one compound as defined herein.

In one embodiment, the present disclosure provides a method, use or composition for limiting, or inhibiting the proliferation of cancer cells, or causing death of cancer cells in a patient, comprising administering au effective amount of at least one compound as defined herein.

In one embodiment, the present disclosure provides a method, use or composition for limiting or inhibiting the proliferation of, or causing death of 1,25D-resistant cell lines comprising administering an effective amount of at least one compound as defined herein.

In another embodiment, the expression "cancer" includes, but is not limited to, multiple myeloma, tumors of mesenchymal origin, including fibrosarcoma and rhabdomyosarcoma; and other tumors, including melanoma, seminoma, tetratocarcinoma, neuroblastoma and glioma. Examples of cancer include: carcinoma, including that of the bladder, breast, colon, kidney, liver, lung, ovary, pancreas, stomach, cervix, thyroid, skin, oral cavity, esophagus; hematopoietic tumors of lymphoid lineage, including acute lymphocytic leukemia, B-cell lymphoma and Burketts lymphoma; hematopoietic tumors of myeloid lineage, including acute and chronic myelogenous leukemias and promyelocytic leukemia, multiple myeloma; tumors of mesenchymal origin, including fibrosarcoma and rhabdomyosarcoma; and other tumors, including melanoma, seminoma, tetratocarcinoma, neuroblastoma and glioma.

In one embodiment, the present disclosure provides a method, use or composition for treating a cancer that is leukemia, non-small cell lung cancer, colon cancer, CNS cancer, melanoma, ovarian cancer, renal cancer, prostate cancer and breast cancer.

In one embodiment, the present disclosure provides a method, use or composition for modulating the vitamin D receptor (VDR) and inhibiting histone deacetylases (HDACs).

In another embodiment, the present disclosure provides a combination comprising a therapeutically effective amount of a compound, as defined herein, and a therapeutically effective amount of at least one or more therapeutic agents useful in the method of the present disclosure selected from: Alkylating agents, Anti-metabolites, Plant alkaloids and terpenoids, Vinca alkaloids, Podophyllotoxin, Taxanes, Topoisomerase inhibitors, and Cytotoxic antibiotics In another embodiment, the present invention provides a combination comprising a therapeutically effective amount of a compound, as defined herein, and a therapeutically effective amount of at least one or more therapeutic agents useful in the method of the present disclosure including but not limited to imatinib, paclitaxel, docetaxel, cisplatin, doxorubicine, vinblastine, zoledronate and/or in conjunction with antimetastatic agents, antiangionevic agents such as avastatin, and antiapoptotic compounds such as Valcade, agents targeting synthesis of estrogens or estrogen signaling through estrogen receptors including but not limited to arimidex and tamoxifen, agents targeting biosynthesis of androgens or androgen signaling through the androgen receptor including but not limited to bicalutamide, agents targeting HER2 including but not limited to trastuzumab, agents targeting BRAF including but not limited to Vemurafenib, or agents targeting members of the MAP kinase family or their upstream or downstream effector kinases.

It will be clear to a person of ordinary skill that if a further additional therapeutic agent is required or desired, ratios will be readily adjusted. It will be understood that the scope of combinations described herein is not particularly limited, but includes in principle any therapeutic agent useful for preventing, treating or slowing the progression of conditions or diseases defined herein.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician. Generally, the amount administered will be empirically determined, typically in the range of about 10 μg to 100 mg/kg body weight of the recipient. The amount administered can also appropriately be calculated based on the body surface and expressed as μg to mg/m$^2$ body surface.

The desired dose may conveniently be presented in a single dose or as divided dose administered at appropriate intervals, for example as two, three, four or more doses per clay.

Pharmaceutical compositions include, without limitation, those suitable for oral, (including buccal and sub-lingual), transdermal, or parenteral (including intramuscular, subcutaneous and intravenous) administration or in a form suitable for administration by inhalation or nasal spray.

The formulations may, where appropriate, be conveniently presented in discrete dosage units and may be prepared by any of the methods well known in the art of pharmacy. The methods for preparing a pharmaceutical composition can include the steps of bringing into association the compound as defined herein and pharmaceutically acceptable excipients and then, if necessary, shaping the product into the desired formulation, including applying a coating when desired.

Pharmaceutical compositions suitable for oral administration may conveniently be presented as discrete units such as capsules, cachets or tablets each containing a predetermined amount of the active ingredient; as a powder or granules; as a solution, a suspension or as an emulsion. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds and combinations as defined herein may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile water or saline, before use.

Compositions suitable for topical administration in the mouth include lozenges comprising the active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

For administration by inhalation, the compounds and combinations as defined herein may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

The compounds as defined herein may include a chiral center which gives rise to enantiomers. The compounds may thus exist in the form of two different optical isomers, that is (+) or (−) enantiomers. All such enantiomers and mixtures thereof, including racemic or other ratio mixtures of individual enantiomers, are included within the scope of the invention. The single enantiomer can be obtained by methods well known to those of ordinary skill in the art, such as chiral HPLC, enzymatic resolution and chiral auxiliary derivatization.

It will also be appreciated that the compounds in accordance with the present disclosure can contain more than one chiral centre. The compounds of the present invention may thus exist in the form of different diastereomers. All such diastereomers and mixtures thereof are included within the scope of the invention. The single diastereomer can be obtained by methods well known in the art, such as HPLC, crystallisation and chromatography.

There is also provided pharmaceutically acceptable salts of the compounds of the present invention. What is meant by the term pharmaceutically acceptable salts of the compounds is that they are derived from pharmaceutically acceptable inorganic and organic acids and bases. Examples of suitable acids include but are not limited to hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts. Salts derived from appropriate bases include alkali metal, alkaline earth metal or ammonium salts. The salt(s) must be "acceptable" in the sense of not being deleterious to the recipient thereof.

It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC) differential thermal analysis (DTA), thermogravimetric analysis (TGA)), Raman spectroscopy, comparative intrinsic dissolution rate, scanning electron microscopy (SEM).

The following examples are provided to further illustrate details for the preparation and use of the compounds of the present invention. They are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus.

General Description of Conditions/Materials

Unless otherwise stated, reactions were conducted under an argon atmosphere and glassware was flame dried under vacuum prior to use. Temperatures quoted as 0° C. and −78° C. were obtained by cooling the reaction vessel in baths of ice/water and dry ice/acetone respectively. Tetrahydrofuran and diethyl ether were purified by distillation from sodium benzophenone ketyl radical under a nitrogen atmosphere. Toluene, acetonitrile, dichloromethane and triethylamine were purified by distillation from calcium hydride under a dry air atmosphere. Deuterated chloroform was stored over activated 4 Å molecular sieves and anhydrous $K_2CO_3$. Deuterated methanol, acetone, and dimethylsulfoxide were purchased in analytically pure form in ampoules and used as received. Unless otherwise stated all other commercial reagents and solvents were used as purchased without further purification. Flash column chromatography was carried out on 230-400 mesh silica gel (Silicycle) using reagent grade solvents quoted as volume/volume mixtures. Thin-layer chromatography (TLC) was carried out on glass plates, coated with 250 μm of 230-400 mesh silica gel that had been saturated with F-254 indicator, and visualized by UV light (254 nm) then potassium permanganate, iron trichloride, vanillin or eerie ammonium molybdate stains. Infrared (IR) spectra were obtained using Nicolet Avatar 360 FT-IR infrared spectrophotometer. Proton and carbon nuclear magnetic resonance spectra were obtained on Varian 200, 300, 400, and 500 MHz spectrometers. Chemical shifts (δ) are reported in parts per million relative to tetramethylsilane and are referenced using the residual residual isotopomer with one less deuterium than the perdeuterated solvent: $^1H$ ($CDCl_3$ δ 7.26, $D_3COD$ δ 3.31, $(CD_3)_2SO$ δ 2.50), $^{13}C$ ($CDCl_3$ δ 77.16, $D_3COD$ δ 49.00, $(CD_3)_2SO$ δ 39.52). Coupling constants (J) are reported in Hertz (Hz).

The compounds of the present disclosure can be prepared according to the procedures denoted in the following Examples or modifications thereof using readily available starting materials, reagents, and conventional procedures or variations thereof well-known to a practitioner of ordinary skill in the art of synthetic organic chemistry. Specific definitions of variables in the Schemes are given for illustrative purposes only and are not intended to limit the procedures described.

EXAMPLE 1

Ethyl 2-(4-(3-(4-hydroxy-3-methylphenyl)pentan-3-yl)-2-methylphenoxy)acetate (2) and diethyl 2,2'-((pentane-3,3-diylbis(2-methyl-4,1-phenylene))bis(oxy))diacetate (3)

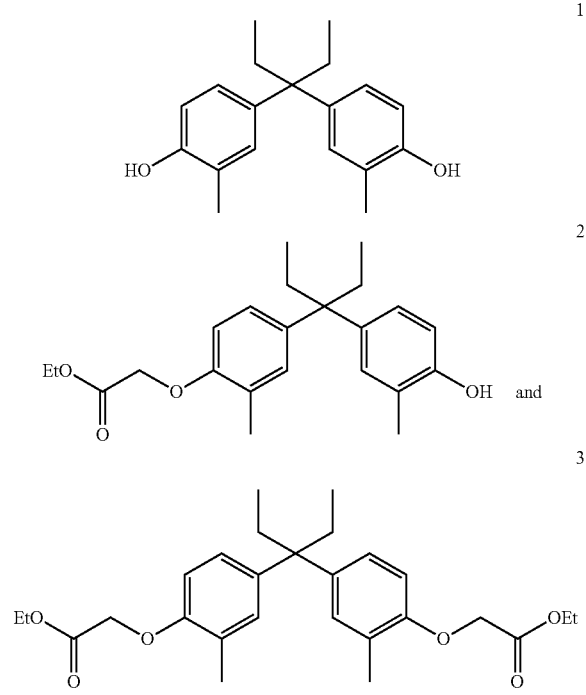

To a solution of compound 1 (797 mg, 2.804 mmol) in DMF (10 mL) was added NaH (67.3 mg, 112.2 mg of a 60% dispersion in paraffin wax, 2.804 mmol, 1.0 equiv.) at RT. After 2 h, ethyl bromoacetate (3.17 mL, 4.68 g, 28.04 mmol, 10.0 equiv.) was added and the resulting mixture stirred for 16 h. The solvent was then removed in vacuo then diluted with EtOAc and $H_2O$, and acidified with 1 M HCl to <pH3. The organic phase was isolated and the aqueous phase extracted with EtOAc (×3). The combined organic phases were washed with $H_2O$ (×2), brine, dried over $MgSO_4$ and concentrated in vacuo to give a brown oil that was purified by column chromatography (4:96 acetone/toluene) to afford compound 3 (248.2 mg, 19%), the title compound 2 (365.5 mg, 35%) and unreacted starting material 1 (427.7 mg, 53%).

Compound 2 was isolated as a colourless wax-like solid: $R_f$ 0.23 (4:96 acetone/toluene); IR (thin film) 3449, 2967, 1740, 1502, 1208 cm$^{-1}$; $^1H$ NMR (300 MHz, $CDCl_3$) d 6.95-6.82 (m, 4H), 6.64 (d, J=8.2, 1H), 6.57 (d, J=9.2, 1H), 4.60 (s, 2H), 4.57 (s, 1H), 4.26 (q, J=7.1, 2H), 2.22 (s, 3H), 2.19 (s, 3H), 2.00 (q, J=7.3, 4H), 1.28 (t, J=7.1, 3H), 0.58 (t, J=7.3, 6H)ppm; $^{13}C$ NMR (75 MHz, $CDCl_3$) d 169.7, 153.9, 151.5, 142.0, 141.1, 130.9, 130.7, 126.8, 126.2, 126.1, 122.6, 114.1, 110.3, 65.9, 61.4, 48.5, 29.4, 16.6, 16.2, 14.3, 8.6 ppm; HRMS (ESI) Calc. for $C_{23}H_{30}O_4Na$ [M+Na]$^+$: 393.2036, found: 393.2024.

Compound 3: off-white wax-like solid; $R_f$ 0.32 (4:96 acetone/toluene); IR (thin film) 2968, 1759, 1736, 1500, 1194, 1139 cm$^{-1}$; $^1$H NMR (300 MHz, CDCl$_3$) δ 6.94-6.87 (m, 4H), 6.57 (d, J=9.2, 2H), 4.60 (s, 4H), 4.26 (q, J=7.1, 4H), 2.22 (s, 6H), 2.00 (q, J=7.4, 4H), 1.28 (t, J=7.1, 6H), 0.58 (t, J=7.3, 6H) ppm; $^{13}$C NMR (75 MHz, CDCl$_3$) δ 182.3, 169.5, 153.9, 141.8, 130.9, 126.2, 126.1, 110.3, 65.9, 61.3, 48.6, 29.4, 16.6, 14.3, 8.6 ppm; HRMS (ESI) Calc. for C$_{27}$H$_{36}$O$_6$Na [M+Na]$^+$: 479.2404, found: 479.2383.

EXAMPLE 2

2-(4-(3-(4-(2-Ethoxy-2-oxoethoxy)-3-methylphenyl) pentan-3-yl)-2-methylphenoxy)acetic acid (4)

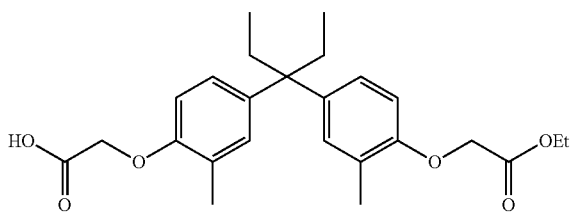 [SMILES: CCOC(=O)COc1ccc(C(CC)(CC)c2ccc(OCC(=O)O)c(C)c2)cc1C]

To a solution of compound 3 (200 mg, 0.438 mmol) in THF (3.0 mL) and MeOH (1.0 mL) at RT was added LiOH.H$_2$O (23.9 mg, 0.569 mmol, 1.3 equiv.). The resulting mixture was stirred at RT for 16 h before quenching by the addition of 1 M HCl until <pH3. The reaction mixture was diluted with H$_2$O and EtOAc and the organic phase was isolated. The aqueous phase was then extracted with EtOAc (×3) and the combined organic phases were dried over MgSO$_4$ and concentrated in vacuo to yield 211 mg of a crude residue that was purified by column chromatography (0.5:20:80 AcOH/acetone/hexanes) to afford unreacted starting material 3 (83.4 mg, 42%) and the title compound 4 (47.3 mg, 25%)

Compound 4: as a colourless film/oil: $R_f$ 0.27 (0.5:20:80 AcOH/acetone/hexanes); m (thin film) 2968, 1759, 1735, 1502, 1276 cm$^{-1}$; $^1$H NMR (300 MHz, CDCl$_3$) 7.01-6.85 (m, 4H), 6.65-6.53 (m, 2H), 4.65 (br s, 2H), 4.60 (s, 2H), 4.26 (q, J=7.1 Hz, 2H), 2.22 (s, 2×3H), 2.01 (q, J=7.2 Hz, 4H), 1.28 (t, J=7.2 Hz, 3H), 0.58 (t, J=7.2 Hz, 6H) ppm; $^{13}$C NMR (126 MHz, (CD$_3$)$_2$SO) δ 170.4, 168.9, 153.5, 153.4, 140.8, 140.5, 129.83, 129.82, 125.8, 125.7, 124.8, 124.7, 110.5, 110.2, 64.8, 64.6, 60.5, 47.7, 28.3, 16.40, 16.36, 14.0, 8.3 ppm; HRMS (ESI) Calc. for C$_{25}$H$_{32}$O$_6$Na [M+Na]$^+$: 451.2091. found: 451.2077.

EXAMPLE 3

Ethyl 2-(4-(3-(4-(3,3-dimethyl-2-oxobutoxy)-3-methylphenyl)pentan-3-yl)-2-methylphenoxy)acetate (5)

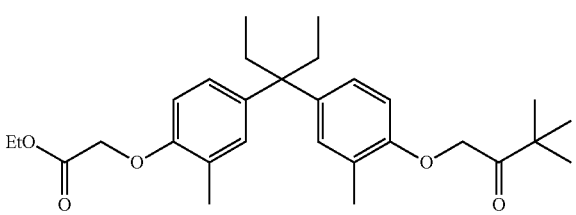 [SMILES: CCOC(=O)COc1ccc(C(CC)(CC)c2ccc(OCC(=O)C(C)(C)C)c(C)c2)cc1C]

Compound 2 (617.0 mg, 1.665 mmol) was dissolved in DMF (8.3 mL) and cooled to 0° C. To this solution was added NaH (46.3 mg of 95%, 44.0 mg, 1.832 mmol, 1.1 equiv.) and the resulting mixture was slowly warmed to RT over 1 h. 1-Chloropinacolone (322 µL, 314 mg, 2.33 mmol, 1.4 equiv.) was added via syringe and the reaction solution was heated to 80° C. for 6 h before cooling to RT and quenching by the addition of sat. aq. NH$_4$Cl solution. The mixture was diluted with H$_2$O and extracted with EtOAc (×3). The combined organic phases were washed with sat. aq. NaHCO$_3$, H$_2$O and brine then dried over MgSO$_4$ and concentrated in vacuo to give a crude product that was purified by column chromatography (17:83→20:80 EtOAc/hexanes) to give the title compound 5 (332.4 mg, 43%) as well as unreacted starting material 2 (331.8 mg, 54%).

Compound 5: colourless oil; $R_f$ 0.40 (20:80 EtOAc/hexanes); IR (thin film) 2967, 1760, 1727, 1501, 1198, 1142 cm$^{-1}$; $^1$H NMR (400 MHz, CDCl$_3$) δ 6.98-6.82 (m, 4H), 6.57 (d, J=9.1 Hz, 1H), 6.49 (d, J=8.3 Hz, 1H), 4.83 (s, 2H), 4.60 (s, 2H), 4.26 (q, J=7.2 Hz, 2H), 2.23 (s, 3H), 2.22 (s, 3H), 2.00 (q, J=7.2 Hz, 4H), 1.28 (t, J=7.2 Hz, 3H), 1.25 (s, 9H), 0.57 (t, J=7.3 Hz, 6H) ppm; $^{13}$C NMR (75 MHz, CDCl$_3$) δ 210.2, 169.5, 154.1, 153.9, 141.8, 141.5, 130.91, 130.88, 126.21, 126.17, 126.13, 126.06, 110.4, 110.2, 69.7, 65.9, 61.3, 48.6, 43.4, 29.4, 26.5, 16.8, 16.6, 14.3, 8.6 ppm; HRMS (ESI) Calc. for C$_{29}$H$_{40}$O$_5$Na [M+Na]$^+$: 491.2768, found: 491.2745.

EXAMPLE 4

2-(4-(3-(4-(3,3-Dimethyl-2-oxobutoxy)-3-methylphenyl)pentan-3-yl)-2-methylphenoxy)acetic acid (6)

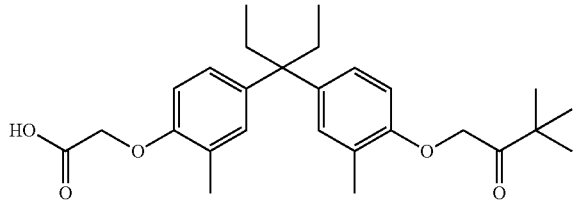 [SMILES: CCC(CC)(c1ccc(OCC(=O)O)c(C)c1)c1ccc(OCC(=O)C(C)(C)C)c(C)c1]

Compound 5 (50.0 mg, 0.1066 mmol) was dissolved in THF (1.0 mL) and H$_2$O (0.5 mL) and LiOH.H$_2$O (9.0 mg, 0.2133 mmol, 2.0 equiv.) was added. After stirring for 2 h, the reaction was quenched by the addition of sat. aq. NH$_4$Cl solution and diluted with H$_2$O. The resulting mixture was extracted with EtOAc (×3), and the combined organic phases were dried over MgSO$_4$ and concentrated in vacuo. The crude residue was purified by preparative tlc (1:5:94 AcOH/MeOH/CH$_2$Cl$_2$) to afford the title acid 6 (31.4 mg, 67%)

Compound 6: colourless film: $R_f$ 0.05 (10:90 acetone/toluene); IR (thin film) 2965, 2930, 2877, 1725, 1500, 1236, 1141 cm$^{-1}$; $^1$H NMR (500 MHz, CDCl$_3$) δ 6.97-6.85 (m, 4H), 6.61 (d, J=8.3 Hz, 1H), 6.49 (d, J=8.4 Hz, 1H), 4.83 (s, 2H), 4.65 (s, 2H), 2.23 (s, 3H), 2.22 (s, 3H), 2.01 (q, J=7.2 Hz, 4H), 1.25 (s, 9H), 0.58 (t, J=7.2 Hz, 6H) ppm; $^{13}$C NMR (126 MHz, CDCl$_3$) δ 210.2, 172.1, 154.2, 153.3, 142.7, 141.4, 131.2, 130.9, 126.5, 126.18, 126.0, 110.7, 110.3, 69.8, 65.5, 48.7, 43.4, 29.4, 26.5, 16.8, 16.6, 8.6 ppm; HRMS (ESI) Calc. for C$_{27}$H$_{36}$O$_5$Na [M+Na]$^+$: 463.2455, found: 463.2436.

EXAMPLE 5

N-(Benzyloxy)-2-(4-(3-(4-(3,3-dimethyl-2-oxobutoxy)-3-methylphenyl)pentan-3-yl)-2-methylphenoxy)acetamide (7)

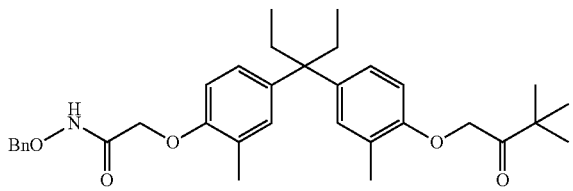 [SMILES: CCC(CC)(c1ccc(OCC(=O)NOCc2ccccc2)c(C)c1)c1ccc(OCC(=O)C(C)(C)C)c(C)c1]

To a solution of acid compound 6 (27.4 mg, 0.0622 mmol) in DMF (0.1 mL) was added BnONH$_2$, (10.5 mg, 0.0653 mmol, 1.05 equiv.), followed by $^i$Pr$_2$NEt (33 µL, 24 mg, 0.1866 mmol, 3.0 equiv.) and HBTU (25.6 mg, 0.0684 mmol, 1.1 equiv.). After 2 h, the reaction was quenched by the addition of brine and then extracted with EtOAc (×4). The combined organic phases were stirred with triethylamine resin, dried over Na$_2$SO$_4$ and concentrated in vacuo to give a crude product which was subsequently purified by preparative tlc (10:90 acetone/toluene). This afforded the title compound 7 (27.7 mg, 82%)

Compound 7: colourless film: R$_f$ 0.42 (10:90 acetone/toluene); IR (thin film) 3226, 2965, 2931, 2876, 1723, 1701, 1500, 1240, 1140 cm$^{-1}$; $^1$H NMR (400 MHz, CDCl$_3$) δ 8.79 (s, 1H), 7.42-7.32 (m, 5H), 6.99-6.91 (m, 1H), 6.91-6.82 (m, 3H), 6.60 (d, J=8.4 Hz, 1H), 6.48 (d, J=8.4 Hz, 1H), 4.96 (s, 2H), 4.83 (s, 2H), 4.53 (s, 2H), 2.22 (s, 3H), 2.03-1.96 (m, 7H), 1.25 (s, 9H), 0.57 (t, J=7.2 Hz, 6H) ppm; $^{13}$C NMR (75 MHz, CDCl$_3$) δ 210.1, 165.7, 154.2, 152.9, 142.7, 141.3, 134.8, 131.1, 130.8, 129.4, 129.1, 128.9, 126.5, 126.2, 126.1, 125.4, 110.29, 110.28, 78.8, 69.7, 67.3, 48.6, 43.3, 29.3, 26.5, 16.8, 16.5, 8.5 ppm; HRMS (ESI) Calc. for C$_{34}$H$_{43}$O$_5$NNa [M+Na]$^+$: 568.3033, found: 568.3011.

EXAMPLE 6

(JF-B59) 2-(4-(3-(4-(3,3-dimethyl-2-oxobutoxy)-3-methylphenyl)pentan-3-yl)-2-methylphenoxy)-N-hydroxyacetamide

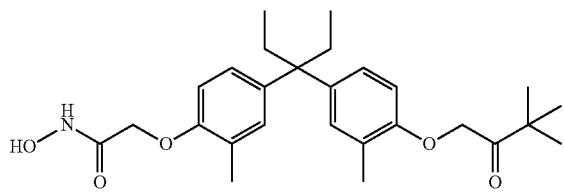 [SMILES: CCC(CC)(c1ccc(OCC(=O)NO)c(C)c1)c1ccc(OCC(=O)C(C)(C)C)c(C)c1]

Compound 7 (21.9 mg, 0.0401 mmol) was dissolved in EtOAc (1.0 mL) and 10% Pd/C (4.3 mg, 0.43 mg Pd, 0.0040 mmol, 10 mol % Pd) was added and the reaction vessel purged (×4) with H$_2$ $_{(g)}$. The reaction was stirred under a balloon of H$_2$ $_{(g)}$ for 0.5 h, before being purged (×2) with Ar$_{(g)}$. The reaction mixture was filtered through a pad of celite and rinsed with EtOAc. The filtrate was concentrated in vacuo to give the crude hydroxamic acid which was purified by octadecyl functionalized silica gel column chromatography (0:100→100:0 MeOH/H$_2$O) to afford the title hydroxamic acid (JF-B59) (14.6 mg, 80%). A portion of this (8.2 mg) was further purified, for biological testing, by HPLC (gradient elution, 50:50→95:5 MeOH/H$_2$O over 20 mins at 3 mL/min on a semi-preparative Zorbax Rx-C18 column) to afford analytically pure compound (JF-B59) (6.9 mg, 68% extrapolated yield)

Compound (JF-B59): colourless glassy solid: R$_f$ 0.15 (20:80 acetone/toluene); HPLC T$_r$ 7.56 min (80:20 MeOH/H$_2$O, 1.0 mL/min, Agilent Eclipse XDB-C18 analytical column); IR (thin film) 3234, 2966, 2934, 2877, 1725, 1677, 1501, 1244, 1140 cm$^{-1}$; $^1$H NMR (300 MHz, CD$_3$OD) δ 7.02-6.82 (m, 4H), 6.73 (d, J=8.5 Hz, 1H), 6.58 (d, J=8.5 Hz, 1H), 4.98 (s, 2H), 4.51 (s, 2H), 2.18 (s, 3H), 2.17 (s, 3H), 2.03 (q, J=7.2 Hz, 4H), 1.24 (s, 9H), 0.57 (t, J=7.3 Hz, 6H) ppm; $^{13}$C NMR (75 MHz, CD$_3$OD) δ 212.9, 168.2, 155.5, 155.2, 143.3, 142.6, 131.9, 131.7, 127.3, 127.2, 127.08, 127.06, 111.8, 111.5, 70.5, 67.9, 49.5, 44.1, 30.1, 26.6, 16.7, 16.6, 8.7 ppm; HRMS (ESI) Calc. for C$_{27}$H$_{37}$O$_5$NNa [M+Na]$^+$: 478.2564, found: 478.2551.

EXAMPLE 7

Ethyl 2-(4-(3-(4-(2-hydroxy-3,3-dimethylbutoxy)-3-methylphenyl)pentan-3-yl)-2-methylphenoxy)acetate ((2RS)-9)

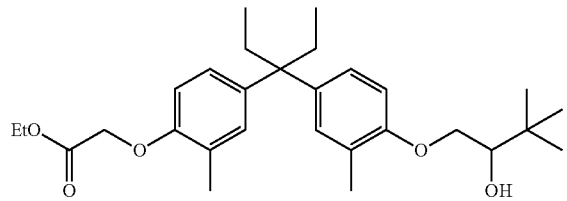

Compound 5 (82.7 mg, 0.1764 mmol) was dissolved in MeOH (3.0 mL) and cooled to 0° C. before the addition of NaBH$_4$ (7.1 mg, 0.176 mmol, 1.0 equiv.). The reaction was stirred at 0° C. for 2 h before quenching by the addition of acetone (ca. 0.5 mL) and warming to RT. The reaction solution was partitioned between sat. aq. NH$_4$Cl solution and CH$_2$Cl$_2$ and the organic phase was isolated. The aqueous phase was further extracted with CH$_2$Cl$_2$ (×2) and the combined organic phases were dried over MgSO$_4$ and concentrated in vacuo. The resulting crude residue was purified by column chromatography (1:20:80 MeOH/EtOAc/hexanes) to afford the title compound (2RS)-9 (74.0 mg, 89%)

Compound (2RS)-9: colourless film: R$_f$ 0.46 (1:20:80 MeOH/EtOAc/hexanes); IR (thin film) 3563, 2963, 1761, 1737, 1139 cm$^{-1}$; $^1$H NMR (400 MHz, CDCl$_3$) δ 6.98-6.86 (m, 4H), 6.69 (d, J=8.4 Hz, 1H), 6.57 (d, J=9.1 Hz, 1H), 4.60 (s, 2H), 4.26 (q, J=7.1 Hz, 2H), 4.09 (dd, J=9.2, 2.6 Hz, 1H), 3.85 (t, J=8.9 Hz, 1H), 3.70 (dd, J=8.8, 2.6 Hz, 1H), 2.46 (br s, 1H), 2.22 (s, 3H), 2.17 (s, 3H), 2.01 (q, J=7.3 Hz, 4H), 1.28 (t, J=7.1 Hz, 3H), 1.01 (s, 9H), 0.58 (t, J=7.2 Hz, 6H) ppm; $^{13}$C NMR (75 MHz, CDCl$_3$) δ 169.5, 154.4, 154.0, 141.9, 141.2, 130.9, 130.8, 126.3, 126.20, 126.19, 125.6, 110.4, 110.2, 77.4, 69.3, 66.0, 61.3, 48.6, 33.7, 29.4, 26.2, 16.8, 16.7, 14.3, 8.6 ppm; HRMS (ESI) Calc. for C$_{29}$H$_{42}$O$_5$Na [M+Na]$^+$: 493.2925, found: 493.2904.

EXAMPLE 8

Ethyl 2-(4-(3-(4-((2R)-hydroxy-3,3-dimethylbutoxy)-3-methylphenyl)pentan-3-yl)-2-methylphenoxy)acetate((2R)-9)

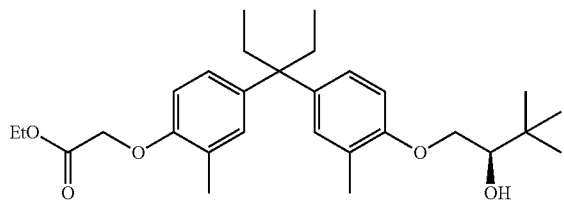 [SMILES: CCOC(=O)COc1ccc(C(CC)(CC)c2ccc(OC[C@H](O)C(C)(C)C)c(C)c2)cc1C]

Compound 5 (151.9 mg, 0.3241 mmol) was dissolved in toluene (6.5 mL) and (R)-2-methyl-CBS-oxazaborolidine (18.0 mg, 0.0648 mmol, 20 mol %) was added. To the resultant solution was added $BH_3.SMe_2$ (681 µL of a 2.0 M solution in TIFF, 1.361 mmol, 4.2 equiv.) via syringe and the reaction stirred at RT for 10 min before quenching by the addition of acetone, then 1 M HCl. When effervescence ceased, the reaction mixture was diluted with $H_2O$ and EtOAc. The organic phase was isolated and the aqueous phase extracted with EtOAc (×3). The combined organic phases were washed with sat. aq. $NaHCO_3$, then dried over $MgSO_4$ and concentrated in vacuo. The resultant residue was purified by column chromatography (20:80 EtOAc/hexanes) to give the title compound (2R)-9 (122.8 mg, 81%, 94.1% ee) as a colourless film. Spectral data were in accordance with that of compound (2RS)-9. HPLC $T_r$ 6.82 min (major), 9.55 min (minor), 10:90 $^i$PrOH/hexanes, 1 mL/min, Daicel chiralpak AD-H, 250×4.6 mm ID, 5 µm analytical column.

EXAMPLE 9

Ethyl 2-(4-(3-(4-((2S)-hydroxy-3,3-dimethylbutoxy)-3-methylphenyl)pentan-3-yl)-2-methylphenoxy)acetate((2S)-9)

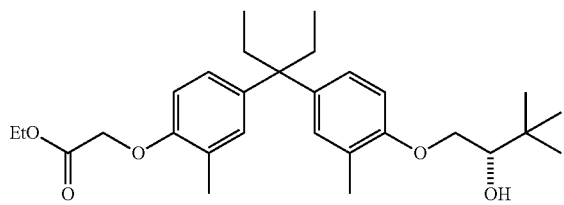 [SMILES: CCOC(=O)COc1ccc(C(CC)(CC)c2ccc(OC[C@@H](O)C(C)(C)C)c(C)c2)cc1C]

The title compound (2S)-9 was prepared from compound 5 (38.1 mg, 0.0813 mmol) using the same procedure as that outlined for the preparation of (2R)-9, utilising (S)-2-methyl-CBS-oxazaborolidine in place of (R)-2-methyl-CBS-oxazaborolidine. Purification by preparative tlc (20:80 EtOAc/hexanes) gave the title compound (2S)-9 (24.4 mg, 64%, 93.8% ee) as a colourless film. Spectral data were in accordance with that of (2RS)-9. HPLC $T_r$ 6.80 min (minor), 9.39 min (major), 10:90 $^i$PrOH/hexanes, 1 mL/min, Daicel chiralpak AD-H, 250×4.6 mm ID, 5 µm analytical column.

EXAMPLE 10

(JF-B01)N-Hydroxy-2-(4-(3-(4-(2-hydroxy-3,3-dimethylbutoxy)-3-methylphenyl)pentan-3-yl)-2-methylphenoxy)acetamide)

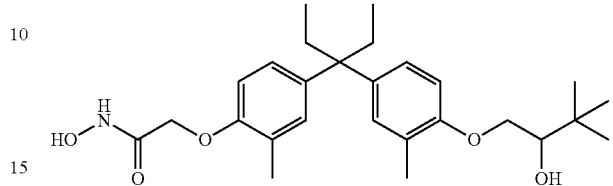

Compound (2RS)-9 (46.0 mg, 0.0977 mmol) was dissolved in THF (1.5 mL) and MeOH (1.5 mL) and cooled to 0° C. A cooled (ca. 0-5° C.) solution of $NH_2OH$ (3.23 mL of a 50% (w/v) aq. solution, 1.62 g, 48.9 mmol, 500 equiv.) was added to the ester solution, followed by KOH (38.4 mg, 0.6842 mmol, 7.0 equiv.) and the resulting reaction mixture stirred and slowly warmed to RT. After 20 h, the solvent was removed in vacuo and the residue diluted in $H_2O$ and acidified to <pH 3 with 1 M HCl before extracting with EtOAc (×5). The combined organic phases were dried ($Na_2SO_4$) and concentrated in vacuo to give a residue that was purified by octadecyl functionalized silica gel column chromatography (0:100→100:0 MeOH/$H_2O$) to afford the title hydroxamic acid compound (JF-B01) (42.4 mg, 94%). This was further purified by HPLC (gradient elution, 65:35→95:5 MeOH/$H_2O$ over 20 mins at 3 mL/min on a semi-preparative Zorbax Rx-C18 column) to afford analytically pure compound (32.9 mg, 74%) for biological testing.

Compound (JF-B01): white solid: $R_f$ 0.64 (10:90 MeOH/$CH_2Cl_2$; HPLC $T_r$ 3.38 min (90:10 MeOH/$H_2O$, 1.0 mL/min, Agilent Eclipse XDB-C18 analytical column); IR (thin film) 3232, 2963, 2876, 1678, 1502, 1260, 750 cm$^{-1}$; $^1$H NMR (300 MHz, $CD_3OD$) δ 7.03-6.80 (m, 4H), 6.75 (d, J=8.6 Hz, 1H), 6.74 (d, J=8.6 Hz, 1H), 4.51 (s, 2H), 4.11 (dd, J=10.0, 2.9 Hz, 1H), 3.86 (dd, J=10.0, 7.8 Hz, 1H), 3.62 (dd, J=7.8, 2, 8 Hz, 1H), 2.19 (s, 3H), 2.14 (s, 3H), 2.04 (q, J=7.2 Hz, 4H), 1.00 (s, 9H), 0.58 (t, J=7.2 Hz, 6H). ppm; $^{13}$C NMR (75 MHz, $CD_3OD$) δ 168.2, 156.3, 155.2, 143.5, 141.8, 131.9, 131.5, 127.3, 127.2, 127.1, 126.8, 111.8, 111.2, 78.7, 70.9, 67.9, 49.5, 35.1, 30.1, 26.6, 16.8, 16.6, 8.7 ppm; HRMS (ESI) Calc. for $C_2H_{39}NO_5Na$ [M+Na]$^+$: 480.2720, found: 480.2708.

EXAMPLE 11

(JF-C71)N-Hydroxy-2-(4-(3-(4-((2R)-hydroxy-3,3-dimethylbutoxy)-3-methylphenyl)pentan-3-yl)-2-methylphenoxy)acetamide)

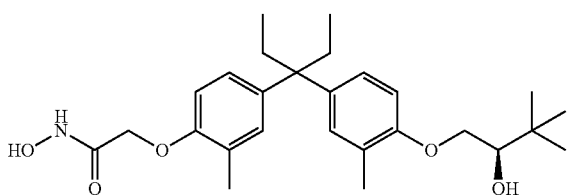 [SMILES: CCC(CC)(c1ccc(OCC(=O)NO)c(C)c1)c1ccc(OC[C@H](O)C(C)(C)C)c(C)c1]

The title compound (JF-C71) was prepared from ester (2R)-9 (68.0 mg, 0.1445 mmol) following the same procedure as that for compound (JF-B01). Purification of the crude product by octadecyl functionalized silica gel column chromatography (40:60→100:0 MeOH/H$_2$O) afforded the title hydroxamic acid (JF-C71) (53.2 mg, 80%). A portion of this (40.8 mg) was further purified, for biological testing, by HPLC (gradient elution, 67:33→95:5 MeOH/H$_2$O over 20 mins at 3 mL/min on a semi-preparative Zorbax Rx-C18 column) to afford analytically pure (JF-C71) (34.7 mg, 68% extrapolated yield) as a white solid. Spectral data were in accordance with that of (JF-B01). HPLC T$_r$ 4.63 min (85:15 MeOH/H$_2$O, 1.0 mL/min, Agilent Eclipse XDB-C18 analytical column).

EXAMPLE 12

(JF-C72), N-Hydroxy-2-(4-(3-(4-(2S)-hydroxy-3,3-dimethylbutoxy)-3-methylphenyl)pentan-3-yl)-2-methylphenoxy)acetamide((2S)-10)

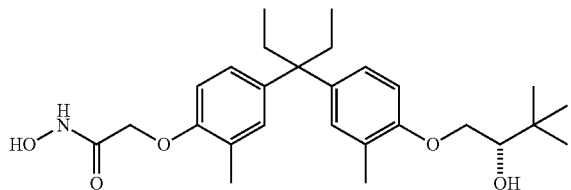 [SMILES: CCC(CC)(c1ccc(OCC(=O)NO)c(C)c1)c1ccc(OC[C@@H](O)C(C)(C)C)c(C)c1]

The title compound (JF-C72) was prepared from ester (2S)-9 (16.6 mg, 0.0353 mmol) following the same procedure as that for compound (JF-B01). Purification of the crude product by octadecyl functionalized silica gel column chromatography (40:60→100:0 MeOH/H$_2$O) afforded the title hydroxamic acid (JF-C72) which was further purified, for biological testing, by HPLC (gradient elution, 67:33→95:5 MeOH/H$_2$O over 20 mins at 3 mL/min on a semi-preparative Zorbax Rx-C18 column) to afford analytically pure (JF-C72) (5.8 mg, 36% extrapolated yield) as a white solid. Spectral data were in accordance with that of (JF-B01). HPLC T$_r$ 4.68 min (85:15 MeOH/H$_2$O, 1.0 mL/min, Agilent Eclipse XDB-C18 analytical column).

EXAMPLE 13

Ethyl 2-(4-(3-(4-(2-hydroxyethoxy)-3-methylphenyl)pentan-3-yl)-2-methylphenoxy)acetate (11)

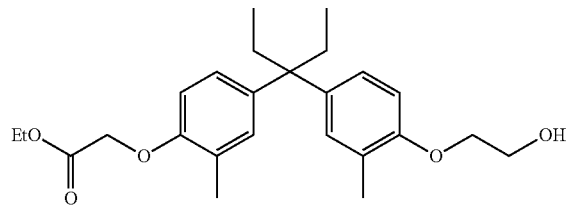 [SMILES: CCOC(=O)COc1ccc(C(CC)(CC)c2ccc(OCCO)c(C)c2)cc1C]

To a solution of compound 4 (59.7 mg, 0.1393 mmol) in THF (1.25 mL) at −10° C. was added BH$_3$•THF (140 µL of a 1.0 M solution in THF, 0.1393 mmol, 1.0 equiv.) and the resulting solution was warmed to RT and stirred for 16 h. the reaction was cooled to 0° C. and a further portion of BH$_3$ THF (140 µL of a 1.0 M solution in THF, 0.1393 mmol, 1.0 equiv.) was added. After warming to RT and stirring for 3 h, the reaction was re-cooled to 0° C. and quenched by the addition of H$_2$O and K$_2$CO$_3$ (ca. 20 mg). The resulting mixture was warmed to RT, diluted with H$_2$O and extracted with Et$_2$O (×4). The combined organic extracts were dried over MgSO$_4$ and concentrated in vacuo to afford a colourless oil which was purified by column chromatography (5:20:75 MeOH/EtOAc/hexanes) to afford the title compound 11 (52.4 mg, 91%)

Compound 11 as a colourless film: R$_f$ 0.36 (5:20:75 MeOH/EtOAc/hexanes); IR (thin film) 3483, 2966, 2936, 2877, 1760, 1502, 1246, 1199, 1140 cm$^{-1}$; $^1$H NMR (300 MHz, CDCl$_3$) δ 6.97-6.88 (m, 4H), 6.70 (d, J=8.4 Hz, 1H), 6.57 (d, J=9.2 Hz, 1H), 4.60 (s, 2H), 4.26 (q, J=7.1 Hz, 2H), 4.09-4.02 (m, 2H), 4.00-3.90 (m, 2H), 2.23 (s, 3H), 2.18 (s, 3H), 2.02 (q, J=7.2 Hz, 4H), 1.28 (t,j ×7.1 Hz, 3H), 0.59 (t, J=7.3 Hz, 6H) ppm; $^{13}$C NMR (75 MHz, CDCl$_3$) δ 169.5, 154.3, 153.9, 141.9, 141.3, 130.9, 130.8, 126.3, 126.18, 126.16, 125.6, 110.4, 110.2, 69.2, 65.9, 61.9, 61.3, 48.6, 29.4, 16.69, 16.65, 14.3, 8.6 ppm; HRMS (ESI) Calc. for C$_{25}$H$_{34}$O$_5$Na [M+Na]$^+$: 437.2299, found: 437.2281.

EXAMPLE 14

2-(4-(3-(4-(2-Hydroxy-2-methylpropoxy)-3-methylphenyl)pentan-3-yl)-2-methylphenoxy)acetic acid (12)

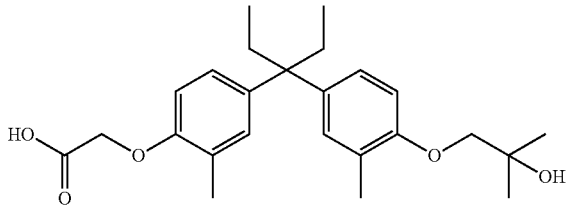 [SMILES: CCC(CC)(c1ccc(OCC(=O)O)c(C)c1)c1ccc(OCC(C)(C)O)c(C)c1]

To a solution of compound 4 (60.2 mg, 0.1405 mmol) in THF (0.7 mL) at 0° C. was added MeMgBr (145 µL of a 3M solution in Et$_2$O, 0.4355 mmol, 3.1 equiv.). After stirring at 0° C. for 3 h, the reaction was quenched by the addition of sat. aq. NH$_4$Cl solution, warmed to RT and diluted with H$_2$O. This was extracted with EtOAc (×3) and the combined organic phases were washed with H$_2$O and brine before drying over MgSO$_4$. The solution was concentrated in vacuo to give a colourless film that was purified by column chromatography (5:95 AcOH/CH$_2$Cl$_2$) to give unreacted starting material (14.1 mg, 23% recovery) and the title compound 12 (34.0 mg, 58%)

Compound 12: colourless film: R$_f$ 0.29 (5:95 AcOH/CH$_2$Cl$_2$); IR (thin film) 3421, 2968, 2930, 2876, 1736, 1501, 1235, 1136 cm$^{-1}$; $^1$H NMR (500 MHz, CDCl$_3$) δ 7.00-6.85 (m, 4H), 6.67 (d, J=8.5 Hz, 1H), 6.61 (d, J=8.2 Hz, 1H), 4.63 (br s, 2H), 3.77 (s, 2H), 2.22 (s, 3H), 2.19 (s, 3H), 2.02 (q, J=7.1 Hz, 4H), 1.35 (s, 6H), 0.60 (d, J=7.2 Hz, 6H) ppm; $^{13}$C NMR (126 MHz, CDCl$_3$) δ 172.9, 154.4, 153.4, 142.6, 141.0, 131.1, 130.7, 126.4, 126.3, 126.1, 125.6, 110.7, 110.2, 75.9, 70.5, 65.5, 48.6, 29.4, 26.3, 16.7, 16.6, 8.6 ppm; HRMS (ESI) Calc. for C$_{25}$H$_{34}$O$_5$Na [M+Na]$^+$: 437.2299, found: 437.2285.

EXAMPLE 15

2-(4-(3-(4-(2-Ethyl-2-hydroxybutoxy)-3-methylphenyl)pentan-3-yl)-2-methylphenoxy)acetic acid (13)

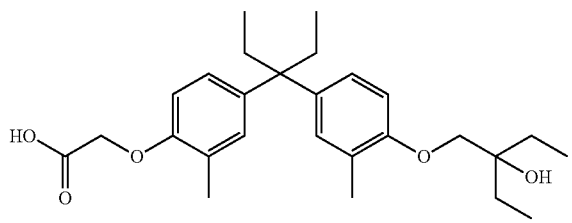 [SMILES: CCC(O)(CC)COc1ccc(C(CC)(CC)c2ccc(OCC(=O)O)c(C)c2)cc1C]

The title compound 13 was prepared from compound 4 (91.2 mg, 0.2128 mmol) and EtMgBr (227 μL of a 3.0 M solution in Et$_2$O, 0.681 mmol, 3.2 equiv.) following the same procedure as that for compound 12. Purification by column chromatography (1:10:90→2:15:85 AcOH/EtOAc/CH$_2$Cl$_2$) afforded the title compound 13 (55.2 mg, 59%)

Compound 13: colourless glassy solid: R$_f$ 0.33 (2:15:85 AcOH/EtOAc/CH$_2$Cl$_2$); IR (thin film) 3436, 2967, 2935, 2879, 1738, 1502, 1245, 1138 cm$^{-1}$; $^1$H NMR (500 MHz, CDCl$_3$) δ 6.96-6.91 (m, 3H), 6.88 (d, J=2.5 Hz, 1H), 6.69 (d, J=8.5 Hz, 1H), 6.61 (d, J=9.3 Hz, 1H), 4.64 (s, 2H), 3.80 (s, 2H), 2.22 (s, 3H), 2.17 (s, 3H), 2.02 (q, J=7.3 Hz, 4H), 1.71-1.61 (m, 4H), 0.93 (t, J=7.5 Hz, 6H), 0.59 (t, J=7.2 Hz, 6H) ppm; $^{13}$C NMR (126 MHz, CDCl$_3$) δ 173.2, 154.5, 153.4, 142.5, 140.9, 131.1, 130.7, 126.4, 126.3, 126.1, 125.7, 110.6, 110.1, 74.5, 72.4, 65.5, 48.6, 29.4, 28.8, 16.8, 16.6, 8.6, 7.9 ppm; HRMS (ESI) Calc. for C$_{27}$H$_{38}$O$_5$Na [M+Na]$^+$: 465.2612, found: 465.2599.

EXAMPLE 16

(JF-B52)N-Hydroxy-2-(4-(3-(4-(2-hydroxyethoxy)-3-methylphenyl)pentan-3-yl)-2-methylphenoxy)acetamide (14)

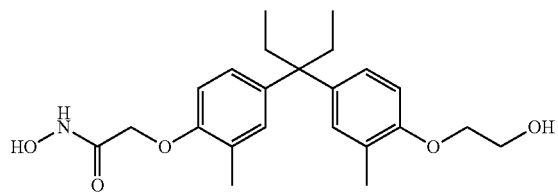 [SMILES: CCC(CC)(c1ccc(OCCO)c(C)c1)c1ccc(OCC(=O)NO)c(C)c1]

The title compound 14 was prepared from ester compound 11 (28.5 mg, 0.0688 mmol) following the same procedure as that for compound (JF-B01). Purification of the crude product by octadecyl functionalized silica gel column chromatography (0:100→100:0 MeOH/H$_2$O) afforded the title hydroxamic acid 14 (25.8 mg, 93%). A portion of this (15.8 mg) was further purified, for biological testing, by HPLC (gradient elution, 50:50→90:10 MeOH/H$_2$O over 20 mins at 3 mL/min on a semi-preparative Zorbax Rx-C18 column) to afford analytically pure compound (8.7 mg, 51% extrapolated yield)

Compound 14: colourless film: R$_f$ 0.31 (5:95 MeOH/CH$_2$Cl$_2$); HPLC T$_r$ 1.67 min (85:15 MeOH/H$_2$O, 1.5 mL/min, Agilent Eclipse XDB-C18 analytical column); IR (thin film) 3234, 2965, 2935, 2876, 1674, 1502, 1246, 1138 cm$^{-1}$; $^1$H NMR (400 MHz, CD$_3$OD) δ 6.99-6.91 (m, 2H), 6.89 (d, J=2.4 Hz, 1H), 6.83 (d, J=2.4 Hz, 1H), 6.78-6.71 (m, 2H), 4.51 (s, 2H), 4.01 (t, J=4.8 Hz, 2H), 3.87 (t, J=4.8 Hz, 2H), 2.18 (s, 3H), 2.14 (s, 3H), 2.04 (q, J=7.2 Hz, 4H), 0.57 (t, J=7.3 Hz, 6H) ppm; $^{13}$C NMR (126 MHz, CD$_3$OD) δ 168.3, 156.2, 155.2, 143.5, 141.9, 131.9, 131.5, 127.3, 127.2, 127.1, 126.9, 111.8, 111.4, 70.7, 67.9, 61.9, ~49 (obscured by CD$_3$OD), 30.2, 16.63, 16.62, 8.7 ppm; HRMS (ESI) Calc. for C$_{23}$H$_{31}$O$_5$NNa [M+Na]$^+$: 424.2094, found: 424.2081.

EXAMPLE 17

(JF-B53)N-Hydroxy-2-(4-(3-(4-(2-hydroxy-2-methylpropoxy)-3-methylphenyl)pentan-3-yl)-2-methylphenoxy)acetamide

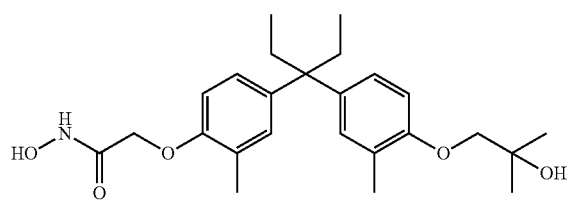 [SMILES: CCC(CC)(c1ccc(OCC(=O)NO)c(C)c1)c1ccc(OCC(C)(C)O)c(C)c1]

To a solution of acid compound 12 (27.7 mg, 0.0668 mmol) and TBSONH$_2$ (29.5 mg, 0.2005 mmol, 3.0 equiv.) in CH$_2$Cl$_2$ (1.7 mL) was added EDC.HCl (19.2 mg, 0.1002 mmol, 1.5 equiv.) in 1 portion. The resulting solution was stirred at RT for 20 h before being partitioned between H$_2$O and CH$_2$Cl$_2$. The organic phase was isolated and the aqueous phase extracted with CH$_2$Cl$_2$ (×4). The combined organic phases were dried (Na$_2$SO$_4$) and concentrated in vacuo to give the TBS-protected hydroxamic acid which was dissolved in THF (0.7 mL) and treated with TBAF (134 μL of a 1 M solution in THF, 0.134 mmol, 2.0 equiv.). After 2 h, the reaction was quenched by addition of sat. aq. NH$_4$Cl solution, then extracted with EtOAc (×4). The combined organic phases were dried over Na$_2$SO$_4$ and concentrated in vacuo to give a crude product that was purified by octadecyl functionalized silica gel column chromatography (0:100→100:0 MeOH/H$_2$O) to afford the title hydroxamic acid (JF-B53) (15.3 mg, 53%). For biological testing, a portion of this material (8.5 mg) was further purified by HPLC (gradient elution, 50:50→95:5 MeOH/H$_2$O over 20 mins at 3 mL/min on a semi-preparative Zorbax Rx-C18 column) to afford analytically pure compound (6.6 mg, 41% extrapolated yield)

Compound (JF-B53): colourless film: R$_f$ 0.31 (5:95 MeOH/CH$_2$Cl$_2$); HPLC T$_r$ 2.33 min (85:15 MeOH/H$_2$O, 1.5 mL/min, Agilent Eclipse XDB-C18 analytical column); IR (thin film) 3226, 2970, 2934, 2876, 1677, 1502, 1247, 1137 cm$^{-1}$; $^1$H NMR (500 MHz, CD$_3$OD) δ 7.00-6.91 (m, 2H), 6.89 (d, J=2.4 Hz, 1H), 6.84 (d, J=2.4 Hz, 1H), 6.74 (d, J=8.5 Hz, 1H), 6.73 (d, J=8.6 Hz, 1H), 4.51 (s, 2H), 3.74 (s, 2H), 2.19 (s, 3H), 2.15 (s, 3H), 2.04 (q, J=7.2 Hz, 4H), 1.33 (s, 6H), 0.58 (t, J=7.2 Hz, 6H) ppm; $^{13}$C NMR (126 MHz, CD$_3$OD) δ 168.2, 156.2, 155.2, 143.5, 141.9, 131.9, 131.5, 127.3, 127.23, 127.17, 126.8, 111.8, 111.2, 77.3, 71.1, 67.9, ~49 (obscured by CD$_3$OD), 30.2, 26.7, 16.65, 16.62, 8.7 ppm; HRMS (ESI) Calc. for C$_{25}$H$_{35}$O$_5$NNa [M+Na]$^+$: 452.2407, found: 452.2394.

EXAMPLE 18

(JF-B54), 2-(4-(3-(4-(2-Ethyl-2-hydroxybutoxy)-3-methylphenyl)pentan-3-yl)-2-methylphenoxy)-N-hydroxyacetamide

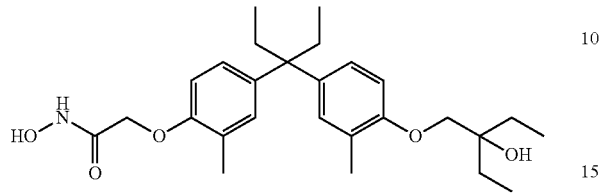

The title compound (JF-B54) was prepared from 13 (43.7 mg, 0.0987 mmol) following the same procedure as that for compound (JF-B53). Purification of the crude product by octadecyl functionalized silica gel column chromatography (0:100→100:0 MeOH/H$_2$O) afforded the title hydroxamic acid 16 (28.8 mg, 67%). A portion of this (16.1 mg) was further purified, for biological testing, by HPLC (gradient elution, 50:50→95:5 MeOH/H$_2$O over 20 mins at 3 mL/min on a semi-preparative Zorbax Rx-C18 column) to afford analytically pure compound (10.5 mg, 44% extrapolated yield).

Compound (JF-B54): colourless film: R$_f$ 0.33 (5:95 MeOH/CH$_2$Cl$_2$); HPLC T$_r$ 3.46 min (85:15 MeOH/H$_2$O, 1.5 mL/min, Agilent Eclipse XDB-C18 analytical column); IR (thin film) 3226, 2967, 2936, 2878, 1677, 1502, 1246, 1137 cm$^{-1}$; $^1$H NMR (400 MHz, CD$_3$OD) δ 7.00-6.92 (m, 2H), 6.89 (d, J=2.3 Hz, 1H), 6.83 (d, J=2.4 Hz, 1H), 6.74 (d, J=8.5 Hz, 1H), 6.73 (d, J=8.5 Hz, 1H), 4.51 (s, 2H), 3.77 (s, 2H), 2.18 (s, 3H), 2.13 (s, 3H), 2.04 (q, J=7.2 Hz, 4H), 1.75-1.59 (m, 4H), 0.92 (t, J=7.5 Hz, 6H), 0.58 (t, J=7.2 Hz, 6H) ppm; $^{13}$C NMR (75 MHz, CD$_3$OD) δ 168.3, 156.2, 155.2, 143.5, 141.8, 131.9, 131.5, 127.3, 127.23, 127.17, 126.7, 111.8, 111.0, 75.1, 73.0, 67.9, 49.5, 30.2, 30.1, 16.7, 16.6, 8.7, 7.9 ppm; ARMS (ESI) Calc. for C$_{27}$H$_{39}$O$_5$NNa [M+Na]$^+$: 480.2720, found: 480.2705.

EXAMPLE 19

1-(benzyloxy)-4-bromo-2-methylbenzene 17

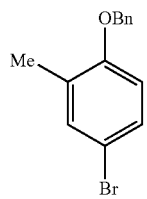 [SMILES: Cc1cc(Br)ccc1OCc1ccccc1]

To 4-bromo-2-methylphenol (1.25 g, 6.67 mmol) in 20 ml MeCN were added dry K$_2$CO$_3$ (1.84 g, 13.34 mmol, 2 equiv) and benzylbromide (0.872 ml, 7.34 mmol, 1.1 equiv) and reaction is stirred for 24 h at room temperature. Reaction mixture was filtered through Celite, solution was concentrated and purified by silica gel column chromatography (Hexane to 8% EtOAc/Hexane) to give 1.65 g 17 in 89% yield. R$_f$=0.90 (20% EtOAc/Hexane);

Compound 17: $^1$H NMR (300 MHz, CDCl$_3$) δ 7.45-7.31 (m, 5H), 7.29-7.21 (m, 2H), 6.74 (d, J=8, 6 Hz, 1H), 5.04 (s, 2H), 2.26 (s, 3H);

EXAMPLE 20 methyl 2-(4-(benzyloxy)-3-methylphenyl)-2-ethylbutanoate 18

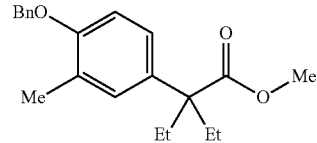 [SMILES: CCC(CC)(C(=O)OC)c1ccc(OCc2ccccc2)c(C)c1]

Synthetic procedure adopted from Hartwig J. F., J. Am. Chem. Soc., 2002, 124, 12557-12565 with several modifications.

To a solution of dicyclohexylamine (3.01 ml, 15.15 mmol, 1.4 equiv) in 10 ml dry toluene was added n-BuLi (5.96 ml, 2.54 M solution in hexane, 15.24 mmol, 1.4 equiv) at 0° C. Solution was stirred for 10 min at 0° C. before methyl 2-ethylpropionate (1.51 g, 12.98 mmol, 1.2 equiv) in 3 ml dry toluene was added. Reaction mixture was stirred for 30 min before it was added via cannula to solution containing compound 17 (1.08 g, 3.90 mmol, 1.0 equiv) and Pd$_2$(dba)$_3$ (35.7 mg, 0.039 mmol, 1 mol %) in 5 ml dry toluene. Finally, P(tBu)$_3$ (78.0 μl, 0.078 mmol, 2 mol %) was added from 1.0 M toluene stock solution. Reaction mixture was stirred under argon for 16 h. Diluted with 1 M HCl 15 ml and extracted with CH$_2$Cl$_2$ (3×10 ml). Then the combined organic layers were washed with H$_2$O (5 mL) and dried (Na$_2$SO$_4$). The solution was concentrated in vacuo then obtained oil was purified by silica gel column chromatography (Hexane to 10% EtOAc/Hexane) to give compound 2 980 mg in 77% yield. R$_f$=0.80 (20% EtOAc/Hexane);

Compound 18: $^1$H NMR (300 MHz, CDCl$_3$) 7.46-7.32 (m, 5H), 7.05-7.00 (m, 2H), 6.83 (d, J=6, 6 Hz, 1H), 5.07 (s, 2H), 3.67 (s, 3H), 2.29 (s, 3H), 2.10-1.94 (m, 4H), 0.72 (t, J=6.1 Hz, 6H);

EXAMPLE 21

2-(4-(benzyloxy)-3-methylphenyl)-2-ethylbutanoic acid 19

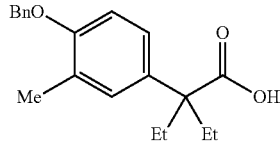 [SMILES: CCC(CC)(C(=O)O)c1ccc(OCc2ccccc2)c(C)c1]

To a solution of compound 18 (220 mg, 0.674 mmol) in 5 ml of MeOH was added 5 ml of 20% NaOH solution in water and refluxed for 48 h. Reaction mixture is acidified to pH 1 with 1 M HCl solution and extracted with EtOAc (3×5 ml), the combined organic layers were washed with H$_2$O and dried with Na$_2$SO$_4$. The solution was concentrated in vacuo to give compound 19 192 mg in 91% yield. R$_f$=0.10 (20% EtOAc/Hexane);

Compound 19: $^1$H NMR (400 MHz, CDCl$_3$) δ 7.45-7.32 (m, 5H), 7.13-7.07 (m, 2H), 7.10 (d, J=8.8 Hz, 1H), 5.07 (s, 2H), 2.27 (s, 3H), 2.13-1.94 (m, 4H), 0.76 (t, J=7.4 Hz, 6H).

Example 22

2-(4-(benzyloxy)-3-methylphenyl)-2-ethylbutanamide 20

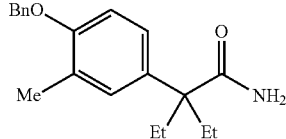 [SMILES: CCC(CC)(C(N)=O)c1ccc(OCc2ccccc2)c(C)c1]

To a solution of compound 19 (185 mg, 0.592 mmol) in 5 ml dry CH$_2$Cl$_2$ were added 1 drop of DMF and (COCl)$_2$ (101.6 μl, 1.184 mmol, 2.0 equiv), at 0° C. and reaction is allowed to heat to room temperature and stirred for 5 h. Then crude acid chloride is concentrated in vacuo and residue is dissolved in 5 ml dry THF. 20% NH$_4$OH (5 ml) was added and reaction is stirred at rt for 2 h. Reaction is acidified with 1M HCl to pH=7 and extracted with EtOAc (3×10 ml), then the combined organic layers were washed with H$_2$O and brine (5 mL) and dried with Na$_2$SO$_4$. The solution was concentrated in vacuo then the oil was purified by silica gel column chromatography (5% EtOAc/Hexane to 20% EtOAc/Hexane) to give compound 20 142 mg in 77% yield. R$_f$=0.20 (20% EtOAc/Hexane);

Compound 20: $^1$H NMR (300 MHz, CDCl$_3$) δ 7.45-7.31 (m, 5H), 7.11-7.06 (m, 2H), 6.84 (d, J=9.0 Hz, 1H), 5.17 (bs, 2H), 5.07 (s, 2H), 2.27 (s, 3H), 2.03-1.90 (m, 4H), 0.75 (t, J=7.4 Hz, 6H); $^{13}$C NMR (75 MHz, CDCl$_3$) δ 179.2, 155.6, 137.2, 134.9, 129.6, 128.4, 127.7, 127.0, 126.9, 125.2, 112.4, 110.8, 69.7, 53.7, 26.8, 16.5, 8.2.

EXAMPLE 23

α-Bromoketone 21b-c

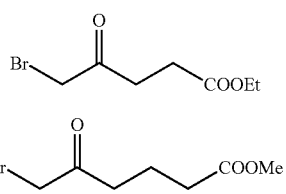

Appropriate α-bromoketone 21b was prepared by bromination of ethyl 4-oxopentanoate by bromine in acetic acid. α-bromoketone 21c was prepared according to literature (Lugtenburg J. et. al., *Eur. J. Org. Chem.* 2002, 189-2202) from ethyl acetoacetate and methyl acrylate in 1,4-addition reaction and subsequent decarboxylation under acidic conditions to give 5-oxohexanoic acid. Esterification and bromination gave α-bromoketone 21c (methyl 6-bromo-5-oxohexanoic acid) in 4 step procedure. α-Chloroketone 21a

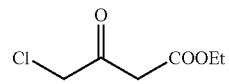

EXAMPLE 24

Ethyl 2-(2-(3-(4-(benzyloxy)-3-methylphenyl)pentan-3-yl)oxazol-4-yl)acetate 22 a Ethyl 3-(2-(3-(4-(benzyloxy)-3-m ethylphenyl)pentan-3-yl)oxazol-4-yl)propan oate 22 b Methyl 4-(2-(3-(4-(benzyloxy)-3-methylphenyl) pentan-3-yl)oxazol-4-yl)butanoate 22 c

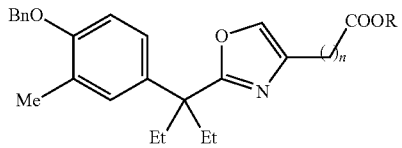

a: n = 1, R = Et
b: n = 2, R = Et
c: n = 3, R = Me

Appropriate α-haloketone 21 a-c (0.578 mmol, 2 equiv) was added to amide 20 (90 mg, 0.289 mmol, 1 equiv) in 5 ml DMF. The reaction mixture was stirred at 135° C. for 12 h. Cooled to room temperature and diluted with 20 ml of water, extracted with EtOAc (3×10 ml), then the combined organic layers were washed with H$_2$O (5 mL) and dried with Na$_2$SO$_4$. The solution was concentrated in vacuo then the oil was purified by silica gel column chromatography (Hexane to 10% EtOAc/Hexane).

Compound 22a: R$_f$=0.70 (20% EtOAc/Hexane); Yield 42%, $^1$H NMR (300 MHz, CDCl$_3$) δ 7.53 (s, 1H), 7.46-7.29 (m, 5H), 6.96-6.91 (m, 2H), 6.80 (d, J=9.3 Hz, 1H), 5.04 (s, 2H), 4.20 (quartet, J=6.5 Hz, 2H), 3.64 (s, 2H), 2.24 (s, 3H), 2.23-2.13 (m, 4H), 1.27 (t, J=6.0 Hz, 3H), 0.70 (t, J=6.1 Hz, 6H);

Compound 22b: R$_f$=0.70 (20% EtOAc/Hexane); Yield 48%, $^1$H NMR (300 MHz, CDCl$_3$) δ 7.46-7.31 (m, 5H), 7.28 (s, 1H), 6.95-6.80 (m, 2H), 6.79 (d, J=9.2 Hz, 2H), 5.04 (s, 2H), 4.13 (quart, J=7.1 Hz, 2H), 2.86 (t, J=7.2 Hz, 2H), 2.67 (t, J=7.2 Hz, 2H), 2.24 (s, 3H), 2.22-2.14 (m, 4H), 1.23 (t, J=7.3 Hz, 3H), 0.69 (t, J=7.3 Hz, 6H);

Compound 22c: R$_f$=0.70 (20% EtOAc/Hexane); Yield 47%, $^1$H NMR (300 MHz, CDCl$_3$) δ 7.45-7.32 (m, 5H), 7.27 (s, 1H, overlap), 6.96-6.90 (m, 2H), 6.80 (d, J=9.1 Hz, 1H), 5.04 (s, 2H), 3.67 (s, 3H), 2.59 (t, J=7.3 Hz, 2H), 2.39-2.31 (m, 2H), 2.24 (s, 3H), 2.21-2.11 (m, 4H), 1.99-1.94 (m, 2H), 0.69 (t, J=7.4 Hz, 6H);

EXAMPLE 25

Ethyl 2-(2-(3-(4-hydroxy-3-methylphenyl)pentan-3-yl)oxazol-4-yl)acetate 23 a

Ethyl 2-(2-(3-(4-hydroxy-3-methylphenyl)pentan-3-yl)oxazol-4-yl)propanoate 23 b

Methyl 2-(2-(3-(4-hydroxy-3-methylphenyl)pentan-3-yl)oxazol-4-yl)butanoate 23 c

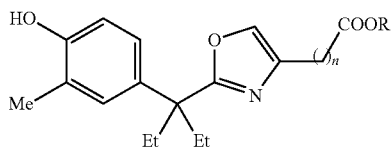

Appropriate oxazole derivative 22 a-c (0.200 mmol, 1 equiv) was dissolved in 3 ml MeOH:EtOAc 1:1 and 10 wt % Pd/C (0.010, 5 mol %) was added and reaction was stirred under $H_2$ atmosphere O/N. Filtered through Celite and concentrated in vacuo to give quantitative yield in all cases 23 a-c.

Compound 23a: $R_f$=0.50 (20% EtOAc/Hexane); Yield quant; $^1$H NMR (300 MHz, CDCl$_3$) δ 7.53 (s, 1H), 6.89-6.84 (m, 2H), 6.67 (d, J=8.2 Hz, 1H), 4.69 (bs, 1H), 4.19 (quart, J=7.0 Hz), 2.25-2.09 (m, 4H), 2.20 (s, 3H), 3.64 (s, 2H), 2.25-2.09 (m, 4H), 2.20 (s, 3H), overlap), 1.27 (t, J=7.1 Hz, 3H), 0.69 (t, J=7.4 Hz, 6H);

Compound 23b: $R_f$=0.50 (20% EtOAc/Hexane); Yield quant; $^1$H NMR (300 MHz, CDCl$_3$) δ 7.28 (s, 1H), 6.89-6.82 (m, 2H), 6.67 (d, J=8.3 Hz, 1H), 4.64 (bs, 1H), 4.06 (quart, J=8.0 Hz, 2H), 2.87 (t, J=7.5 Hz, 1H), 2.66 (t, J=7.6 Hz, 1H), 2.16 (s, 3H), 2.20-2.13 (m, 4H), 1.25 (t, J=7.2 Hz, 3H), 0.68 (t, J=7.4 Hz, 6H);

Compound 23c: $R_f$=0.55 (20% EtOAc/Hexane); Yield quant; $^1$H NMR (300 MHz, CDCl$_3$) δ 7.27 (s, 1H, overlap), 6.89-6.82 (m, 2H), 6.67 (d, J=8.5 Hz, 1H), 4.66 (s, 1H), 3.67 (s, 3H), 2.58 (t, J=7.6 Hz, 2H), 2.39-2.31 (m, 2H), 2.24-2.10 (m, 4H), 2.20 (s, 3H, overlap), 1.99-1.93 (m, 2H), 0.68 (t, j=7.4 Hz, 2H);

EXAMPLE 26

Ethyl 2-(2-(3-(4-(3,3-dimethyl-2-oxobutoxy)-3-methyl phenyl)pentan-3-yl)oxazol-4-yl)acetate 24 a Ethyl 2-(2-(3-(4-(3,3-dimethyl-2-butoxy)-3-methyl-phenyl)pentan-3-yl)oxazol-4-yl)propanoate 24 b Methyl 2-(2-(3-(4-(3,3-dimethyl-2-oxo butoxy)-3-methylphenyl)pentan-3-yl)oxazol-4-yl)butanoate 24 c

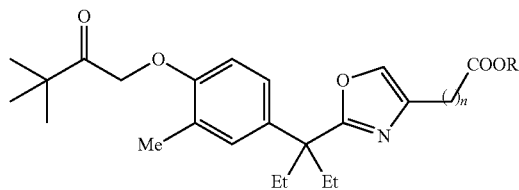

To appropriate phenol derivative 23 a-c (1 equiv) in MeCN were added $K_2CO_3$ (2 equiv) and 1-chloropinacolone (1.5 equiv) and reaction mixture was stirred for 24 h at room temperature. Filtered through Celite, concentrated in vacuo and purified by silica gel column chromatography (Hexane to 10% EtOAc/Hexane)

Compound 24a: $R_f$=0.50 (20% EtOAc/Hexane); Yield 79%; $^1$H NMR (300 MHz, CDCl$_3$) δ 7.53 (s, 1H), 6.96-6.87 (m, 2H), 6.53 (d, J=8.2 Hz, 1H), 4.83 (s, 2H), 4.19 (quart, J=7.2 Hz, 2H), 3.64 (s, 2H), 2.25 (s, 3H), 2.23-2.10 (m, 4H), 1.29-1.21 (m, 12H), 0.68 (t, J=7.4 Hz, 6H).

Compound 24b $R_f$=0.50 (20% EtOAc/Hexane); Yield 87%; $^1$H NMR (300 MHz, CDCl$_3$) δ 7.28 (s, 1H, overlap), 6.94-6.85 (m, 2H), 6.53 (d, J=8, 4 Hz, 1H), 4.82 (s, 2H), 4.13 (quart, J=7.2 Hz, 2H), 2.87 (t, J=7.3 Hz, 2H), 2.66 (t, J=7.4 Hz, 2H), 2.25 (s, 3H), 2.20-2.09 (m, 4H), 1.28-1.21 (m, 12H), 0.67 (t, J=7.3 Hz, 5H).

Compound 24c $R_f$=0.60 (20% EtOAc/Hexane); Yield 82%; $^1$H NMR (300 MHz, CDCl$_3$) δ 7.28 (s, 1H, overlap), 6.96-6.87 (m, 2H), 6.53 (d, J=8.7 Hz, 1H), 4.83 (s, 2H), 3.67 (s, 1H), 2.58 (t, J=7.2 Hz, 1H), 2.37 (t, J=7.6 Hz, 1H), 2.25 (s, 3H), 2.21-2.10 (m, 4H), 2.04-1.94 (m, 2H), 1.25 (s, 1H), 0.68 (t, J=7.4 Hz, 3H).

EXAMPLE 27

Methyl 2-(2-(3-(4-(2-hydroxy-3-dimethylbutoxy)-3-methylphenyl)pentan-3-yl)oxazol-4-yl)acetate 25 a Ethyl 2-(2-(3-(4-(2-hydroxy-3,3-dimethylbutoxy)-3-methylphenyl)pentan-3-yl)oxazol-4-yl) propanoate 25 b Methyl 2-(2-(3-(4-(2-hydroxy-3,3-dimethylbutoxy-3-methylphenyl)pentan-3-yl)oxazol-4-yl)propanoate 25 c

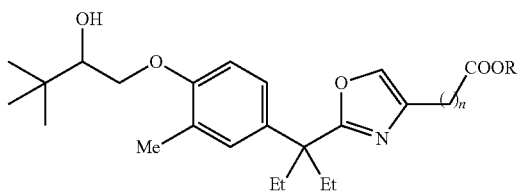

To appropriate ketone 24 a-c in 5 ml EtOH (MeOH in case 24c) at 0° C. was added NaBH$_4$ (1.5 equiv) at 0° C. and reaction was stirred for 30 min and then heated up to room temperature during 1 h period. 1 M HCl was added and product extracted with EtOAc (3×10 ml), then the combined organic layers were washed with H$_2$O (5 mL) and dried with Na$_2$SO$_4$. The solution was concentrated in vacuo and product was enough pure for next step in all cases 9 a-c Compound 25a: $R_f$=0.45 (20% EtOAc/Hexane); Yield 87% $^1$H NMR (400 MHz, CDCl$_3$) δ 7.52 (s, 1H), 6.95-6.91 (m, 2H), 6.74 (d, J=8.2 Hz, 1H), 4.08 (d, J=9.1 Hz, 1H), 3.85 (t, J=9.0 Hz, 1H), 3.74 (s, 3H), 3.69 (d, J=8.5 Hz, 1H), 3.65 (s, 2H), 2.19 (s, 3H), 2.21-2.12 (m, 4H), 1.01 (s, 9H), 0.69 (t, J=7.4 Hz, 6H);

Compound 25b: $R_f$=0.45 (20% EtOAc/Hexane); Yield 85%, $^1$H NMR (300 MHz, CDCl$_3$) δ 6.95-6.89 (m, 2H), 6.73 (d, J=8.0 Hz), 4.13 (quart, J=6.6 Hz, 2H), 4.08 (d, J=10.0 Hz, 1H), 3.85 (t, J=10.0 Hz, 1H), 3.69 (d, J=10.0, 1H), 2.86 (t, J=7.2 Hz, 2H), 2.67 (t, J=7.2 Hz, 2H), 2.24-2.10 (m, 4H), 2.19 (s, 3H, overlap), 1.24 (t, J=7.1 Hz, 2H), 1.01 (s, 9H), 0.68 (t, I=7.4 Hz, 2H);

Compound 25c: $R_f$=0.45 (20% EtOAc/Hexane); Yield 91% $^1$H NMR (400 MHz, CDCl$_3$) δ 7.27 (s, 1H, overlap), 6.95-6.90 (m, 2H), 6.74 (d, J=8.2 Hz, 1H), 4.08 (d, J=9.2 Hz, 1H), 3.85 (t, J=8.9 Hz, 1H), 3.70 (d, J=10.0 Hz, 1H), 3.67 (s, 3H), 2.58 (t, J=7.0 Hz, 1H), 2.38 (t, J=7.0 Hz, 2H), 2.23-2.13 (m, 4H), 2.19 (s, 1H), 2.02-1.96 (m, 2H), 1.01 (s, 9H), 0.69 (t, J=7.4 Hz, 6H);

EXAMPLE 28

3-(2-(3-(4-(benzyloxy)-3-methylphenyl)pentan-3-yl)oxazol-4-yl)propanal 27

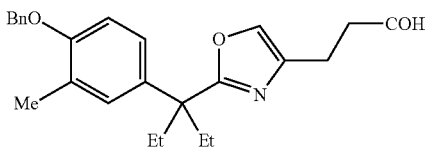

DIBALH (723 µl of a 1 M solution in toluene, 0.723 mmol) was added dropwise to a stirred solution of ester 6b (0.344 mmol, 150.0 mg, 1 equiv) in 10 mL dry CH$_2$Cl$_2$ under Ar at –78° C. The solution was stirred at –78° C. for 1 h and warmed up to room temperature and stirred O/N. Then 10 ml of CH$_2$Cl$_2$ was added to the reaction mixture, then 10 mL 1 M NaOH was added and solution stirred for 30 min. The solution was filtered, the precipitate washed with 5 mL CH$_2$Cl$_2$ and the combined organic fractions were dried with Na$_2$SO$_4$ and concentrated in vacuo. To an intermediate alcohol in 10 ml EtOAc was added IBX (0.378 mmol, 105.8 mg) and reaction mixture was refluxed for 5 h, cooled to room temperature, filtered through Celite and concentrated in vacuo. Then purified by silica gel column chromatography (8% EtOAc in hexanes) to afford 69.22 mg of aldehyde 11 in 52% yield. $R_f$=0.5 (20% EtOAc in hexanes);

Compound 27: $R_f$=0.60 (20% EtOAc/Hexane); Yield 52% $^1$H NMR (300 MHz, CDCl$_3$) δ 9.84 (s, 1H), 7.46-7.28 (m, 5H), 7.28 (s, 1H, overlap), 6.94-6.89 (m, 2H), 6.80 (d, J=8.3 Hz, 1H), 5.04 (s, 2H), 2.91-2.78 (m, 4H), 2.24 (s, 3H), 2.24-2.12 (m, 4H), 0.69 (t, J=7.4 Hz, 6H).

EXAMPLE 29

1-(2-(3-(4-(benzyloxy)-3-methylphenyl)pentan-3-yl)oxazol-4-yl)-4,4-dimethylpentan-3-ol

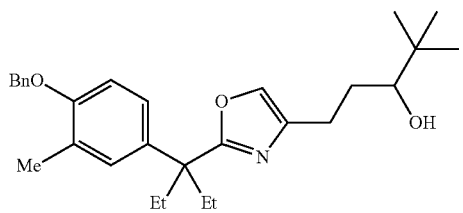 [SMILES: CCC(CC)(c1ccc(OCc2ccccc2)c(C)c1)c1nc(CCC(O)C(C)(C)C)co1]

To aldehyde 27 (35.0 mg, 0.089 mmol) in 5 ml dry THF under argone atmosphere at –78° C. was dropwise added t-BuMgCl (89 µl, of 2 M solution in diethyl ether, 0.178 mmol) over 15 min period and reaction mixture was stirred at –78° C. for 2 hours, and then allowed to heat to room temperature and stirred O/N. Acidified with 1 M HCl solution and crude product was extracted with EtOAc (3×10 ml), then the combined organic layers were washed with H$_2$O (5 mL) and dried with Na$_2$SO$_4$. The solution was concentrated in vacuo then the oil was purified by silica gel column chromatography (Hexane to 10% EtOAc/Hexane) to afford 27.0 mg of compound 28 in 67% yield. $R_f$=0.45 (20% EtOAc in hexanes);

Compound 28: Yield 67%; $R_f$=0.60 (20% EtOAc in hexanes); $^1$H NMR (300 MHz, CDCl$_3$) δ 7.45-7.30 (m, 5H), 7.27 (s, 1H, overlap), 6.95-6.90 (m, 2H), 6.79 (d, J=10.0 Hz, 1H), 5.04 (s, 2H), 3.23 (d, J=10.1 Hz, 1H), 2.85-2.80 (m, 1H), 2.75-2.66 (m, 1H), 2.29-2.11 (m, 4H), 2.24 (s, 3H), 1.93-1.84 (m, 1H), 1.60-1.50 (m, 1H), 0.91 (s, 9H), 0.69 (t, J=7.3 Hz, 6H).

EXAMPLE 30 ethyl 2-(4-(3-(4-(3-hydroxy-4,4-dimethylpentyl)oxazol-2-yl)pentan-3-yl)-2-methylphenoxy)acetate 29

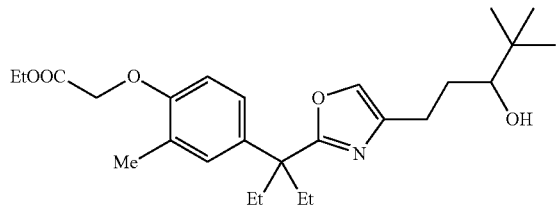 [SMILES: CCOC(=O)COc1ccc(C(CC)(CC)c2nc(CCC(O)C(C)(C)C)co2)cc1C]

The benzyloxy derivative of example 29 was subjected to hydrogenation as described in example 25 to obtain the corresponding phenol derivative. To the phenol (14.0 mg, 0.0389 mmol, 1 equiv) in MeCN were added K$_2$CO$_3$ (10.7 mg, 0.0778 mmol, 2 equiv) and ethyl 2-bromoacetate (5.18 µl, 0.0467 mmol, 1.2 equiv) and reaction mixture was stirred for 24 h at room temperature. Filtered trough Celite, concentrated in vacuo and purified by silica gel column chromatography (Hexane to 10% EtOAc/Hexane) to afford 16.0 mg of 29 in 92% yield. $R_f$=0.45 (20% EtOAc in hexanes);

Compound 29: Yield 92%; $^1$H NMR (400 MHz, CDCl$_3$) δ 7.27 (s, 1H), 6.95-6.87 (m, 2H), 6.60 (d, J=8.1 Hz, 1H), 4.59 (s, 2H), 4.25 (q, J=7.1 Hz, 1H), 3.66 (d, J=5.2 Hz, 1H), 3.23 (d, J=10.1 Hz, 1H), 2.85-2.79 (m, 1H), 2.75-2.63 (m, 1H), 2.29-2.11 (m, 4H), 2.23 (s, 3H), 1.93-1.84 (m, 1H), 1.60-1.50 (m, 1H), 1.27 (t, J=7.1 Hz, 3H), 0.91 (s, 9H), 0.68 (t, J=7.0 Hz, 1H);

EXAMPLE 31

N-hydroxy-2-(2-(3-(4-(2-hydroxy-3,3-dimethylbutoxy)-3-methylphenyl)pentan-3-yl)oxazol-4-yl)acetamide (DK-65)

N-hydroxy-3-(2-(3-(4-(2-hydroxy-3,3-dimethylbutoxy)-3-methylphenyl)pentan-3-yl)oxazol-4-yl)propanamide (DK-71)

N-hydroxy-4-(2-(3-(4-(2-hydroxy-3,3-di methylbutoxy)-3-methylphenyl)pentan-3-yl)oxazol-4-yl)butanamide (DK-90)

N-hydroxy-2-(4-(3-(4-(3-hydroxy-4,4-dimethylpentyl)oxazol-2-yl)pentan-3-yl)-2-methylphenoxy)acetamide (DK-91)

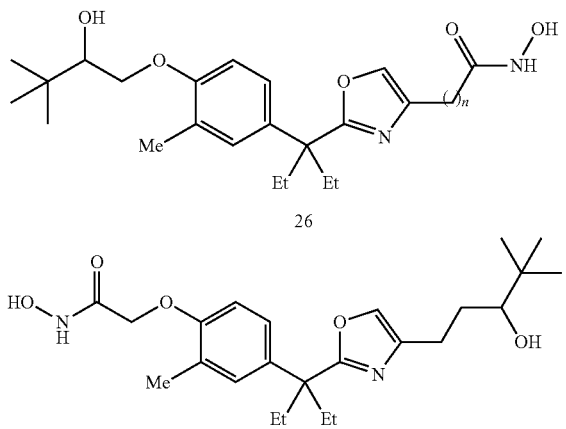

a: n = 1, R = Et
b: n = 2, R = Et
c: n = 3, R = Me

To appropriate ester (1 equiv) in THF:MeOH 1:1 was added $NH_2OH$ (50 wt % solution in water, 500 equiv) and reaction mixture is cooled to 0° C. Then precooled 3M KOH solution (7 equiv) was added dropwise and reaction mixture was stirred for 2 h at 0° C., then for 48 h at room temperature. Acidified to pH=1 by 1M HCl, extracted with EtOAc (3×10 ml), then the combined organic layers were washed with $H_2O$ (5 mL) and dried with $Na_2SO_4$. The solution was concentrated in vacuo and purified by reverse phase C18 silica.

Compound (DK-65) Yield 43% $^1H$ NMR (400 MHz, $CD_3OD$) δ 7.65 (s, 1H), 6.94 (d, J=5.1 Hz, 1H), 6.89 (s, 1H), 6.80 (d, J=8.6 Hz, 1H), 4.11 (d, J=10.0 Hz, 1H), 3.86 (d, J=10.0 Hz, 1H), 3.61 (d, J=7.8 Hz, 1H), 3.37 (s, 2H), 2.23-2.13 (m, 4H), 2.17 (s, 1H, overlap), 0.99 (s, 9H), 0.68 (t, J=6.2 Hz, 6H);

$^{13}C$ NMR (75 MHz, $CD_3OD$) δ, 169.5, 155.7, 135.9, 134.9, 133.4, 128.7, 126.1, 124.9, 110.3, 105.0, 77.2, 69.5, 33.7, 30.1, 27.7, 25.1, 15.3, 7.2;

Purity >95% according to HPLC

Compound (DK-71): Yield 48%; $^1H$ NMR (400 MHz, $CD_3OD$) δ 7.51 (s, 1H), 6.92 (d, J=8.6 Hz, 1H), 6.87 (s, 1H), 6.80 (d, J=8.6 Hz, 1H), 4.11 (d, J=10.0 Hz, 1H), 3.86 (d, J=10.0 Hz, 1H), 3.61 (d, J=10.0 Hz, 1H), 3.34 (s, 2H), 2.83 (t, J=7.3 Hz, 2H), 2.42 (t, J=7.5 Hz, 2H), 2.24-2.14 (m, 4H), 2.18 (s, 3H), 0.99 (s, 9H), 0.68 (t, J=7.4 Hz, 6H);

$^{13}C$ NMR (75 MHz, $CD_3OD$) δ, 161.8, 155.7, 138.2, 135.0, 134.3, 128.7, 126.1, 124.9, 110.3, 106.6, 77.2, 69.5, 33.7, 31.1, 27.6, 25.1, 21.6, 15.3, 7.2;

Purity >95% according to HPLC

Compound (DK-90) Yield 52%; $^1H$ NMR (400 MHz, $CD_3OD$) δ 7.52 (s, 1H), 6.93 (d, J=8.5 Hz, 1H), 6.88 (s, 1H), 6.80 (d, J=8.6 Hz, 1H),), 4.11 (d, J=10.0 Hz, 1H), 3.86 (d, J=9.9, 7.8 Hz, 1H), 3.61 (dd, J=7.7 Hz, 1H), 2.55 (t, J=7.4 Hz, 2H), 2.23-2.09 (m, 6H), 2.17 (s, 3H, overlap), 1.98-1.88 (m, 2H), 0.99 (s, 9H), 0.68 (t, J=7.4 Hz, 6H);

$^{13}C$ NMR (75 MHz, $CD_3OD$) δ 169.5, 155.7, 139.1, 135.0, 134.2, 128.7, 126.1, 124.8, 110.3, 105.0, 77.2, 69.5, 33.7, 31.7, 27.6, 25.1, 24.8, 24.2, 15.4, 7.2;

Purity >95% according to HPLC

HRMS (ESI): m/z calcd for $[(M+H)_+]$=447.2854, found=447.2822.

Compound (DK-91): Yield 48%; $^1H$ NMR (400 MHz, $CD_3OD$) 7.50 (s, 1H), 6.95 (d, J=8.6 Hz, 1H), 6.91 (s, 1H), 6.79 (d, J=8.5 Hz, 1H), 4.52 (s, 2H), 3.11 (d, J=9.5 Hz, 1H), 2.79-2.69 (m, 1H), 2.62-2.51 (m, 1H), 2.26-2.12 (m, 1H), 2.22 (s, 3H, overlap), 1.96-1.86 (m, 1H), 1.59-1.47 (m, 1H), 0.88 (s, 9H), 0.68 (t, J=6.5 Hz, 6H);

$^{13}C$ NMR (75 MHz, $CD_3OD$) δ 169.3, 154.7, 139.7, 136.5, 134.2, 129.1, 126.5, 124.9, 110.9, 77.9, 66.4, 34.5, 29.7, 27.6, 24.9, 22.7, 15.2, 7.1;

Purity >95% according to HPLC

HRMS (ESI): m/z calcd for $[(M+H)_+]$=433.2697, found 433.2666.

Compounds JF-D15 and JF-D50 can be prepared substantially in accordance with methods described herein or by methods known in the art without undue burden and were characterized as follow:

JF-D15 IR (thin film) 3489, 3262, 2961, 2875, 1733, 1503, 1246, 1136 cm−1; 1H NMR (500 MHz, CD3OD) δ 6.98-6.92 (m, 2H), 6.87-6.81 (m, 2H), 6.77-6.71 (m, 2H), 4.11 (dd, J=10.0, 3.0 Hz, 1H), 3.97 (t, J=6.0 Hz, 2H), 3.86 (dd, J=10.0, 7.8 Hz, 1H), 3.61 (dd, J=7.7, 2.9 Hz, 1H), 2.31 (t, J=7.4 Hz, 2H), 2.15 (s, 3H), 2.12 (s, 3H), 2.10-2.06 (m, 2H), 2.03 (q, J=7.2 Hz, 4H), 1.00 (s, 9H), 0.58 (t, J=7.3 Hz, 6H) ppm; 13C NMR (126 MHz, CD3OD) □172.4, 156.3, 156.0, 142.0 (2 coincident peaks), 131.6, 131.5, 127.17, 127.15, 126.8, 126.6, 111.2, 111.1, 78.7, 70.9, 68.0, 49.4, 35.1, 30.5, 30.2, 26.7, 26.6, 16.8, 16.7, 8.8 ppm;

JF-D50 IR (thin film) 3235, 2963, 2938, 2876, 1648, 1503, 1243 cm−1; 1H NMR (300 MHz, CD3OD) δ 7.04-6.82 (m, 5H), 6.74 (d, J=8.5 Hz, 1H), 4.10 (dd, J=10.0, 2.9 Hz, 1H), 3.86 (dd, J=10.0, 7.8 Hz, 1H), 3.61 (dd, J=7.7, 2.9 Hz, 1H), 2.93-2.80 (m, 2H), 2.36-2.27 (m, 2H), 2.24 (s, 3H), 2.14 (s, 3H), 2.05 (q, J=7.4 Hz, 4H), 1.00 (s, 9H), 0.57 (t, J=7.2 Hz, 6H) ppm; 13C NMR (75 MHz, CD3OD) □ 172.2, 156.3, 148.4, 141.7, 136.8, 136.0, 131.5, 131.1, 128.9, 127.2, 126.85, 126.82, 111.2, 78.7, 70.9, 49.7, 35.1, 34.5, 30.0, 29.6, 26.6, 19.6, 16.8, 8.7 ppm;

EXAMPLE 32

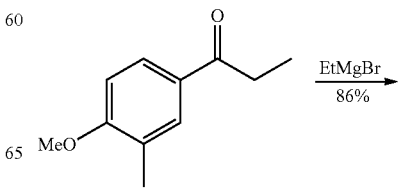

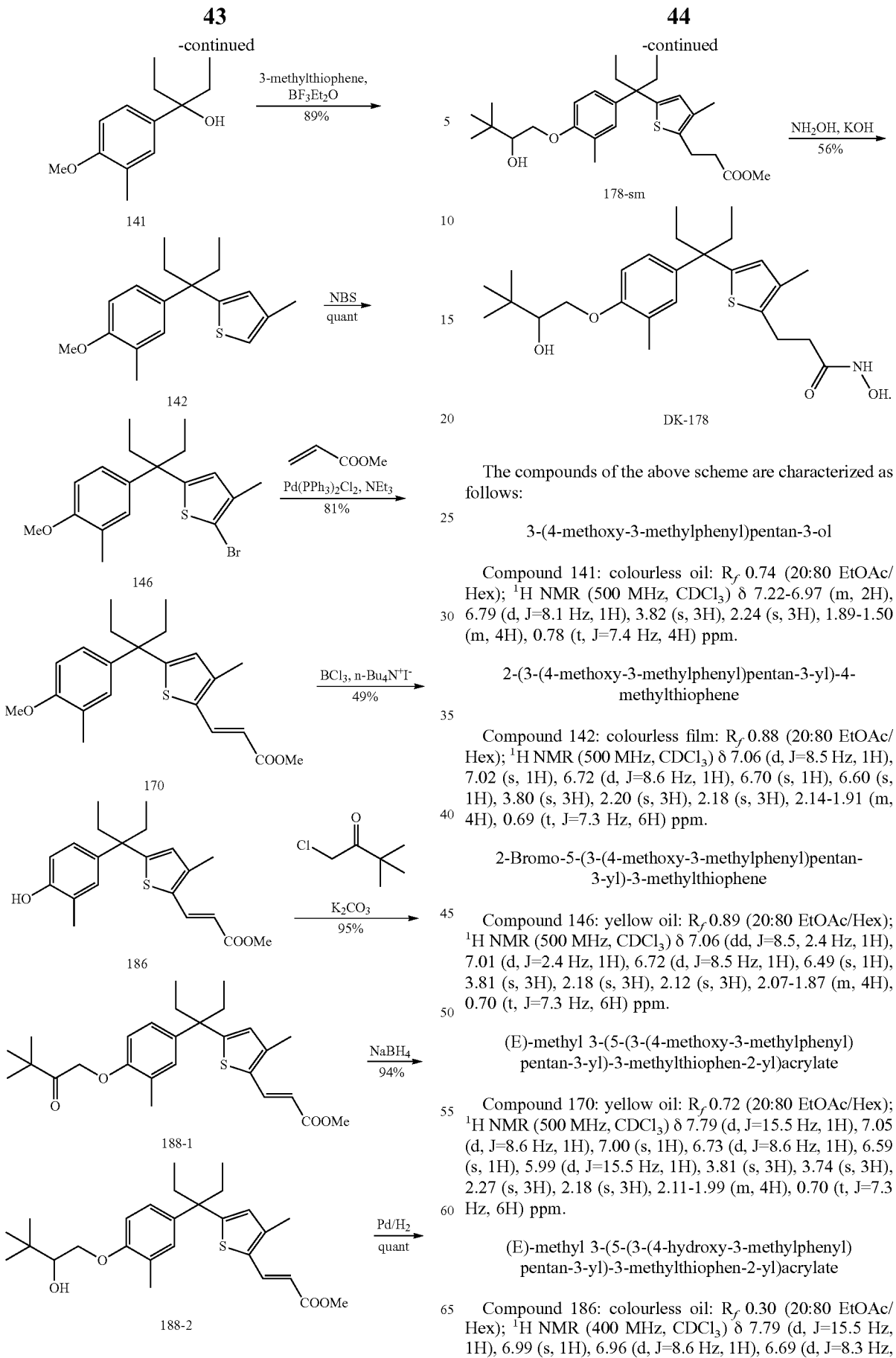

The compounds of the above scheme are characterized as follows:

3-(4-methoxy-3-methylphenyl)pentan-3-ol

Compound 141: colourless oil: $R_f$ 0.74 (20:80 EtOAc/Hex); $^1$H NMR (500 MHz, CDCl$_3$) δ 7.22-6.97 (m, 2H), 6.79 (d, J=8.1 Hz, 1H), 3.82 (s, 3H), 2.24 (s, 3H), 1.89-1.50 (m, 4H), 0.78 (t, J=7.4 Hz, 4H) ppm.

2-(3-(4-methoxy-3-methylphenyl)pentan-3-yl)-4-methylthiophene

Compound 142: colourless film: $R_f$ 0.88 (20:80 EtOAc/Hex); $^1$H NMR (500 MHz, CDCl$_3$) δ 7.06 (d, J=8.5 Hz, 1H), 7.02 (s, 1H), 6.72 (d, J=8.6 Hz, 1H), 6.70 (s, 1H), 6.60 (s, 1H), 3.80 (s, 3H), 2.20 (s, 3H), 2.18 (s, 3H), 2.14-1.91 (m, 4H), 0.69 (t, J=7.3 Hz, 6H) ppm.

2-Bromo-5-(3-(4-methoxy-3-methylphenyl)pentan-3-yl)-3-methylthiophene

Compound 146: yellow oil: $R_f$ 0.89 (20:80 EtOAc/Hex); $^1$H NMR (500 MHz, CDCl$_3$) δ 7.06 (dd, J=8.5, 2.4 Hz, 1H), 7.01 (d, J=2.4 Hz, 1H), 6.72 (d, J=8.5 Hz, 1H), 6.49 (s, 1H), 3.81 (s, 3H), 2.18 (s, 3H), 2.12 (s, 3H), 2.07-1.87 (m, 4H), 0.70 (t, J=7.3 Hz, 6H) ppm.

(E)-methyl 3-(5-(3-(4-methoxy-3-methylphenyl)pentan-3-yl)-3-methylthiophen-2-yl)acrylate Compound 170: yellow oil: $R_f$ 0.72 (20:80 EtOAc/Hex); $^1$H NMR (500 MHz, CDCl$_3$) δ 7.79 (d, J=15.5 Hz, 1H), 7.05 (d, J=8.6 Hz, 1H), 7.00 (s, 1H), 6.73 (d, J=8.6 Hz, 1H), 6.59 (s, 1H), 5.99 (d, J=15.5 Hz, 1H), 3.81 (s, 3H), 3.74 (s, 3H), 2.27 (s, 3H), 2.18 (s, 3H), 2.11-1.99 (m, 4H), 0.70 (t, J=7.3 Hz, 6H) ppm.

(E)-methyl 3-(5-(3-(4-hydroxy-3-methylphenyl)pentan-3-yl)-3-methylthiophen-2-yl)acrylate Compound 186: colourless oil: $R_f$ 0.30 (20:80 EtOAc/Hex); $^1$H NMR (400 MHz, CDCl$_3$) δ 7.79 (d, J=15.5 Hz, 1H), 6.99 (s, 1H), 6.96 (d, J=8.6 Hz, 1H), 6.69 (d, J=8.3 Hz, 1H), 6.58 (s, 1H), 5.99 (d, J=15.5 Hz, 1H), 4.99 (bs, 1H), 3.75 (s, 3H), 2.26 (s, 3H), 2.22 (s, 3H), 2.17-1.70 (m, 4H), 0.69 (t, J=7.3 Hz, 6H) ppm.

(E)-methyl 3-(5-(3-(4-(3,3-dimethyl-2-oxobutoxy)-3-methylphenyl)pentan-3-yl)-3-methylthiophen-2-yl)acrylate Compound 188-1: colourless oil: R$_f$ 0.73 (20:80 EtOAc/Hex); $^1$H NMR (500 MHz, CDCl$_3$) δ 7.78 (d, J=15.5 Hz, 1H), 7.03 (s, 1H), 6.99 (d, J=8.5 Hz, 1H), 6.57 (s, 1H), 6.52 (d, J=8.6 Hz, 1H), 5.99 (d, J=15.5 Hz, 1H), 4.84 (s, 2H), 3.75 (s, 3H), 2.26 (s, 6H), 2.13-1.92 (m, 4H), 1.25 (s, 9H), 0.69 (t, J=7.3 Hz, 6H) ppm.

E)-methyl 3-(5-(3-(4-(2-hydroxy-3,3-dimethylbutoxy)-3-methylphenyl)pentan-3-yl)-3-methylthiophen-2-yl)acrylate Compound 188-2: colourless oil: R$_f$ 0.76 (20:80 EtOAc/Hex); $^1$H NMR (300 MHz, CDCl$_3$) δ 7.79 (d, J=15.5 Hz, 1H), 7.08-6.99 (m, 2H), 6.73 (d, J=7.4 Hz, 1H), 6.58 (s, 1H), 5.98 (d, J=15.5 Hz, 1H), 4.09 (d, J=9.0 Hz, 1H), 3.86 (t, J=9.6 Hz, 1H), 3.78-3.64 (m, 4H), 2.26 (s, 3H), 2.20 (s, 3H), 2.13-1.98 (m, 4H), 1.01 (s, 9H), 0.70 (t, J=6.7 Hz, 6H) ppm.

Methyl 3-(5-(3-(4-(2-hydroxy-3,3-dimethylbutoxy)-3-methylphenyl)pentan-3-yl)-3-methylthiophen-2-yl)propanoate Compound 178-sm: colourless oil: R$_f$ 0.77 (20:80 EtOAc/Hex); $^1$H NMR (400 MHz, CDCl$_3$) δ 7.09-6.99 (m, 2H), 6.71 (d, J=8.2 Hz, 1H), 6.46 (s, 1H), 4.09 (dd, J=9.1, 2.5 Hz, 1H), 3.86 (t, J=8.9 Hz, 1H), 3.77-3.67 (m, 1H), 3.65 (s, 3H), 2.96 (t, J=7.8 Hz, 2H), 2.56 (t, J=7.8 Hz, 2H), 2.19 (s, 3H), 2.09 (s, 3H), 2.08-1.96 (m, 4H), 1.01 (s, 9H), 0.68 (t, J=7.3 Hz, 6H) ppm.

N-hydroxy-3-(5-(3-(4-(2-hydroxy-3,3-dimethylbutoxy)-3-methylphenyl)pentan-3-yl)-3-methylthiophen-2-yl)propanamide Compound DK-178: colourless film: $^1$H NMR (400 MHz, CD$_3$OD) δ 7.03 (d, J=9.0 Hz, 1H), 6.98 (s, 1H), 6.76 (d, J=8.7 Hz, 1H), 6.49 (s, 1H), 4.11 (d, J=8.8 Hz, 1H), 3.90-3.81 (m, 1H), 3.62 (d, J=5.7 Hz, 1H), 2.94 (t, J=7.7 Hz, 2H), 2.29 (t, 7.6 Hz, 2H), 2.17 (s, 3H), 2.09 (s, 3H), 2.06-1.90 (m, 4H), 1.00 (s, 9H), 0.66 (t, J=7.2 Hz, 6H) ppm; $^{13}$C NMR (75 MHz, CD$_3$OD) δ 171.6, 155.2, 150.9, 139.2, 133.7, 131.6, 129.5, 126.9, 125.5, 125.2, 109.8, 77.2, 69.5, 60.1, 34.2, 33.7, 30.1, 25.2, 23.4, 19.4, 15.4, 13.0, 12.3, 7.3 ppm; HRMS (ESI) Calc. for C$_{24}$H$_{38}$O$_4$NS [M−H]$^-$: 460.25270, found: 460.25346; LRMS (ESI) m/z 462.4 [M+H]$^+$;

EXAMPLE 33

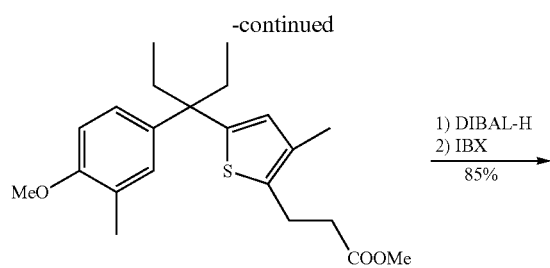
196

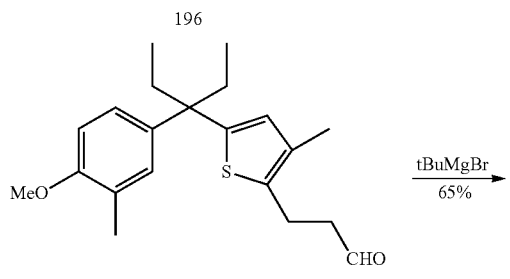
179

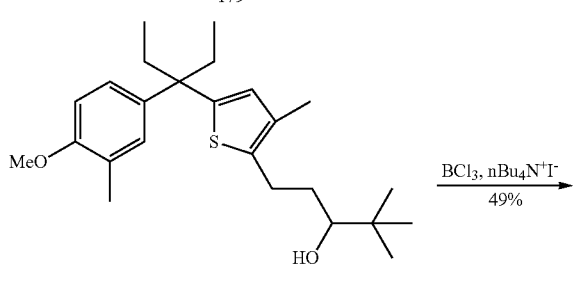
180

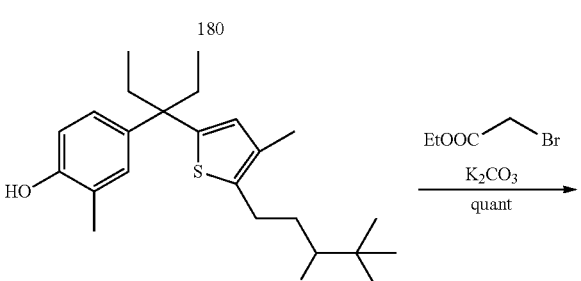
183

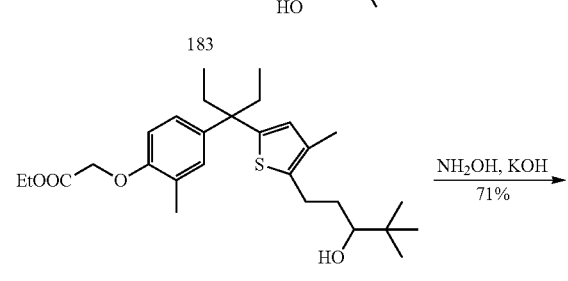
200

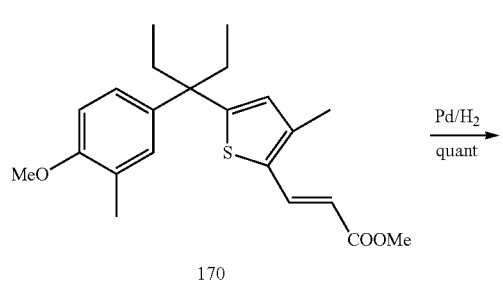
170

DK-201

The compounds of the above scheme are characterized as follows:

Methyl 3-(5-(3-(4-methoxy-3-methylphenyl)pentan-3-yl)-3-methylthiophen-2-yl)propanoate Compound 196: colourless oil: $R_f$ 0.79 (20:80 EtOAc/Hex); $^1$H NMR (400 MHz, CDCl$_3$) δ 7.06 (dd, J=8.5, 2.4 Hz, 1H), 7.02 (s, 1H), 6.71 (d, J=8.5 Hz, 1H), 6.46 (s, 1H), 3.80 (s, 3H), 3.65 (s, 3H), 3.00 (t, J=7.8 Hz, 2H), 2.56 (t, J=7.8 Hz, 2H), 2.17 (s, 3H), 2.09 (s, 3H), 2.07-1.92 (m, 4H), 0.68 (t, J=7.3 Hz, 6H) ppm.

3-(5-(3-(4-methoxy-3-methylphenyl)pentan-3-yl)-3-methylthiophen-2-yl)propanal

Compound 179: yellow oil: $R_f$ 0.60 (20:80 EtOAc/Hex); $^1$H NMR (300 MHz, CDCl$_3$) δ 9.78 (s, 1H), 7.06 (d, J=8.4 Hz, 1H), 7.02 (s, 1H), 6.72 (d, J=8.4 Hz, 1H), 6.47 (s, 1H), 3.81 (s, 3H), 2.97 (t, J=7.5 Hz, 2H), 2.72 (t, J=6.9 Hz, 2H), 2.18 (s, 3H), 2.10 (s, 3H), 2.06-1.95 (m, 4H), 0.68 (t, J=7.3 Hz, 6H) ppm.

1-(5-(3-(4-methoxy-3-methylphenyl)pentan-3-yl)-3-methylthiophen-2-yl)-4,4-dimethylpentan-3-ol Compound 180: colourless oil: $R_f$ 0.77 (20:80 EtOAc/Hex); $^1$H NMR (400 MHz, CDCl$_3$) δ 7.07 (d, J=8.2 Hz, 1H), 7.03 (s, 1H), 6.72 (d, J=8.4 Hz, 1H), 6.48 (s, 1H), 3.80 (s, 3H), 3.18 (m, 1H), 3.01-2.82 (m, 1H), 2.80-2.61 (m, 1H), 2.18 (s, 3H), 2.10 (s, 3H), 2.07-1.96 (m, 4H), 1.86-1.74 (m, 1H), 1.50 (m, 1H), 0.89 (s, 9H), 0.69 (t, J=7.3 Hz, 6H) ppm.

4-3-(5-(3-hydroxy-4,4-dimethylpentyl)-4-methylthiophen-2-yl)pentan-3-yl)-2-methylphenol Compound 183: yellow film: $R_f$ 0.24 (20:80 EtOAc/Hex); $^1$H NMR (400 MHz, CDCl$_3$) δ 7.02 (s, 1H), 6.98 (dd, J=8.4, 2.2 Hz, 1H), 6.67 (d, J=8.3 Hz, 1H), 6.48 (s, 1H), 4.64 (bs, 1H), 3.19 (m, 1H), 2.90 (m, 1H), 2.68 (m, 1H), 2.21 (s, 3H), 2.09 (s, 3H), 2.06-1.97 (m, 4H), 1.85-1.70 (m, 1H), 1.55-1.45 (m, 1H), 0.87 (s, 9H), 0.69 (t, J=7.3 Hz, 6H) ppm.

Ethyl 2-(4-(3-(5-(3-hydroxy-4,4-dimethylpentyl)-4-methylthiophen-2-yl)pentan-3-yl)-2-methylphenoxy)acetate Compound 200: colourless film: $R_f$ 0.69 (20:80 EtOAc/Hex); $^1$H NMR (400 MHz, CDCl$_3$) δ 7.05 (s, 1H), 7.01 (d, J=2.3 Hz, 1H), 6.59 (d, J=8.4 Hz, 1H), 6.47 (s, 1H), 4.60 (s, 2H), 4.26 (q, J=7.2 Hz, 2H), 3.22-3.14 (m, 1H), 2.94-2.87 (m, 1H), 2.74-2.65 (m, 1H), 2.25 (s, 3H), 2.09 (s, 3H), 2.07-1.94 (m, 4H), 1.84-1.70 (m, 1H), 1.62-1.47 (m, 1H), 1.41-1.15 (t, J=7.2 Hz, 3H), 0.87 (s, 9H), 0.68 (t, J=7.3 Hz, 6H) ppm.

N-hydroxy-2-4-3-5-3-hydroxy-4,4-dimethylpentyl)-4-methlthiophen-2-yl)pentan-3-yl)-2-methylphenoxy)acetamide Compound DK-201: colourless film: $^1$H NMR (400 MHz, CD$_3$OD) δ 7.06 (d, J=8.8 Hz, 1H), 7.02 (s, 1H), 6.74 (d, J=8.5 Hz, 1H), 6.49 (s, 1H), 4.52 (s, 2H), 3.11 (d, J=9.3 Hz, 1H), 2.91-2.81 (m, 1H), 2.74-2.60 (m, 1H), 2.21 (s, 3H), 2.09 (s, 3H), 2.07-1.95 (m, 4H), 1.74 (m, 1H), 1.55-1.42 (m, 1H), 0.84 (s, 9H), 0.66 (t, J=7.3 Hz, 6H) ppm; $^{13}$C NMR (75 MHz, CD$_3$OD) δ 166.8, 154.1, 149.8, 140.8, 136.1, 130.8, 129.9, 126.8, 125.9, 125.3, 110.4, 78.1, 66.4, 34.4, 32.9, 30.0, 24.9, 24.7, 15.3, 12.4, 7.3 ppm; HRMS (ESI) Calc. for C$_{26}$H$_{38}$O$_4$NS [M−H]$^-$: 460.25270, found: 460.25305;

EXAMPLE 34

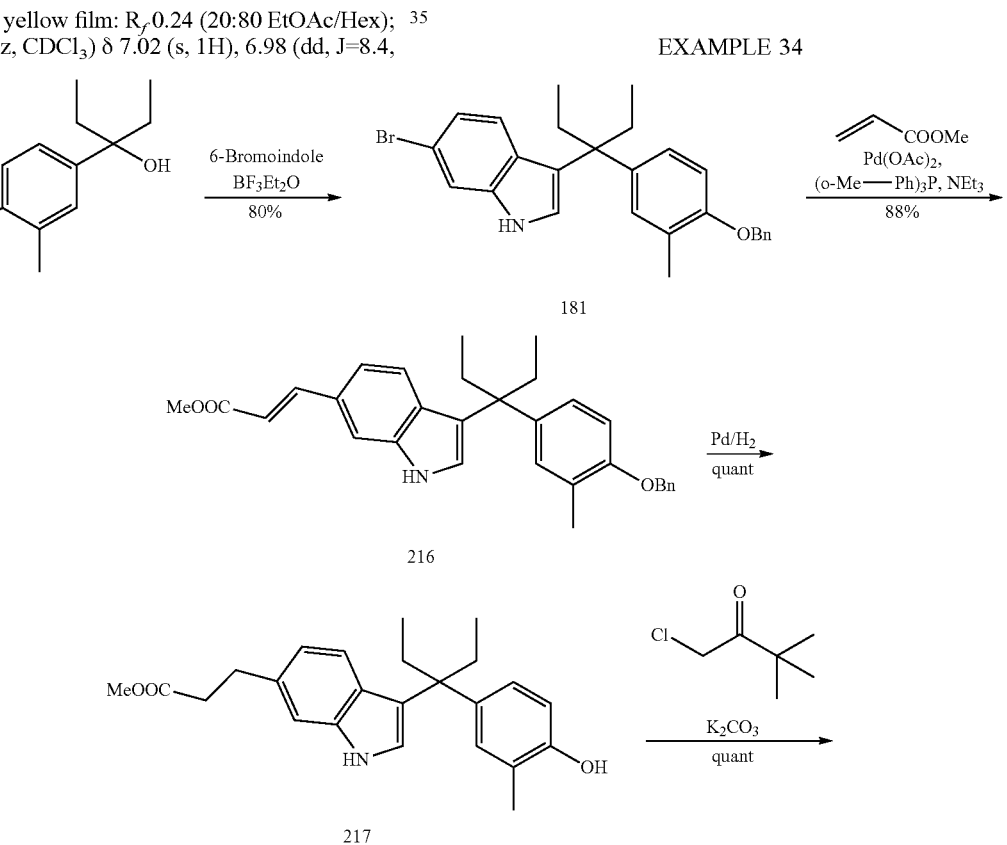

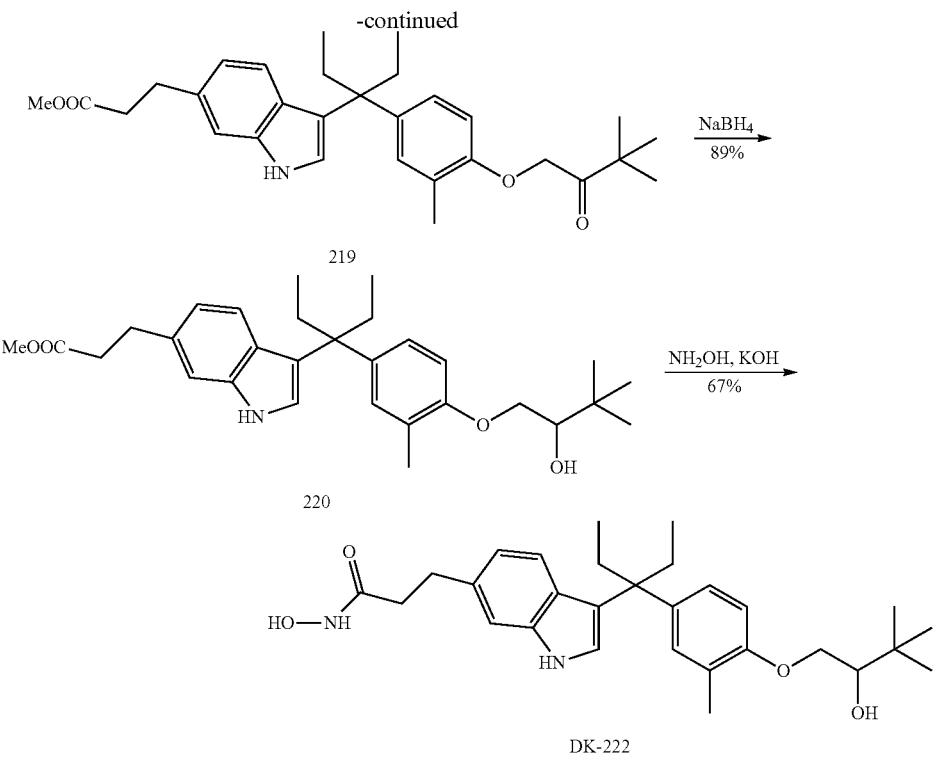

The compounds of the above scheme are characterized as follows:

3-(3-(4-(benzyloxy)-3-methylphenyl)pentan-3-yl)-6-bromo-1H-indole

Compound 181: colourless oil: R$_f$ 0.64 (20:80 EtOAc/Hex); $^1$H NMR (400 MHz, CDCl$_3$) δ 7.93 (bs, 1H), 7.50-7.40 (m, 3H), 7.38 (t, J=7.3 Hz, 2H), 7.31 (t, J=7.2 Hz, 1H), 7.13 (d, J=2.4 Hz, 1H), 7.03 (s, 1H), 7.01 (d, J=2.3 Hz, 1H), 6.91 (dd, J=8.6, 1.7 Hz, 1H), 6.76 (d, J=8.8 Hz, 2H), 5.03 (s, 2H), 2.20 (s, 3H), 2.15-1.97 (m, 4H), 0.63 (t, J=7.3 Hz, 6H) ppm.

(E)-methyl 3-(3-(3-(4-(benzyloxy)-3-methylphenyl)pentan-3-yl)-1H-indol-6-yl)acrylate Compound 216: colourless oil: R$_f$ 0.71 (20:80 EtOAc/Hex); $^1$H NMR (400 MHz, CDCl$_3$) δ 8.17 (bs, 1H), 7.75 (d, J=15.9 Hz, 1H), 7.44 (m, 3H), 7.37 (t, J=7.3 Hz, 2H), 7.31 (t, J=7.2 Hz, 1H), 7.24 (d, J=2.5 Hz, 1H), 7.13-6.98 (m, 3H), 6.91 (d, J=8.4 Hz, 1H), 6.76 (d, J=8.4 Hz, 1H), 6.36 (d, J=15.9 Hz, 1H), 5.03 (s, 2H), 3.79 (s, 3H), 2.22 (s, 3H), 2.16-1.94 (m, 4H), 0.63 (t, J=7.3 Hz, 6H) ppm.

Methyl 3-(3-(3-(4-hydroxy-3-methylphenyl)pentan-3-yl)-1H-indol-6-yl)propanoate

Compound 217: yellow oil: R$_f$ 0.15 (20:80 EtOAc/Hex); $^1$H NMR (400 MHz, CDCl$_3$) δ 7.87 (bs, 1H), 7.13 (s, 1H), 7.09 (d, J=2.4 Hz, 1H), 7.04 (d, J=1.8 Hz, 1H), 6.96 (dd, J=8.3, 2.4 Hz, 1H), 6.83 (d, J=8.2 Hz, 1H), 6.65 (dd, J=8.2, 1.5 Hz, 1H), 6.62 (d, J=8.3 Hz, 1H), 4.58 (bs, 1H), 3.66 (s, 3H), 2.97 (t, J=7.8 Hz, 2H), 2.63 (t, J=7.8 Hz, 2H), 2.18 (s, 3H), 2.16-1.83 (m, 4H), 0.62 (t, J=7.3 Hz, 6H)ppm.

Methyl 3-(3-(3-(4-(3,3-dimethyl-2-oxobutoxy)-3-methylphenyl)pentan-3-yl)-1H-indol-6-yl)propanoate Compound 219: yellow oil: R$_f$ 0.55 (20:80 EtOAc/Hex); $^1$H NMR (400 MHz, CDCl$_3$) δ 7.91 (bs, 1H), 7.13 (s, 1H), 7.10-7.06 (m, 2H), 7.00 (dd, J=8.5, 2.3 Hz, 1H), 6.81 (d, J=8.2 Hz, 1H), 6.64 (dd, J=8.3, 1.5 Hz, 1H), 6.50 (d, J=8.5 Hz, 1H), 4.81 (s, 2H), 3.67 (s, 3H), 2.97 (t, J=7.8 Hz, 2H), 2.63 (t, J=7.8 Hz, 2H), 2.23 (s, 3H), 2.15-1.88 (m, 4H), 1.24 (s, 9H), 0.61 (t, J=7.3 Hz, 6H) ppm.

Methyl 3-(3-(3-(4-(2-hydroxy-3,3-dimethylbutoxy)-3-methylphenyl)pentan-3-yl)-1H-indol-6-yl)propanoate Compound 220 colourless oil: R$_f$ 0.52 (20:80 EtOAc/Hex); $^1$H NMR (400 MHz, CDCl$_3$) δ 7.88 (bs, 1H), 7.13 (s, 1H), 7.10 (d, J=2.4 Hz, 1H), 7.07-7.00 (m, 2H), 6.82 (d, J=8.2 Hz, 1H), 6.72-6.62 (m, 2H), 4.07 (dd, J=9.1, 2.6 Hz, 1H), 3.83 (t, J=9.0 Hz, 1H), 3.70 (dt, J=8.8, 2.6 Hz, 1H), 3.66 (s, 3H), 2.97 (t, J=7.8 Hz, 2H), 2.63 (t, J=7.8 Hz, 2H), 2.16 (s, 3H), 2.16-1.93 (m, 4H), 1.00 (s, 9H), 0.62 (t, J=7.3 Hz, 6H) ppm.

N-hydroxy-3-(3-3-4-(2-hydroxy-3-dimethylbutoxy-3-methylphenyl)pentan-3-yl)-1H-indol-6-yl)propanamide Compound DK-222: colourless film; $^1$H NMR (400 MHz, CD$_3$OD) δ 7.12 (m, 2H), 7.05 (dd, J=8.5, 2.3 Hz, 1H), 6.99 (d, J=2.1 Hz, 1H), 6.75-6.69 (m, 2H), 6.54 (dd, J=8.3, 1.4 Hz, 1H), 4.09 (dd, J=10.0, 2.9 Hz, 1H), 3.85 (dd, J=10.0, 7.9 Hz, 1H), 3.61 (dd, J=7.8, 2.8 Hz, 1H), 2.90 (t, J=7.6 Hz, 2H), 2.34 (t, J=7.6 Hz, 2H), 2.12 (s, 3H), 2.24-1.98 (m, 4H), 0.99 (s, 9H), 0.60 (t, J=7.3 Hz, 6H) ppm; $^{13}$C NMR (75 MHz, CD$_3$OD) δ 170.7, 154.8, 139.8, 137.7, 132.9, 129.8, 125.5, 125.2, 124.6, 122.1, 121.9, 120.6, 118.1, 110.1, 109.7, 77.3, 69.4, 44.8, 35.1, 33.7, 31.6, 28.2, 25.2, 15.4, 7.3 ppm; HRMS (ESI) Calc. for C$_{29}$H$_{39}$O$_4$N$_2$ [M-H]$^-$: 479.29153, found: 479.29230.

EXAMPLE 35
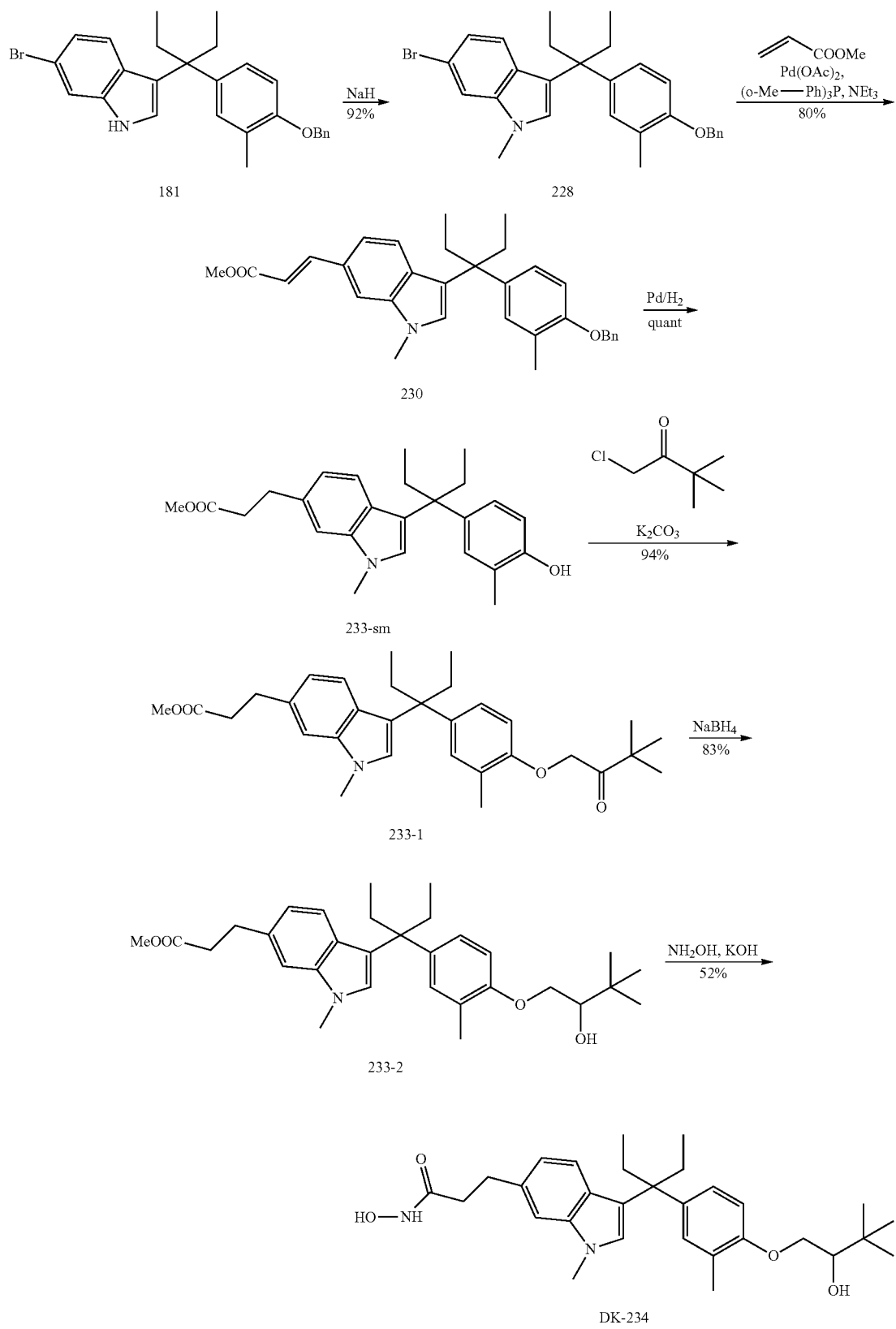

The compounds of the above scheme are characterized as follows:

3-(3-(4-(benzyloxy)-3-methylphenyl)pentan-3-yl)-6-bromo-1-methyl-1H-indole

Compound 228: colourless oil: $R_f$ 0.75 (20:80 EtOAc/Hex); $^1$H NMR (400 MHz, CDCl$_3$) δ 7.45-7.29 (m, 6H), 7.06-7.00 (m, 2H), 6.96 (s, 1H), 6.89 (dd, J=8.5, 1.7 Hz, 1H), 6.78-6.73 (m, 2H), 5.03 (s, 2H), 3.75 (s, 3H), 2.21 (s, 3H), 2.15-1.88 (m, 4H), 0.63 (t, J=7.3 Hz, 6H) ppm.

(E)-methyl 3-(3-(3-(4-(benzyloxy)-3-methylphenyl)pentan-3-yl)-1-methyl-1H-indol-6-yl)acrylate Compound 230: colourless oil: $R_f$ 0.70 (20:80 EtOAc/Hex); $^1$H NMR (300 MHz, CDCl$_3$) δ 7.79 (d, J=15.9 Hz, 1H), 7.58-7.28 (m, 6H), 7.12-6.96 (m, 4H), 6.90 (d, J=8.4 Hz, 1H), 6.76 (d, J=8.2 Hz, 1H), 6.39 (d, J=15.9 Hz, 1H), 5.03 (s, 2H), 3.82 (s, 3H), 2.79 (s, 3H), 2.21 (s, 3H), 2.17-1.91 (m, 4H), 0.64 (t, J=7.3 Hz, 6H) ppm.

Methyl 3-(3-(3-(4-hydroxy-3-methylphenyl)pentan-3-yl)-1-methyl-1H-indol-6-yl)propanoate Compound 233-sm: yellow oil: $R_f$ 0.16 (20:80 EtOAc/Hex); $^1$H NMR (400 MHz, CDCl$_3$) δ 7.07-7.01 (m, 2H), 6.95 (dd, J=8.0, 2.1 Hz, 1H), 6.92 (s, 1H), 6.82 (d, J=8.2 Hz, 1H), 6.66 (d, J=8.2 Hz, 1H), 6.63 (d, J=8.2 Hz, 1H), 5.24 (bs, 1H), 3.74 (s, 3H), 3.66 (s, 3H), 3.00 (t, J=7.8 Hz, 2H), 2.65 (t, J=7.8 Hz, 2H), 2.17 (s, 3H), 2.13-1.90 (m, 4H), 0.61 (t, J=7.3 Hz, 6H) ppm.

Methyl 3-(3-(3-(4-(3,3-dimethyl-2-oxobutoxy)-3-methylphenyl)pentan-3-yl)-1-methyl-1H-indol-6-yl)propanoate Compound 233-1: colourless oil: $R_f$ 0.58 (20:80 EtOAc/Hex); $^1$H NMR (300 MHz, CDCl$_3$) δ 7.08 (d, J=2.0 Hz, 1H), 7.05 (s, 1H), 7.00 (dd, J=8.5, 2.2 Hz, 1H), 6.92 (s, 1H), 6.80 (d, J=8.2 Hz, 1H), 6.63 (dd, J=8.2, 1.4 Hz, 1H), 6.49 (d, J=8.5 Hz, 1H), 4.81 (s, 2H), 3.75 (s, 3H), 3.67 (s, 3H), 3.00 (t, J=7.8 Hz, 2H), 2.64 (t, J=7.8 Hz, 2H), 2.23 (s, 3H), 2.17-1.87 (m, 4H), 1.24 (s, 9H), 0.61 (t, J=7.3 Hz, 6H) ppm.

Methyl 3-(3-(3-(4-(2-hydroxy-3,3-dimethylbutoxy)-3-methylphenyl)pentan-3-yl)-1-methyl-1H-indol-6-yl)propanoate Compound 233-2 colourless oil: $R_f$ 0.56 (20:80 EtOAc/Hex); $^1$H NMR (300 MHz, CDCl$_3$) δ 7.12-7.00 (m, 3H), 6.93 (s, 1H), 6.81 (d, J=8.2 Hz, 1H), 6.72-6.57 (m, 2H), 4.07 (dd, J=9.1, 2.6 Hz, 1H), 3.83 (t, J=8.9 Hz, 1H), 3.76 (s, 3H), 3.70-3.67 (m, 1H), 3.67 (s, 3H), 2.65 (t, J=7.8 Hz, 2H), 2.77-2.57 (t, J=7.8 Hz, 2H), 2.16 (s, 3H), 2.13-1.91 (m, 4H), 1.00 (s, 9H), 0.62 (t, J=7.3 Hz, 6H) ppm.

N-hydroxy-3-(3-(3-(4-(2-hydroxy-3,3-dimethylbutoxy)-3-methylphenyl)pentan-3-yl)-1-methyl-1H-indol-6-yl)propanamide Compound DK-234: colourless film; $^1$H NMR (400 MHz, CD$_3$OD) δ 7.09 (s, 1H), 7.07-7.03 (m, 2H), 6.98 (s, 1H), 6.72 (d, J=4.8 Hz, 1H), 6.70 (d, J=4.5 Hz, 1H), 6.56 (d, J=8.2 Hz, 1H), 4.09 (dd, J=10.0, 2.9 Hz, 1H), 3.84 (dd, J=10.0, 7.9 Hz, 1H), 3.76 (s, 3H), 3.61 (dd, J=7.8, 2.8 Hz, 1H), 2.93 (t, J=7.5 Hz, 2H), 2.36 (t, J=7.5 Hz, 2H), 2.22-1.98 (m, 4H), 2.08 (s, 3H), 0.99 (s, 9H), 0.59 (t, J=7.3 Hz, 6H). $^{13}$C NMR (75 MHz, CD$_3$OD) δ 170.9, 154.9, 139.7, 138.1, 133.2, 129.8, 126.7, 125.5, 125.2, 125.1, 121.6, 120.9, 118.2, 109.7, 108.1, 77.3, 69.4, 44.9, 35.0, 33.6, 31.7, 31.3, 28.2, 25.2, 15.4, 7.3 ppm; LRMS (ESI) m/z 495.4 [M+H]$^+$.

EXAMPLE 36

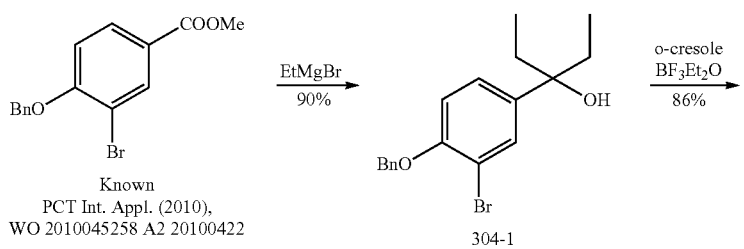

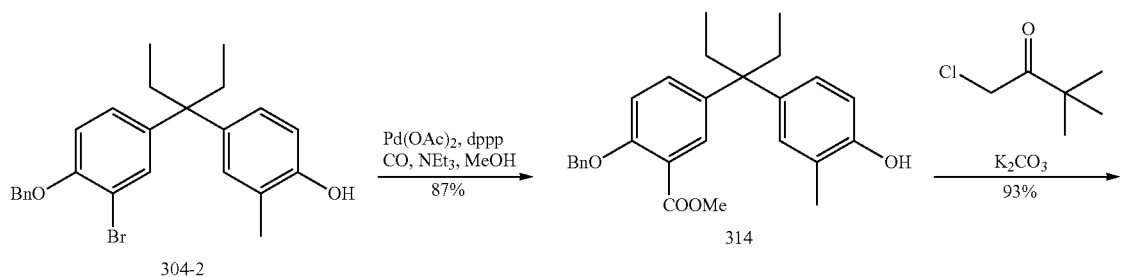

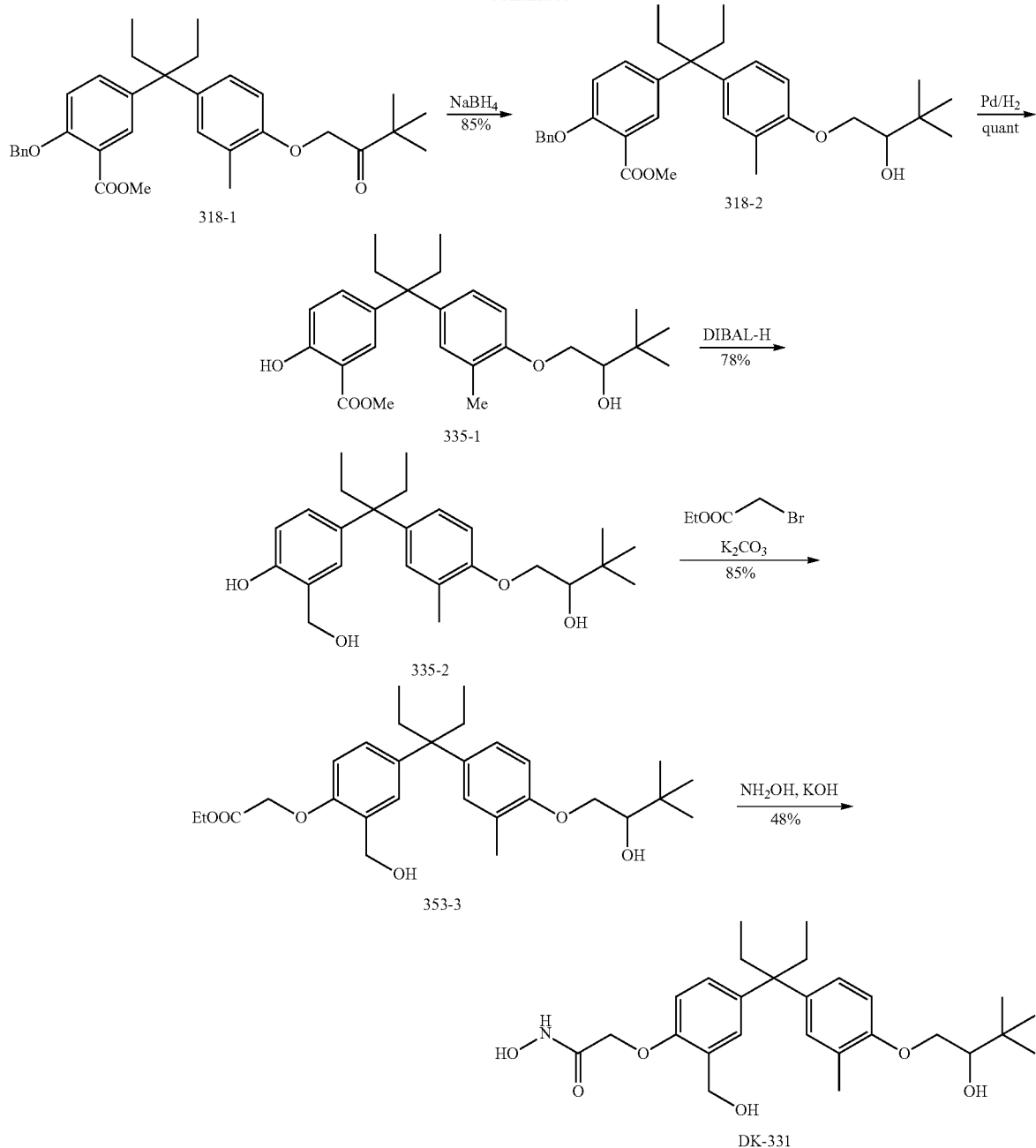

The compounds of the above scheme are characterized as follows:

3-(4-(benzyloxy)-3-bromophenyl)pentan-3-ol

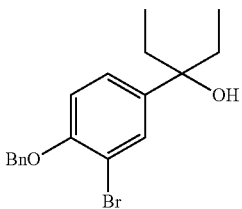 [SMILES: CCC(O)(CC)c1ccc(OCc2ccccc2)c(Br)c1]

Compound 304-1: colourless oil: $R_f$ 0.80 (20:80 EtOAc/Hex); $^1$H NMR (400 MHz, CDCl$_3$) δ 7.58 (d, J=2.2 Hz, 1H), 7.49 (d, J=7.4 Hz, 2H), 7.39 (t, J=7.4 Hz, 2H), 7.32 (t, J=7.3 Hz, 1H), 7.22 (dd, J=8.6, 2.3 Hz, 1H), 6.90 (d, J=8.6 Hz, 1H), 5.15 (s, 2H), 2.05 (s, 1H), 1.94-1.59 (m, 4H), 0.76 (t, J=7.4 Hz, 6H) ppm.

4-(3-(4-(benzyloxy)-3-bromophenyl)pentan-3-yl)-2-methylphenol

Compound 304-2: yellow oil: $R_f$ 0.49 (20:80 EtOAc/Hex); $^1$H NMR (400 MHz, CDCl$_3$) δ 7.47 (d, J=7.2 Hz, 2H), 7.41-7.36 (m, 3H), 7.32 (d, J=7.1 Hz, 1H), 7.00 (dd, J=8.6, 2.3 Hz, 1H), 6.87-6.83 (m, 2H), 6.82 (d, J=8.6 Hz, 1H), 6.65

(d, J=7.9 Hz, 1H), 5.11 (s, 2H), 4.48 (bs, 1H), 2.18 (s, 3H), 2.00 (q, J=7.3 Hz, 4H), 0.60 (t, J=7.3 Hz, 6H) ppm.

Methyl 2-(benzyloxy)-5-(3-(4-hydroxy-3-methylphenyl)pentan-3-yl)benzoate

Compound 314: colourless oil: $R_f$ 0.22 (20:80 EtOAc/Hex); $^1$H NMR (400 MHz, CDCl$_3$) δ 7.70 (s, 1H), 7.48 (d, J=7.3 Hz, 2H), 7.38 (t, J=7.3 Hz, 2H), 7.33-7.27 (m, 1H), 7.16 (d, J=8.6 Hz, 1H), 6.94-6.77 (m, 3H), 6.65 (d, J=8.6 Hz, 1H), 5.14 (s, 2H), 4.72 (bs, 1H), 3.89 (s, 3H), 2.18 (s, 3H), 2.10-1.88 (m, 4H), 0.60 (t, J=6.8 Hz, 6H) ppm.

Methyl 2-(benzyloxy)-5-(3-(4-(3,3-dimethyl-2-oxobutoxy)-3-methylphenyl)pentan-3-yl)benzoate Compound 318-1: colourless oil: $R_f$ 0.50 (20:80 EtOAci-Hex); $^1$H NMR (400 MHz, CDCl$_3$) δ 7.69 (d, J=2.5 Hz, 1H), 7.49 (d, J=8.3 Hz, 2H), 7.38 (t, J=7.8 Hz, 2H), 7.30 (t, J=6.5 Hz, 1H), 7.14 (dd, J=8.7, 2.6 Hz, 1H), 6.95-6.82 (m, 3H), 6.49 (d, J=9.2 Hz, 1H), 5.14 (s, 2H), 4.85 (s, 2H), 3.88 (s, 3H), 2.23 (s, 3H), 2.04 (q, J=7.3 Hz, 4H), 1.25 (s, 9H), 0.59 (t, J=7.3 Hz, 6H) ppm.

Methyl 2-(benzyloxy)-5-(3-(4-(2-hydroxy-3,3-dimethylbutoxy)-3-methylphenyl)pentan-3-yl)benzoate Compound 318-2: yellow film: $R_f$ 0.47 (20:80 EtOAc/Hex); $^1$H NMR (400 MHz, CDCl$_3$) δ 7.69 (d, J=2.5 Hz, 1H), 7.48 (d, J=7.0 Hz, 2H), 7.38 (t, J=7.3 Hz, 2H), 7.30 (t, J=7.1 Hz, 1H), 7.15 (dd, J=8.8, 2.5 Hz, 1H), 6.94 (dd, J=8.5, 2.1 Hz, 1H), 6.88 (m, 2H), 6.70 (d, J=8.5 Hz, 1H), 5.14 (s, 2H), 4.09 (dd, J=9.2, 2.6 Hz, 1H), 3.88 (s, 3H), 3.85 (m, 1H), 3.70 (dd, J=8.7, 2.6 Hz, 1H), 2.16 (s, 3H), 2.05 (q, J=7.2 Hz, 4H), 1.01 (s, 9H), 0.60 (t, J=7.3 Hz, 6H) ppm.

Methyl 2-hydroxy-5-(3-(4-(2-hydroxy-3,3-dimethylbutoxy)-3-methylphenyl)pentan-3-yl)benzoate Compound 335-1: colourless oil: $R_f$ 0.12 (20:80 EtOAc/Hex); $^1$H NMR (500 MHz, CDCl$_3$) δ 7.74 (d, J=2.5 Hz, 1H), 7.14 (d, J=2.5 Hz, 1H), 6.94 (dd, J=8.5, 2.4 Hz, 1H), 6.86 (d, J=2.3 Hz, 1H), 6.84 (d, J=8.6 Hz, 1H), 6.70 (d, J=8.6 Hz, 1H), 4.09 (dd, J=9.2, 2.7 Hz, 1H), 3.94 (s, 3H), 3.85 (t, J=9.0 Hz, 1H), 3.70 (dt, J=8.7, 2.7 Hz, 1H), 2.17 (s, 3H), 2.12-1.79 (m, 4H), 1.00 (s, 9H), 0.61 (t, J=7.3 Hz, 6H) ppm.

4-(3-(4-(2-hydroxy-3-dimethylbutoxy)-3-methylphenyl)pentan-3-yl)-2-(hydroxymethyl)phenol Compound 335-2: colourless oil: $R_f$ 0.51 (40:60 EtOAc/Hex); $^1$H NMR (400 MHz, CDCl$_3$) δ 7.02 (dd, J=8.5, 2.4 Hz, 1H), 6.94 (dd, J=8.5, 2.3 Hz, 1H), 6.88 (d, J=1.9 Hz, 1H), 6.85-6.75 (m, 2H), 6.69 (d, J=8.5 Hz, 1H), 4.80 (s, 2H), 4.08 (dd, J=9.2, 2.6 Hz, 1H), 3.85 (t, J=9.0 Hz, 1H), 3.70 (dd, J=8.7, 2.7 Hz, 1H), 2.16 (s, 3H), 2.01 (q, J=7.3 Hz, 4H), 1.01 (s, 9H), 0.59 (t, J=7.3 Hz, 6H) ppm.

Ethyl 2-(4-(3-(4-(2-hydroxy-3,3-dimethylbutoxy)-3-methylphenyl)pentan-3-yl)-2-(hydroxymethyl)phenoxy)acetate Compound 335-3: colourless oil: $R_f$ 0.14 (20:80 EtOAc/Hex); $^1$H NMR (400 MHz, CDCl$_3$) δ 7.06 (d, J=2.4 Hz, 1H), 7.03 (dd, J=8.5, 2.5 Hz, 1H), 6.94 (dd, J=8.5, 2.4 Hz, 1H), 6.87 (d, J=2.0 Hz, 1H), 6.69 (d, J=6.3 Hz, 1H), 6.67 (d, J=6.3 Hz, 1H), 4.67 (s, 2H), 4.66 (s, 2H), 4.26 (q, J=7.1 Hz, 2H), 4.08 (dd, J=9.2, 2.7 Hz, 1H), 3.85 (t, J=8.9 Hz, 1H), 3.70 (dd, J=8.7, 2.5 Hz, 1H), 2.16 (s, 3H), 2.03 (q, J=7.3 Hz, 4H), 1.29 (t, J=7.1 Hz, 3H), 1.01 (s, 9H), 0.58 (t, J=7.3 Hz, 6H) ppm.

N-hydroxy-2-(4-(3-(4-(2-hydroxy-3,3-dimethylbutoxy)-3-methylphenyl)pentan-3-yl)-2-(hydroxymethyl)phenoxy)acetamide Compound DK-331: colourless film; IR (thin film) ν 3333, 2963, 2933, 2873, 1748, 1675, 1501, 1220, 1137 cm$^{-1}$; $^1$H NMR (500 MHz, CD$_3$OD) δ 7.13 (d, J=2.6 Hz, 1H), 7.10 (dd, J=8.6, 2.5 Hz, 1H), 6.97 (dd, J=8.4, 2.6 Hz, 1H), 6.85 (d, J=2.2 Hz, 1H), 6.83 (d, J=8.6 Hz, 1H), 6.75 (d, J=8.6 Hz, 1H), 4.60 (s, 2H), 4.59 (s, 2H), 4.10 (dd, J=10.0, 2.9 Hz, 1H), 3.85 (dd, J=10.1, 7.7 Hz, 1H), 3.61 (dd, J=7.7, 2.9 Hz, 1H), 2.13 (s, 3H), 2.07 (q, J=7.3 Hz, 4H), 0.99 (s, 9H), 0.59 (t, J=7.3 Hz, 6H). $^{13}$C NMR (125 MHz, CD$_3$OD) δ 154.9, 153.5, 142.3, 140.2, 130.1, 129.0, 128.6, 128.1, 125.7, 125.5, 110.7, 109.80, 77.2, 69.5, 66.5, 59.8, 33.7, 28.7, 25.2, 15.4, 7.3 ppm; HRMS (ESI) Calc. for C$_{27}$H$_{38}$O$_6$N [M–H]$^-$: 472.27046, found: 472.27110.

EXAMPLE 37

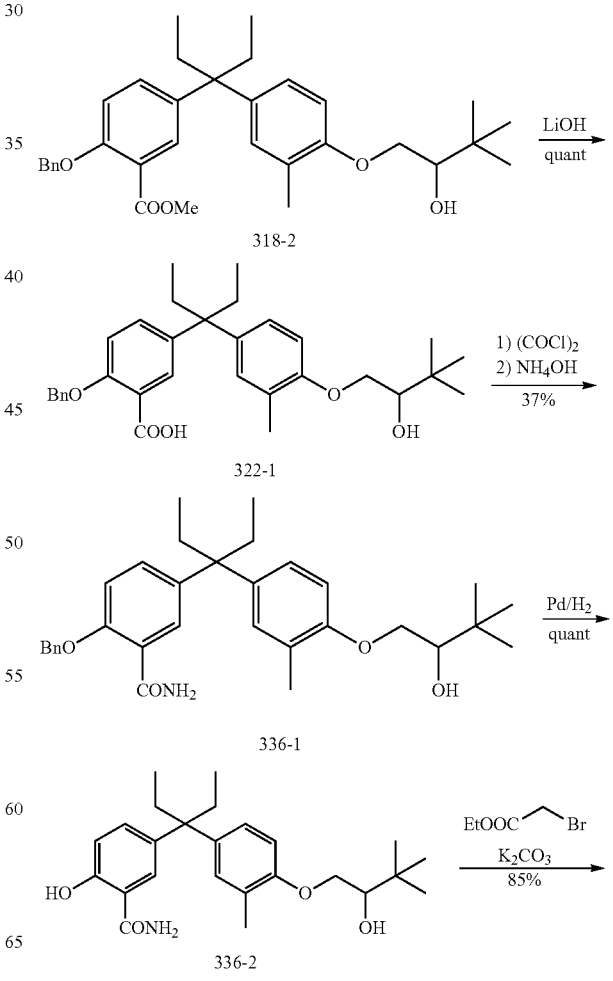

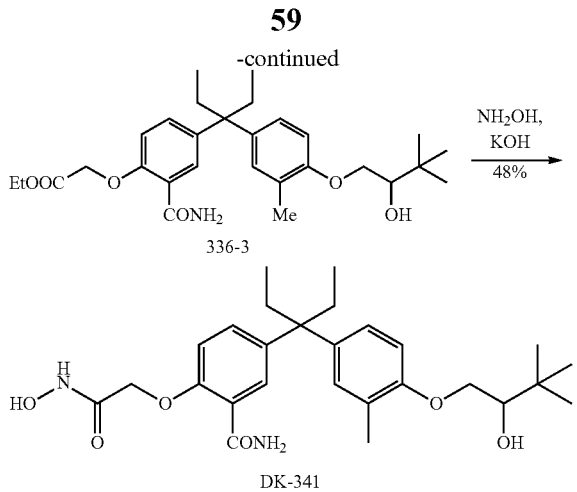

The compounds of the above scheme are characterized as follows:

2-(benzyloxy)-5-(3-(4-(2-hydroxy-3,3-dimethylbutoxy)-3-methylphenyl)pentan-3-yl)benzoic acid Compound 322-1: colourless oil: $R_f$ 0.25 (40:60 EtOAc/Hex); $^1$H NMR (400 MHz, CDCl$_3$) δ 8.19 (d, J=2.6 Hz, 1H), 7.45-7.35 (m, 5H), 7.23 (dd, J=8.7, 2.6 Hz, 1H), 7.00 (d, J=8.6 Hz, 1H), 6.92 (dd, J=8.6 and 1.8 Hz, 1H), 6.84 (s, 1H), 6.70 (d, J=8.5 Hz, 1H), 5.25 (s, 2H), 4.09 (dd, J=9.2, 2.7 Hz, 1H), 3.85 (t, J=9.0 Hz, 1H), 3.70 (d, J=9.5 Hz, 1H), 2.16 (s, 3H), 2.06 (q, J=7.3 Hz, 4H), 1.01 (s, 9H), 0.60 (t, J=7.3 Hz, 6H) ppm. $^{13}$C NMR (75 MHz, CDCl$_3$) δ 165.6, 155.3, 154.6, 143.7, 140.0, 135.3, 134.4, 132.4, 130.5, 129.2, 129.1, 128.0, 126.0, 116.8, 112.6, 110.3, 72.3, 69.3, 48.7, 33.6, 29.0, 26.1, 16.6, 8.3 ppm.

2-(benzyloxy)-5-(3-(4-(2-hydroxy-3,3-dimethylbutoxy)-3-methylphenyl)pentan-3-yl)benzamide Compound 336-1 colourless oil: $R_f$ 0.12 (20:80 EtOAc/Hex); $^1$H NMR (500 MHz, CDCl$_3$) δ 8.19 (d, J=2.6 Hz, 1H), 7.76 (bs, 1H), 7.51-7.32 (m, 5H), 7.14 (dd, J=8.7, 2.6 Hz, 1H), 6.98-6.90 (m, 2H), 6.88 (d, J=1.8 Hz, 1H), 6.69 (d, J=8.5 Hz, 1H), 5.66 (bs, 1H), 5.14 (s, 2H), 4.08 (dd, J=9.2, 2.7 Hz, 1H), 3.85 (t, J=9.0 Hz, 1H), 3.70 (d, J=9.5 Hz, 1H), 2.16 (s, 3H), 2.10 (m, 4H), 1.01 (s, 9H), 0.60 (t, J=7.3 Hz, 6H) ppm.

2-hydroxy-5-(3-(4-(2-hydroxy-3,3-dimethylbutoxy)-3-methylphenyl)pentan-3-yl)benzamide Compound 336-2 colourless oil: $R_f$ 0.25 (40:60 EtOAc/Hex); $^1$H NMR (400 MHz, CDCl$_3$) δ 7.21 (dd, J=8.8, 2.3 Hz, 1H), 7.13 (d, J=2.3 Hz, 1H), 6.94 (dd, J=8.4, 2.5 Hz, 1H), 6.88 (d, J=7.0 Hz, 1H), 6.87 (s, 1H), 6.71 (d, J=8.5 Hz, 1H), 4.09 (dd, J=9.2, 2.6 Hz, 1H), 3.85 (t, J=8.9 Hz, 1H), 3.71 (dt, J=8.7, 2.6 Hz, 1H), 2.17 (s, 3H), 2.02 (dd, J=14.1, 6.2 Hz, 4H), 1.01 (s, 9H), 0.61 (t, J=7.3 Hz, 6H) ppm.

Ethyl 2-(2-carbamoyl-4-(3-(4-(2-hydroxy-3,3-dimethylbutoxy)-3-methylphenyl)pentan-3-yl)phenoxy)acetate Compound 336-3 colourless oil: $R_f$ 0.15 (20:80 EtOAc/Hex); $^1$H NMR (500 MHz, CDCl$_3$) δ 8.39 (bs, 1H), 8.20 (d, J=2.6 Hz, 1H), 7.13 (dd, J=8.6, 2.6 Hz, 1H), 6.93 (dd, J=8.5, 2.3 Hz, 1H), 6.85 (d, J=1.8 Hz, 1H), 6.70 (t, J=8.9 Hz, 2H), 5.79 (bs, 1H), 4.69 (s, 2H), 4.31 (q, J=7.1 Hz, 2H), 4.07 (dd, J=9.2, 2.7 Hz, 1H), 3.84 (t, J=9.0 Hz, 1H), 3.69 (d, J=8.7 Hz, 1H), 2.15 (s, 3H), 2.09 (q, J=7.2 Hz, 4H), 1.32 (t, J=7.1 Hz, 3H), 1.00 (s, 9H), 0.59 (t, J=7.3 Hz, 6H) ppm.

5-(3-(4-(2-hydroxy-3,3-dimethylbutoxy)-3-methylphenyl)pentan-3-yl)-2-(2-(hydroxyamino)-2-oxoethoxy)benzamide Compound DK-331: colourless film; $^1$H NMR (500 MHz, CD$_3$OD) δ 7.75 (d, J=2.3 Hz, 1H), 7.25 (dd, J=7.7, 1.5 Hz, 1H), 7.00-6.93 (m, 2H), 6.85 (s, 1H), 6.77 (d, J=8.6 Hz, 1H), 4.66 (s, 2H), 4.11 (dd, J=10.0, 3.0 Hz, 1H), 3.86 (dd, J=10.0, 7.7 Hz, 1H), 3.61 (dd, J=7.7, 2.9 Hz, 1H), 2.14 (s, 3H), 2.09 (q, J=7.3 Hz, 4H), 0.99 (s, 9H), 0.60 (t, J=7.3 Hz, 6H) ppm; $^{13}$C NMR (125 MHz, CD$_3$OD) δ 169.0, 154.9, 154.1, 142.6, 139.7, 129.9, 125.7, 121.4, 109.9, 77.4, 77.0, 69.3, 33.7, 28.6, 25.3, 25.1, 15.4, 7.2 ppm; LRMS (ESI) m/z 487.4 [M+H]$^+$;

EXAMPLE 38

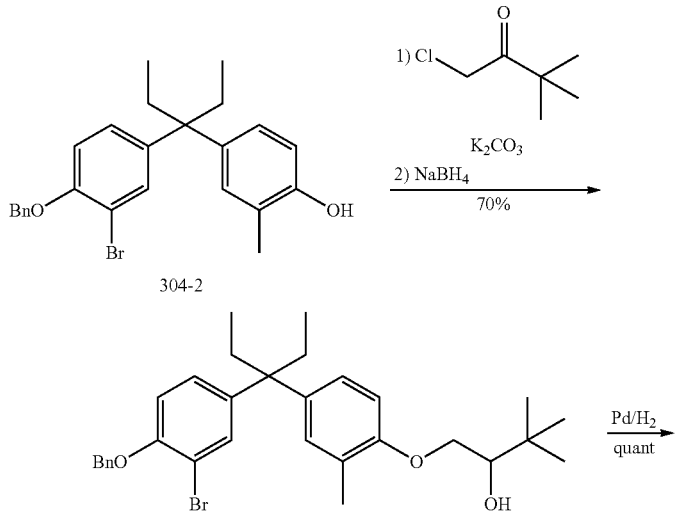

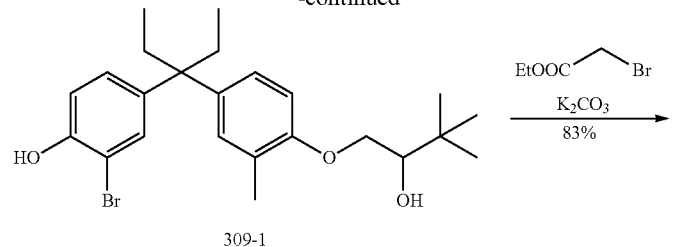

309-1

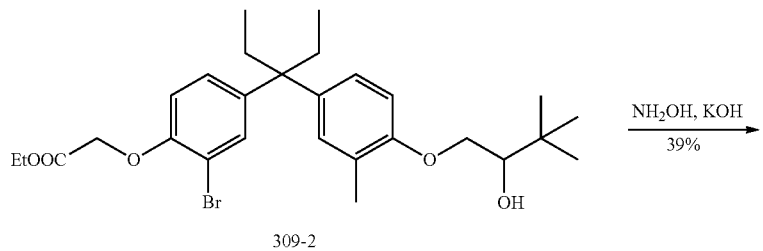

309-2

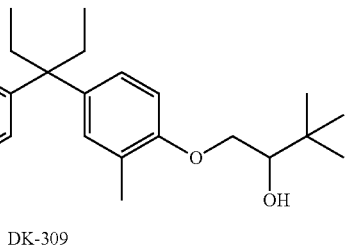

DK-309

The compounds of the above scheme are characterized as follows:

1-(4-(3-(4-(benzyloxy)-3-bromophenyl)pentan-3-yl)-2-methylphenoxy)-3,3-dimethylbutan-2-ol Compound 307-2: colourless oil: $R_f$ 0.69 (20:80 EtOac/Hex); $^1$H NMR (400 MHz, CDCl$_3$) δ 7.47 (d, J=7.3 Hz, 1H), 7.42-7.30 (m, 5H), 6.99 (dd, J=8.6, 2.3 Hz, 1H), 6.93 (dd, J=8.5, 2.4 Hz, 1H), 6.87 (d, J=2.0 Hz, 1H), 6.81 (d, J=8.6 Hz, 1H), 6.70 (d, J=8.5 Hz, 1H), 5.11 (s, 2H), 4.09 (dd, J=9.2, 2.6 Hz, 1H), 3.85 (t, J=8.9 Hz, 1H), 3.70 (dd, J=8.7, 2.6 Hz, 1H), 2.17 (s, 3H), 2.01 (q, J=7.2 Hz, 4H), 0.96 (s, 9H), 0.60 (t, J=7.3 Hz, 6H) ppm;

2-bromo-4-(3-(4-(2-hydroxy-3,3-dimethylbutoxy)-3-methylphenyl)pentan-3-yl)phenol Compound 309-1: colourless oil: $R_f$ 0.20 (20:80 EtOac/Hex); $^1$H NMR (400 MHz, CDCl$_3$) δ 7.47 (d, J=7.3 Hz, 1H), 6.99 (dd, J=8.6, 2.3 Hz, 1H), 6.93 (dd, J=8.5, 2.4 Hz, 1H), 6.87 (d, J=2.0 Hz, 1H), 6.81 (d, J=8.6 Hz, 1H), 6.70 (d, J=8.5 Hz, 1H), 4.09 (dd, J=9.2, 2.6 Hz, 1H), 3.85 (t, J=8.9 Hz, 1H), 3.70 (dd, J=8.7, 2.6 Hz, 1H), 2.17 (s, 3H), 2.01 (q, J=7.2 Hz, 4H), 0.96 (s, 9H), 0.60 (t, J=7.3 Hz, 6H) ppm;

Ethyl 2-(2-bromo-4-(3-(4-(2-hydroxy-3,3-dimethylbutoxy)-3-methylphenyl)pentan-3-yl)phenoxy)acetate Compound 309-2: colourless oil: $R_f$ 0.72 (20:80 EtOac/Hex); $^1$H NMR (300 MHz, CDCl$_3$) δ 7.37 (d, J=2.2 Hz, 1H), 6.99 (dd, J=8.6, 2.3 Hz, 1H), 6.93 (dd, J=8.4, 2.2 Hz, 1H), 6.86 (d, J=2.1 Hz, 1H), 6.70 (d, J=5.4 Hz, 1H), 6.68 (d, J=5.5 Hz, 1H), 4.66 (s, 2S), 4.32-4.18 (q, J=5.5 Hz, 2H), 4.09 (dd, J=9.2, 2.5 Hz, 1H), 3.85 (t, J=8.9 Hz, 1H), 3.70 (dd, J=8.7, 2.5 Hz, 1H), 2.17 (s, 3H), 2.01 (q, J=7.3 Hz, 4H), 1.27 (t, J=5.5 Hz, 3H), 1.01 (s, 9H), 0.59 (t, J=7.3 Hz, 6H) ppm; $^{13}$C NMR (75 MHz, CDCl$_3$) δ 168.6, 154.5, 151.9, 144.3, 140.1, 133.0, 130.5, 128.1, 126.1, 125.8, 112.9, 111.7, 110.2, 69.1, 67.8, 66.5, 61.4, 48.6, 33.6, 29.2, 26.1, 16.6, 14.0, 8.3 ppm.

2-(2-bromo-4-(3-(4-(2-hydroxy-3,3-dimethylbutoxy)-3-methylphenyl)pentan-3-yl)phenoxy)-N-hydroxyacetamide Compound DK-309: colourless film; $^1$H NMR (400 MHz, CD$_3$OD) δ 7.29 (d, J=2.2 Hz, 1H), 7.12 (dd, J=8.6, 2.2 Hz, 1H), 6.96 (dd, J=8.5, 2.3 Hz, 1H), 6.92 (d, J=8.7 Hz, 1H), 6.84 (d, J=1.8 Hz, 1H), 6.78 (d, J=8.5 Hz, 1H), 4.57 (s, 2H), 4.12 (dd, J=10.0, 2.9 Hz, 1H), 3.87 (dd, J=10.0, 7.9 Hz, 1H), 3.62 (dd, J=7.8, 2.8 Hz, 1H), 2.16 (s, 3H), 2.04 (q, J=7.3 Hz, 4H), 1.00 (s, 9H), 0.59 (t, J=7.3 Hz, 6H). $^{13}$C NMR (75 MHz, CD$_3$OD) δ 166.0, 155.1, 152.1, 144.8, 139.4, 132.7, 129.9, 128.0, 125.8, 125.7, 113.4, 111.3, 109.9, 77.2, 69.5, 67.4, 33.7, 28.7, 25.2, 15.4, 7.2 ppm; LRMS (ESI) m/z 522.3 [M+H]$^+$.

EXAMPLE 39

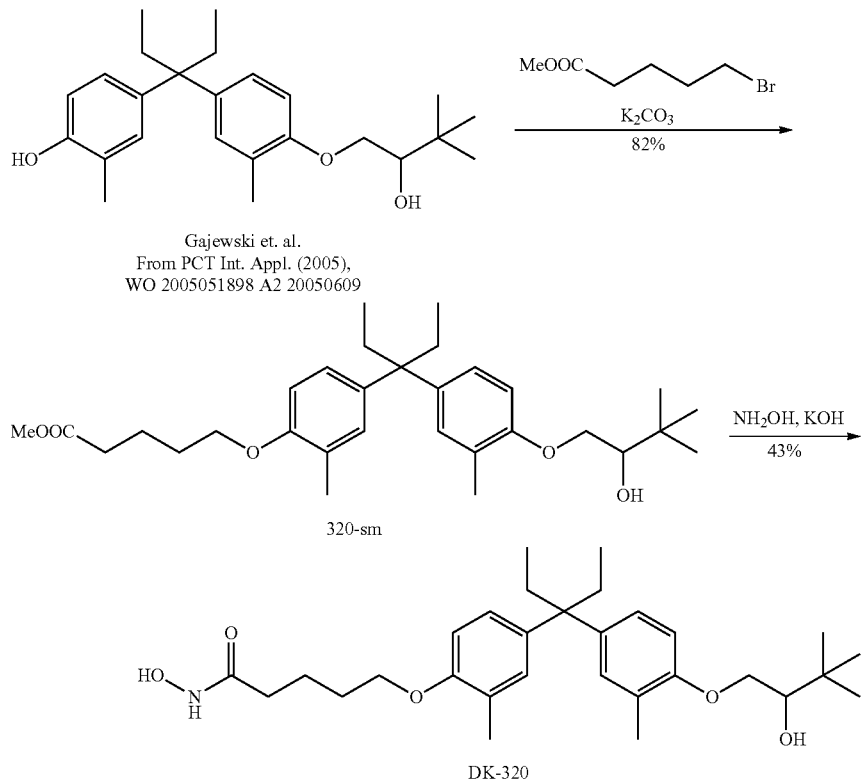

The compounds of the above scheme are characterized as follows:

Compounds DK-319 and DK-347 were prepared according to this scheme using different length alkyl bromides

Methyl 5-(4-(3-(4-(2-hydroxy-3,3-dimethylbutoxy)-3-methylphenyl)pentan-3-yl)-2-methylphenoxy)pentanoate Compound 320-sm: colourless oil: $R_f$ 0.75 (20:80 EtOac/Hex); IR (thin film) ν 3488, 2952, 2874, 1739, 1504, 1244 cm$^{-1}$; $^1$H NMR (500 MHz, CDCl$_3$) δ 6.96-6.87 (m, 4H), 6.69 (d, J=8.6 Hz, 1H), 6.66 (d, J=8.4 Hz, 1H), 4.08 (dd, J=9.1, 2.7 Hz, 1H), 3.94 (t, J=5.4 Hz, 2H), 3.85 (t, J=8.9 Hz, 1H), 3.74-3.67 (m, 1H), 3.67 (s, 3H), 2.41 (t, J=6.2 Hz, 2H), 2.17 (s, 3H), 2.15 (s, 3H), 2.01 (q, J=7.3 Hz, 4H), 1.87-1.73 (m, 4H), 1.01 (s, 9H), 0.59 (t, J=7.3 Hz, 6H) ppm; $^{13}$C NMR (125 MHz, CDCl$_3$) δ 174.0, 154.6, 154.2, 141.3, 140.4, 130.7, 130.4, 126.2, 126.0, 125.5, 125.4, 110.0, 109.6, 69.1, 67.1, 51.5, 48.4, 33.5, 29.3, 28.9, 26.1, 21.8, 16.6, 16.5, 8.5 ppm; HRMS (ESI) Calc. for C$_{31}$H$_{46}$O$_5$Na [M+Na]$^+$: 521.32375, found 521.32352.

N-hydroxy-5-(4-(3-(4-(2-hydroxy-3,3-dimethylbutoxy)-3-methylphenyl)pentan-3-yl)-2-methylphenoxy)pentanamide Compound DK-320: colourless film; IR (thin film) ν 3238, 2962, 2933, 2873, 1655, 1609, 1503, 1275 cm$^{-1}$; $^1$H NMR (500 MHz, CD$_3$OD) δ 6.97-6.91 (m, 2H), 66.85 (d, J=2.7 Hz, 1H), 6.83 (d, J=2.7 Hz, 1H), 6.75 (d, J=8.6 Hz, 1H), 6.73 (d, J=8.6 Hz, 1H), 4.11 (dd, J=10.0, 2.9 Hz, 1H), 3.96 (t, J=5.8 Hz, 2H), 3.86 (dd, J=10.0, 7.7 Hz, 1H), 3.61 (dd, J=7.7, 2.9 Hz, 1H), 2.20-2.13 (m, 5H), 2.10 (s, 3H), 2.03 (q, J=7.4 Hz, 4H), 1.87-1.75 (m, 4H), 1.00 (s, 9H), 0.58 (t, J=7.3 Hz, 6H) ppm; $^{13}$C NMR (75 MHz, CD$_3$OD) δ 171.2, 154.8, 154.7, 140.6, 140.5, 130.1, 130.0, 125.7, 125.4, 125.1, 109.8, 109.6, 77.2, 69.5, 67.0, 33.7, 32.1, 28.8, 28.6, 25.2, 22.2, 15.4, 15.2, 7.3 ppm; HRMS (ESI) Calc. for C$_{30}$H$_{44}$O$_5$N [M−H]$^-$: 498.32250, found: 498.32318;

Methyl 7-(4-(3-(4-(2-hydroxy-3,3-dimethylbutoxy)-3-methylphenyl)pentan-3-yl)-2-methylphenoxy)heptanoate Compound 347-sm: colourless oil: $R_f$ 0.70 (20:80 EtOac/Hex); IR (thin film) ν 3320, 2952, 2937, 2865, 1739, 1504, 1220, 1137 cm$^{-1}$; $^1$H NMR (500 MHz, CDCl$_3$) δ 6.93 (m, 3H), 6.89 (d, J=8.5 Hz, 1H), 6.69 (d, J=8.5 Hz, 1H), 6.66 (d, J=8.5 Hz, 1H), 4.08 (dd, J=9.2, 2.6 Hz, 1H), 3.91 (t, J=6.3 Hz, 2H), 3.85 (t, J=8.9 Hz, 1H), 3.70 (dt, J=8.7, 2.7 Hz, 1H), 3.66 (s, 3H), 2.45 (t, J=2.6 Hz, 1H), 2.32 (t, J=7.5 Hz, 2H), 2.17 (s, 3H), 2.15 (s, 3H), 2.01 (q, J=7.3 Hz, 4H), 1.85-1.73 (m, 2H), 1.72-1.61 (m, 2H), 1.53-1.45 (m, 2H), 1.43-1.33 (m, 2H), 1.01 (s, 9H), 0.59 (t, J=7.3 Hz, 6H) ppm; $^{13}$C NMR (125 MHz, CDCl$_3$) δ 174.2, 154.8, 154.2, 141.3, 141.1, 140.3, 130.6, 130.4, 126.1, 126.0, 125.4, 110.0, 109.7, 69.1, 67.6, 51.5, 48.4, 34.0, 33.5, 29.3, 29.3, 28.9, 26.1, 25.9, 24.9, 16.6, 16.5, 8.5, 8.4 ppm; HRMS (ESI) Calc. for C$_{33}$H$_{50}$O$_5$Na [M+Na]$^+$: 549.35505, found 549.35443.

N-hydroxy-7-(4-(3-(4-(2-hydroxy-3,3-dimethylbutoxy)-3-methylphenyl)pentan-3-yl)-2-methylphenoxy)heptanamide Compound DK-347: colourless film; $^1$H NMR (500 MHz, CD$_3$OD) δ 6.97-6.91 (m, 2H), 6.85 (d, J=2.7 Hz, 1H), 6.83 (d, J=2.7 Hz, 1H), 6.75 (d, J=8.6 Hz, 1H), 6.72 (d, J=8.5 Hz, 1H), 4.11 (dd, J=10.0, 2.9 Hz, 1H), 3.94 (t, J=6.3 Hz, 2H), 3.86 (dd, J=10.0, 7, 8 Hz, 1H), 3.61 (dd, J=7.8, 2.9 Hz, 1H), 2.15 (s, 3H), 2.12-2.07 (m, 5H), 2.03 (q, J=7.3 Hz, 4H), 1.83-1.73 (m, 2H), 1.68-1.61 (m, 2H), 1.57-1.45 (m, 2H), 1.45-1.36 (m, 2H), 1.00 (s, 9H), 0.58 (t, J=7.3 Hz, 6H). $^{13}$C NMR (125 MHz, CD$_3$OD) δ 154.8, 140.6, 140.4, 130.1, 130.0, 125.7, 125.3, 125.1, 109.7, 109.6, 105.0, 77.2, 69.47, 67.4, 33.7, 29.0, 28.8, 28.5, 25.6, 25.3, 25.2, 15.4, 15.2, 7.3 ppm; HRMS (ESI) Calc. for C$_{32}$H$_{48}$O$_5$N [M-H]$^-$: 526.35380, found: 526.35438;

Methyl 6-(4-(3-(4-(2-hydroxy-3,3-dimethylbutoxy)-3-methylphenyl)pentan-3-yl)-2-methylphenoxy)hexanoate Compound 319-sm: colourless oil: R$_f$ 0.75 (20:80 EtOac/Hex); IR (thin film) ν 3500, 2960, 2873, 1739, 1504, 1245 cm$^{-1}$; $^1$H NMR (500 MHz, CDCl$_3$) δ 6.96-6.87 (m, 4H), 6.69 (d, J=8.6 Hz, 1H), 6.67 (d, J=8.4 Hz, 1H), 4.08 (dd, J=9.1, 2.7 Hz, 1H), 3.95 (t, J=5.4 Hz, 2H), 3.85 (t, J=8.9 Hz, 1H), 3.70 (dd, J=9.1, 2.7 Hz, 1H), 3.67 (s, 3H), 2.35 (t, J=6.2 Hz, 2H), 2.16 (s, 3H), 2.14 (s, 3H), 2.01 (q, J=7.3 Hz, 4H), 1.83-1.76 (m, 2H), 1.74-1.68 (m, 2H), 1.54-1.48 (m, 2H), 1.01 (s, 9H), 0.59 (t, J=7.3 Hz, 6H) ppm; $^{13}$C NMR (125 MHz, CDCl$_3$) δ 174.1, 154.7, 154.2, 141.3, 140.3, 130.7, 130.4, 126.2, 126.0, 125.5, 125.4, 110.0, 109.7, 69.1, 67.4, 51.5, 48.4, 34.0, 33.5, 29.3, 29.1, 26.1, 25.8, 24.7, 16.6, 16.5, 8.5 ppm; HRMS (ESI) Calc. for C$_{32}$H$_{48}$O$_5$Na [M+Na]$^+$: 535.33940, found 535.33784.

N-hydroxy-6-(4-(3-(4-(2-hydroxy-3,3-dimethylbutoxy)-3-methylphenyl)pentan-3-yl)-2-methylphenoxy)hexanamide Compound DK-319: IR (thin film) ν 3238, 2961, 2940, 2873, 1654, 1503, 1220 cm$^{-1}$; $^1$H NMR (500 MHz, CD$_3$OD) δ 6.97-6.90 (m, 2H), 6.85 (d, J=2.7 Hz, 1H), 6.83 (d, J=2.7 Hz, 1H), 6.74 (dd, J=8.6 Hz, 2H), 4.11 (dd, J=10.0, 3.0 Hz, 1H), 3.94 (t, J=6.3 Hz, 2H), 3.86 (dd, J=10.0, 7.8 Hz, 1H), 3.61 (dd, J=7.7, 2.9 Hz, 1H), 2.15 (s, 3H), 2.12 (t, J=6.2 Hz, 2H), 2.10 (s, 3H), 2.03 (q, J=7.2 Hz, 4H), 1.87-1.75 (m, 2H), 1.75-1.63 (m, 2H), 1.60-1.47 (m, 2H), 0.99 (s, 9H), 0.58 (t, J=7.3 Hz, 6H) ppm; $^{13}$C NMR (125 MHz, CD$_3$OD) δ 171.4, 154.8, 154.8, 140.6, 140.4, 130.1, 130.1, 125.7, 125.4, 125.1, 109.8, 109.6, 77.2, 69.5, 67.3, 33.7, 32.3, 28.8, 25.4, 25.2, 25.1, 15.4, 15.2 ppm; HRMS (ESI) Calc. for C$_{31}$H$_{46}$O$_5$N [M-H]$^-$: 512.33815, found: 512.33769;

EXAMPLE 40

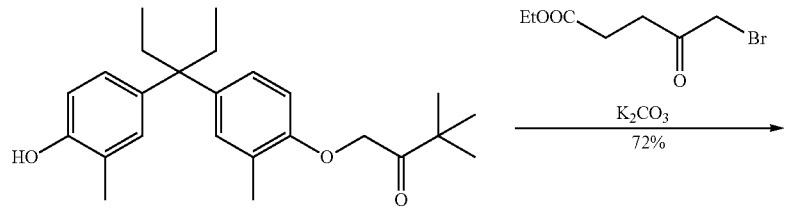

Gajewski et. al.
From PCT Int. Appl. (2005),
WO 2005051898 A2 20050609

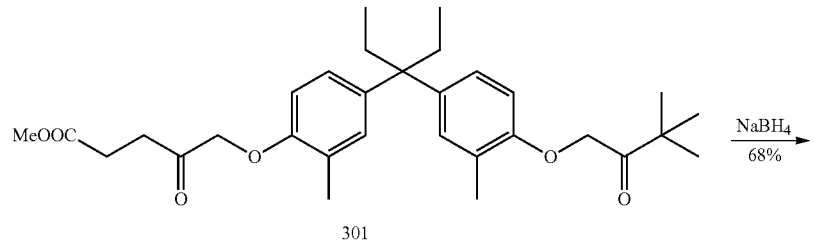

301

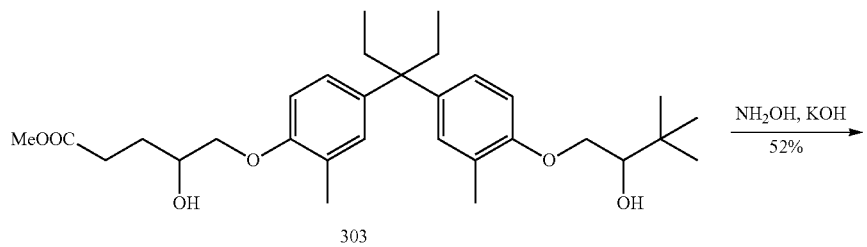

303

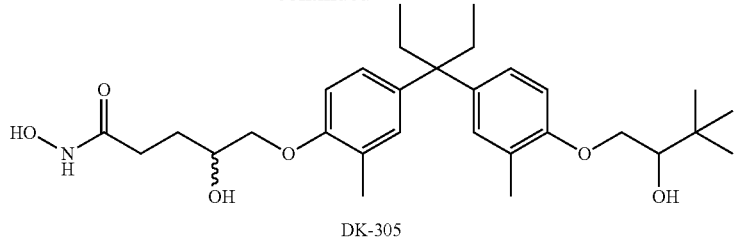

DK-305

The compounds of the above scheme are characterized as follows:

Ethyl 5-(4-(3-(4-(3,3-dimethyl-2-oxobutoxy)-3-methylphenyl)pentan-3-yl)-2-methylphenoxy)-4-oxopentanoate Compound 301: colourless oil: $R_f$ 0.40 (20:80 EtOac/Hex); IR (thin film) v 2966, 2958, 2877, 1727, 1502, 1220 cm$^{-1}$; $^1$H NMR (400 MHz, CDCl$_3$) δ 6.91 (m, 2H), 6.56 (d, J=8.3 Hz, 2H), 6.49 (d, J=8.3 Hz, 2H), 4.83 (s, 2H), 4.55 (s, 2H), 4.13 (q, J=7.1 Hz, 2H), 2.97 (t, J=6.5 Hz, 2H), 2.65 (t, J=6.5 Hz, 2H), 2.23 (s, 6H), 2.01 (q, J=7.3 Hz, 4H), 1.41-1.04 (m, 12H), 0.58 (t, J=7.3 Hz, 4H) ppm; $^{13}$C NMR (125 MHz, CDCl$_3$) δ 210.0, 206.9, 172.6, 154.0, 153.5, 141.7, 141.3, 130.9, 130.7, 126.2, 126.0, 126.0, 125.6, 110.1, 109.7, 72.9, 69.6, 60.7, 48.4, 43.2, 33.9, 29.2, 27.5, 26.4, 16.7, 16.6, 14.2, 8.4 ppm; HRMS (ESI) Calc. for C$_{32}$H$_{44}$O$_6$Na [M+Na]$^+$: 547.30301, found 547.30254.

Methyl 4-hydroxy-5-(4-(3-(4-(2-hydroxy-3,3-dimethylbutoxy)-3-methylphenyl)pentan-3-yl)-2-methylphenoxy)pentanoate Compound 303: colourless oil: $R_f$ 0.27 (20:80 EtOac/Hex); IR (thin film) v 3444, 2963, 1730, 1717, 1276 cm$^{-1}$; $^1$H NMR (500 MHz, CDCl$_3$) δ 6.94 (d, J=9.0 Hz, 2H), 6.89 (s, 2H), 6.69 (m, 2H), 4.18-4.12 (q, J=7.8 Hz, 2H), 4.08 (dd, J=9.2, 2.6 Hz, 1H), 4.04 (bs, 1H), 3.96 (dd, J=9.3, 2.6 Hz, 1H), 3.89-3.80 (m, 2H), 3.70 (d, J=8.5 Hz, 1H), 2.59-2.48 (m, 3H), 2.44 (bs, 1H), 2.16 (s, 6H), 2.02 (q, J=7.1 Hz, 4H), 1.97-1.79 (m, 2H), 1.26 (t, J=7.8 Hz, 3H), 1.00 (s, 9H), 0.59 (t, J=7.3 Hz, 6H) ppm; $^{13}$C NMR (125 MHz, CDCl$_3$) δ 173.8, 154.3, 154.0, 141.2, 141.1, 130.6, 126.2, 126.1, 125.5, 125.4, 110.0, 110.0, 71.6, 69.6, 69.1, 60.6, 48.4, 33.5, 30.5, 29.3, 28.3, 26.1, 16.6, 16.6, 14.2, 8.4 ppm; HRMS (ESI) Calc. for C$_{32}$H$_{46}$O$_6$Na [M+Na]$^+$: 551.33431, found 551.22408.

N,4-dihydroxy-5-(4-(3-(4-(2-hydroxy-3,3-dimethylbutoxy)-3-methylphenyl)pentan-3-yl)-2-methylphenoxy)pentanamide Compound DK-305: colourless film; IR (thin film) v 3313,2962, 2929, 2869,1503, 1220 cm$^{-1}$; $^1$H NMR (400 MHz, CD$_3$OD) δ 6.95 (d, J=8.5 Hz, 2H), 6.84 (s, 2H), 6.75 (d, J=8.5 Hz, 2H), 4.11 (dd, J=10.0, 2.9 Hz, 1H), 3.96-3.82 (m, 3H), 3.61 (dd, J=7.8, 2.8 Hz, 1H), 2.36-2.18 (m, 3H), 2.15 (s, 3H), 2.11 (s, 3H), 2.03 (q, J=7.2 Hz, 4H), 1.89-1.74 (m, 2H), 1.00 (s, 9H), 0.58 (t, J=7.3 Hz, 6H) ppm; $^{13}$C NMR (75 MHz, CD$_3$OD) δ 171.3, 154.82, 154.6, 140.8, 140.6, 130.1, 125.8, 125.7, 125.4, 109.8, 77.2, 71.6, 69.5, 69.0, 33.7, 29.3, 28.8, 25.2, 15.4, 153, 7.3 ppm; HRMS (ESI) Calc. for C$_{30}$H$_{44}$O$_6$N [M−H]$^-$: 514.31741, found: 514.31824; LRMS (ESI) m/z 516.5 [M+H]$^+$.

EXAMPLE 41

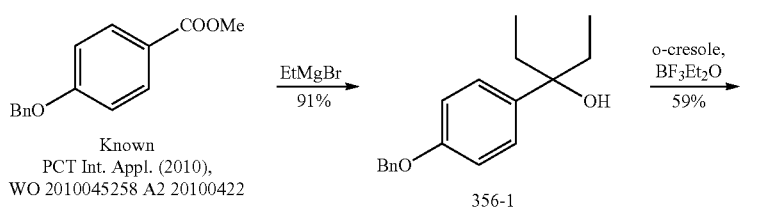

356-1

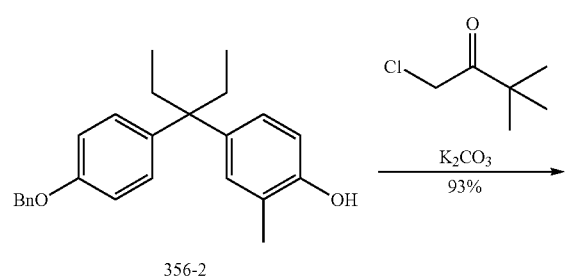

356-2

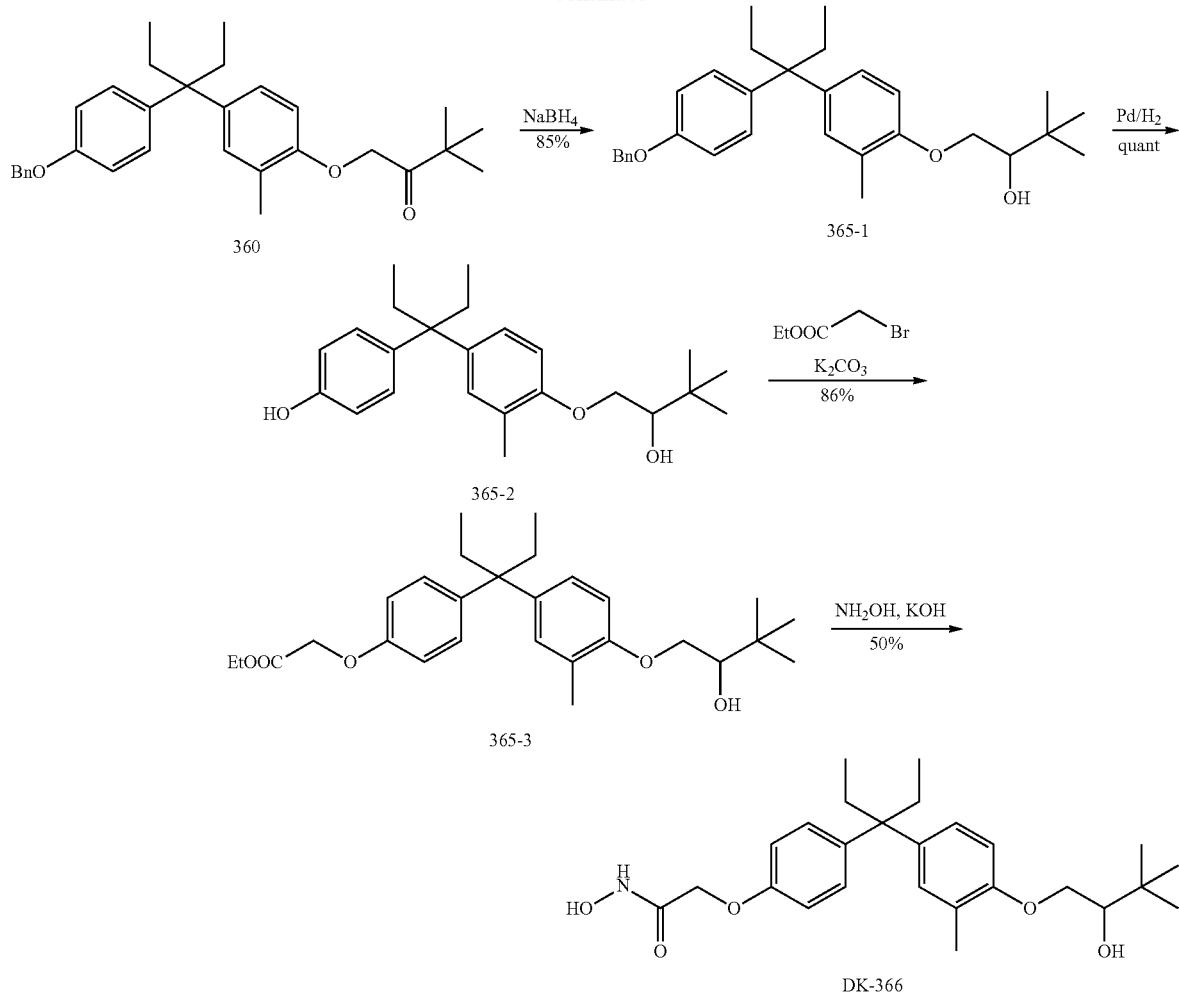

The compounds of the above scheme are characterized as follows:

Compounds DK-367 and DK-381 were synthesized from intermediate 365-2 with alkylation of appropriate alkyl bromides 3-(4-(benzyloxy)phenyl)pentan-3-ol Compound 356-1: colourless film: $R_f$ 0.70 (20:80 EtOAc/Hex); $^1$H NMR (400 MHz, CDCl$_3$) δ 7.49-7.32 (m, 5H), 7.29 (d, J=8.9 Hz, 2H), 6.95 (d, J=8.9 Hz, 2H), 5.06 (s, 2H), 2.01-1.71 (m, 4H), 0.76 (t, J=7.4 Hz, 6H). $^{13}$C NMR (75 MHz, CDCl$_3$) δ 157.3, 138.2, 137.1, 128.6, 128.0, 127.6, 126.7, 114.2, 70.0, 34.9, 7.9 ppm; HRMS (ESI) Calc. for C$_{18}$H$_{22}$O$_2$Na [M+Na]$^+$: 293.15120, found 293.15130.

4-(3-(4-(benzyloxy)phenyl)pentan-3-yl)-2-methylphenol

Compound 356-2: yellow oil: $R_f$ 0.25 (20:80 EtOAc/Hex); $^1$H NMR (400 MHz, CDCl$_3$) δ 7.48-7.29 (m, 5H), 7.10 (d, J=8.9 Hz, 2H), 6.92-5.86 (m, 4H), 6.66 (d, J=8.3 Hz, 1H), 5.04 (s, 2H), 4.61 (bs, 1H), 2.20 (s, 3H), 2.04 (q, J=7.3 Hz, 4H), 0.62 (t, J=7.3 Hz, 6H) ppm; $^{13}$C NMR (75 MHz, CDCl$_3$) δ 156.4, 151.3, 141.5, 141.1, 137.2, 130.7, 129.0, 128.6, 127.9, 127.6, 126.7, 122.5, 114.0, 113.8, 105.0, 70.0, 48.5, 29.4, 16.1, 8.4 ppm; HRMS (ESI) Calc. for C$_{25}$H$_{28}$O$_2$Na [M+Na]$^+$: 383.19815, found 383.19839.

1-(4-(3-(4-(benzyloxy)phenyl)pentan-3-yl)-2-methylphenoxy)-3,3-dimethylbutan-2-one Compound 360: colourless oil: $R_f$ 0.75 (20:80 EtOAc/Hex); $^1$H NMR (400 MHz, CDCl$_3$) δ 7.47-7.27 (m, 5H), 7.07 (d, J=8.8 Hz, 2H), 6.93-6.88 (m, 2H), 6.86 (d, J=8.8 Hz, 2H), 6.49 (d, J=8.3 Hz, 1H), 5.02 (s, 2H), 4.83 (s, 2H), 2.23 (s, 3H), 2.06-1.88 (m, 4H), 1.24 (s, 9H), 0.59 (t, J=7.3 Hz, 6H) ppm; $^{13}$C NMR (75 MHz, CDCl$_3$) δ 210.6, 156.4, 154.1, 141.4, 141.3, 137.2, 130.8, 129.0, 128.5, 127.9, 127.6, 126.1, 126.0, 113.8, 110.1, 69.9, 69.6, 48.5, 43.2, 29.3, 26.5, 26.4, 16.7, 8.4 ppm; HRMS (ESI) Calc. for C$_{31}$H$_{38}$O$_3$Na [M+Na]$^+$: 481.27132, found 481.27009.

1-(4-(3-(4-(benzyloxy)phenyl)pentan-3-yl)-2-methylphenoxy)-3,3-dimethylbutan-2-ol Compound 365-1: colourless oil: $R_f$ 0.72 (20:80 EtOAc/Hex); IR (thin film) ν 3591, 3033, 2962, 2875, 1608, 1506, 1182 cm$^{-1}$; $^1$H NMR (300 MHz, CDCl$_3$) δ 7.39 (m, 5H), 7.10 (d, J=8.6 Hz, 1H), 6.98 (d, J=8.4 Hz, 2H), 6.90 (m, 2H), 6.72 (d, J=8.4 Hz, 2H), 5.04 (s, 2H), 4.10 (dd, J=9.1, 2.3 Hz, 1H), 3.87 (t, J=8.9 Hz, 1H), 3.72 (dd, J=8.6, 2.2 Hz, 1H), 2.19 (s, 3H), 2.06 (q, J=7.2 Hz, 4H), 1.03 (s, 9H), 0.63 (t, J=7.2 Hz, 6H) ppm; $^{13}$C NMR (75 MHz, CDCl$_3$) δ 156.4, 154.3, 141.4, 141.1, 137.2, 130.7, 129.0, 128.5, 127.9, 127.6, 126.2, 125.5, 113.8, 110.7, 69.9, 69.2, 48.5, 33.6, 29.3, 26.1, 16.6, 8.4 ppm; HRMS (ESI) Calc. for C$_{31}$H$_{40}$O$_3$Na [M+Na]$^+$: 483.28697, found 483.28568.

4-(3-(4-(2-hydroxy-3,3-dimethylbutoxy)-3-methylphenyl)pentan-3-yl)phenol

Compound 365-2: colourless oil: R$_f$ 0.30 (20:80 EtOac/Hex); $^1$H NMR (300 MHz, CDCl$_3$) δ 7.02 (d, J=8.8 Hz, 2H), 6.96 (dd, J=8.5, 2.1 Hz, 1H), 6.90 (d, J=1.7 Hz, 1H), 6.71 (d, J=8.8 Hz, 2H), 6.69 (d, J=8.5 Hz, 1H), 4.10 (dd, J=9.2, 2.7 Hz, 1H), 3.88 (t, J=8.9 Hz, 1H), 3.73 (dd, J=8.6, 2.6 Hz, 1H), 2.17 (s, 3H), 2.03 (q, J=7.3 Hz, 4H), 1.02 (s, 9H), 0.61 (t, J=7.3 Hz, 6H) ppm; $^{13}$C NMR (75 MHz, CDCl$_3$) δ 154.2, 153.2, 141.2, 141.0, 130.7, 129.2, 126.1, 125.5, 114.4, 110.1, 69.1, 48.5, 33.6, 29.3, 26.1, 16.6, 8.4 ppm; HRMS (ESI) Calc. for C$_{24}$H$_{34}$O$_3$Na [M+Na]': 393.24002, found 393.23923.

Ethyl 2-(4-(3-(4-(2-hydroxy-3,3-dimethylbutoxy)-3-methylphenyl)pentan-3-yl)phenoxy)acetate Compound 365-3: colourless oil: R$_f$ 0.60 (20:80 EtOac/Hex); $^1$H NMR (300 MHz, CDCl$_3$) δ 7.07 (d, J=8.7 Hz, 2H), 6.94 (dd, J=8.5, 2.0 Hz, 1H), 6.88 (s, 1H), 6.78 (d, J=8.6 Hz, 2H), 6.69 (d, J=8.5 Hz, 1H), 4.58 (s, 2H), 4.26 (q, J=6.8 Hz, 2H), 4.08 (dd, J=9.2, 2.5 Hz, 1H), 3.85 (t, J=8.9 Hz, 1H), 3.70 (dd, J=8.7, 2.4 Hz, 1H), 2.16 (s, 3H), 2.02 (q, J=7.3 Hz, 4H), 1.28 (t, J=7.1 Hz, 3H), 1.00 (s, 9H), 0.59 (t, J=7.3 Hz, 6H) ppm; $^{13}$C NMR (75 MHz, CDCl$_3$) δ 169.1, 155.4, 154.4, 142.2, 140.9, 130.7, 129.1, 126.1, 125.5, 113.7, 110.1, 69.2, 68.2, 65.5, 61.3, 48.5, 33.6, 29.3, 26.1, 16.6, 14.2, 8.4 ppm;

N-hydroxy-2-(4-(3-(4-(2-hydroxy-3,3-dimethylbutoxy)-3-methylphenyl)pentan-3-yl)phenoxy)acetamide Compound DK-366: colourless film; IR (thin film) ν 3229, 2963, 2876, 1674, 1607, 1505, 1242 cm$^{-1}$; $^1$H NMR (500 MHz, CD$_3$OD) δ 7.08 (d, J=8.9 Hz, 2H), 6.95 (d, J=8.5 Hz, 1H), 6.88-6.80 (m, 3H), 6.75 (d, J=8.6 Hz, 1H), 4.50 (s, 2H), 4.10 (dd, J=10.0, 2.9 Hz, 1H), 3.85 (dd, J=. 10.0, 7.8 Hz, 1H), 3.61 (dd, J=7.7, 2.9 Hz, 1H), 2.15 (s, 3H), 2.05 (q, J=7.3 Hz, 4H), 0.99 (s, 9H), 0.58 (t, J=7.3 Hz, 6H) ppm; $^{13}$C NMR (125 MHz, CD$_3$OD) δ 166.6, 155.5, 154.9, 142.3, 140.2, 130.1, 128.8, 125.7, 125.5, 113.4, 109.8, 77.2, 69.5, 66.0, 33.7, 28.8, 25.2, 15.4, 7.3 ppm; HEMS (ESI) Calc. for C$_{27}$H$_{34}$O$_5$[M–H]$^-$: 442.26123, found: 442.26010; LRMS (ESI) m/z 444.4 [M+H]$^+$.

Methyl 6-(4-(3-(4-(2-hydroxy-3,3-dimethylbutoxy)-3-methylphenyl)pentan-3-yl)phenoxy)hexanoate Compound 367-sm: colourless oil: R$_f$ 0.65 (20:80 EtOac/Hex); IR (thin film) ν 3514, 2952, 2874, 1738, 1609, 1508, 1183 cm$^{-1}$; $^1$H NMR (300 MHz, CDCl$_3$) δ 7.05 (d, J=8.8 Hz, 2H), 6.95 (d, J=8.4 Hz, 1H), 6.90 (s, 1H), 6.76 (d, J=8.7 Hz, 2H), 6.69 (d, J=8.5 Hz, 1H), 4.08 (dd, J=9.1, 2.5 Hz, 1H), 3.92 (t, J=6.4 Hz, 2H), 3.85 (t, J=8.9 Hz, 1H), 3.70 (dd, J=8.8, 2.6 Hz, 1H), 3.66 (s, 3H), 2.34 (t, J=7.4 Hz, 2H), 2.16 (s, 3H), 2.02 (q, J=7.2 Hz, 4H), 1.89-1.62 (n, 4H), 1.61-1.38 (m, 2H), 1.00 (s, 9H), 0.59 (t, J=7.3 Hz, 6H) ppm; $^{13}$C NMR (75 MHz, CDCl$_3$) δ 174.1, 156.6, 154.3, 141.2, 140.9, 130.7, 129.0, 126.2, 125.5, 113.4, 110.0, 69.1, 67.4, 51.5, 48.5, 34.0, 33.5, 29.3, 29.1, 26.1, 25.7, 24.7, 16.6, 8.4 ppm; HRMS (ESI) Calc. for C$_{31}$H$_{46}$O$_5$Na [M+Na]$^+$: 521.32375, found 521.32295.

hydroxy-6-(4-(3-(4-(2-hydroxy-3,3-methylphenyl)pentan-3-yl)phenoxy)hexanamide

Compound DK-367: colourless film; IR (thin film) ν 3222, 2962, 2869, 1651, 1609, 1508, 1247 cm$^{-1}$; $^1$H NMR (400 MHz, CD$_3$OD) δ 7.02 (d, J=8.8 Hz, 2H), 6.95 (d, J=8.7 Hz, 1H), 6.84 (s, 1H), 6.74 (m, 3H), 4.09 (dd, J=10.0, 2.9 Hz, 1H), 3.91 (t, J=6.3 Hz, 2H), 3.85 (dd, J=9.9, 7.8 Hz, 1H), 3.61 (dd, J=7.7, 2.9 Hz, 1H), 2.14 (s, 3H), 2.11 (t, J=7.4 Hz, 2H), 2.03 (q, J=7.3 Hz, 4H), 1.83-1.61 (m, 4H), 1.50 (m, 2H), 0.99 (s, 9H), 0.58 (t, J=7.3 Hz, 6H) ppm; $^{13}$C NMR (125 MHz, CD$_3$OD) δ 171.5, 156.7, 154.8, 140.8, 130.1, 128.6, 125.8, 125.4, 113.1, 109.8, 77.2, 69.5, 67.2, 33.7, 32.3, 28.9, 28.7, 25.3, 25.2, 25.1, 15.5, 7.4 ppm; HRMS (ESI) Calc. for C$_{30}$H$_{44}$O$_5$N [M–H]$^-$: 498.32250, found: 498.32338; LRMS (ESI) m/z 500.5 [M+H]$^+$.

Methyl 5-(4-(3-(4-(2-hydroxy-3,3-dimethylbutoxy)-3-methylphenyl)pentan-3-yl)phenoxy)pentanoate Compound 378: colourless oil: R$_f$ 0.63 (20:80 EtOac/Hex); IR (thin film) ν 3528, 2959, 2875, 1736, 1608, 1508, 1183 cm$^{-1}$; $^1$H NMR (400 MHz, CDCl$_3$) δ 7.05 (d, J=8.8 Hz, 2H), 6.95 (dd, J=8.5, 2.4 Hz, 1H), 6.90 (d, J=2.1 Hz, 1H), 6.76 (d, J=8.8 Hz, 2H), 6.69 (d, J=8.5 Hz, 1H), 4.08 (dd, J=9.2, 2.6 Hz, 1H), 3.94 (t, J=5.7 Hz, 2H), 3.85 (t, J=8.9 Hz, 1H), 3.70 (dd, J=8.7, 2.6 Hz, 1H), 3.67 (s, 3H), 2.39 (t, J=7.0 Hz, 2H), 2.17 (s, 3H), 2.03 (q, J=7.3 Hz, 4H), 1.97-1.73 (m, 4H), 1.01 (s, 9H), 0.60 (t, J=7.3 Hz, 6H) ppm; $^{13}$C NMR (75 MHz, CDCl$_3$) δ 173.9, 156.5, 154.3, 141.1, 141.0, 130.7, 128.9, 126.1, 125.5, 113.4, 110.0, 69.1, 67.1, 51.6, 48.5, 33.7, 33.6, 29.3, 28.8, 26.1, 21.7, 16.6, 8.4 ppm; HRMS (ESI) Calc. for C$_{30}$H$_{44}$O$_5$Na [M+Na]$^+$: 507.3081, found 507.3099.

N-hydroxy-5-(4-(3-(4-(2-hydroxy-3,3-dimethylbutoxy)-3-methylphenyl)pentan-3-yl)phenoxy)pentanamide Compound DK-381: colourless film; IR (thin film) ν 3226, 2961, 2873, 1655, 1609, 1508, 1245 cm$^{-1}$; $^1$H NMR (500 MHz, CD$_3$OD) δ 7.04 (d, J=8.6 Hz, 2H), 6.96 (d, J=6.2 Hz, 1H), 6.84 (s, 1H), 6.76 (m, 3H), 4.10 (dd, J=10.0, 2.9 Hz, 1H), 3.94 (t, J=6.3 Hz, 2H), 3.86 (dd, J=10.0, 7.8 Hz, 1H), 3.61 (dd, J=7.8, 2.9 Hz, 1H), 2.15 (m, 5H), 2.04 (q, J=7.3 Hz, 4H), 1.78 (d, J=7.3 Hz, 4H), 0.99 (s, 9H), 0.58 (t, J=7.3 Hz, 6H) ppm; $^{13}$C NMR (125 MHz, CD$_3$OD) δ 171.5, 156.7, 154.9, 140.9, 140.4, 130.1, 128.6, 125.8, 125.4, 113.1, 109.8, 77.2, 69.5, 66.9, 33.7, 32.0, 28.9, 28.4, 25.2, 22.1, 15.4, 7.3 ppm; HRMS (ESI) Calc. for C$_{29}$H$_{42}$O$_5$N [M–H]$^-$: 484.3068, found: 484.3080; LRMS (ESI) m/z 486.5 [M+H]$^+$.

EXAMPLE 42

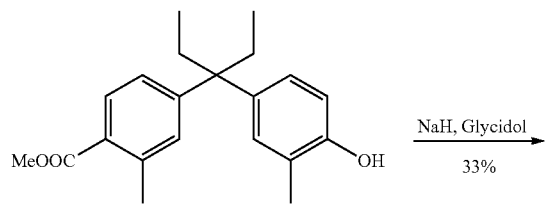

N. Sunil; Y Kwong
From PCT Int. Appl. (2004),
WO 2004063345 A2 20040729

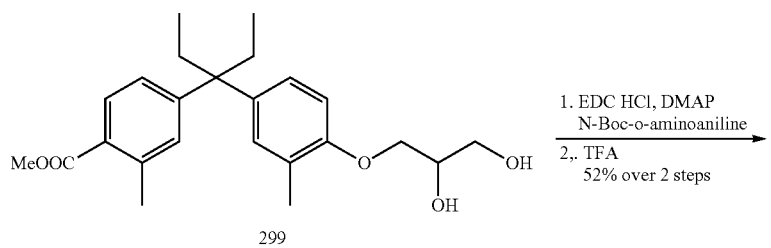

299

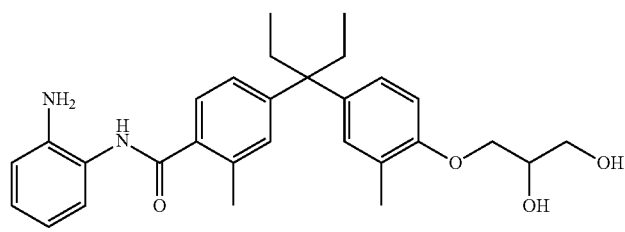

302

The compounds of the above scheme are characterized as follows:

Methyl 4-(3-(4-(2,3-dihydroxypropoxy)-3-methylphenyl)pentan-3-yl)-2-methylbenzoate Compound 299: colourless oil: $R_f$ 0.50 (40:60 EtOac/Hex); $^1$H NMR (300 MHz, CDCl$_3$) δ 7.91 (d, J=8.7 Hz, 1H), 7.04 (m, 2H), 6.94 (d, J=8.4 Hz, 1H), 6.86 (s, 1H), 6.71 (d, J=8.5 Hz, 1H), 4.18-4.08 (m, 1H), 4.10-4.04 (m, 2H), 3.86-3.80 (m, J=2H), 2.58 (s, 3H), 2.11-2.02 (s, 3H), 2.07 (m, 4H), 0.60 (t, J=7.2 Hz, 6H) ppm;

N-(2-aminophenyl)-4-(3-(4-(2,3-dihydroxypropoxy)-3-methylphenyl)pentan-3-yl)-2-methylbenzamide Compound 302: colourless film: $^1$H NMR (400 MHz, CD$_3$OD) δ 7.47 (d, J=7.9 Hz, 1H), 7.19 (d, J=9.1 Hz, 1H), 7.15-6.97 (m, 4H), 6.90 (d, J=9.2 Hz, 1H), 6.87-6.65 (m, 3H), 4.05-3.93 (m, 3H), 3.69 (ddd, J=11.2, 4.9 Hz, 2H), 2.44 (s, 3H), 2.14 (s, 3H), 2.13 (q, J=7.5 Hz, 4H), 0.62 (t, J=7.5 Hz, 6H). $^{13}$C NMR (125 MHz, CD$_3$OD) δ 154.9, 151.5, 139.9, 135.0, 130.3, 130.1, 127.0, 126.5, 125.7, 125.2, 118.4, 117.4, 109.9, 70.5, 68.9, 62.9, 28.4, 18.8, 15.2, 7.2 ppm; LRMS (ESI) m/z 477.7 [M+H]$^+$.

EXAMPLE 43

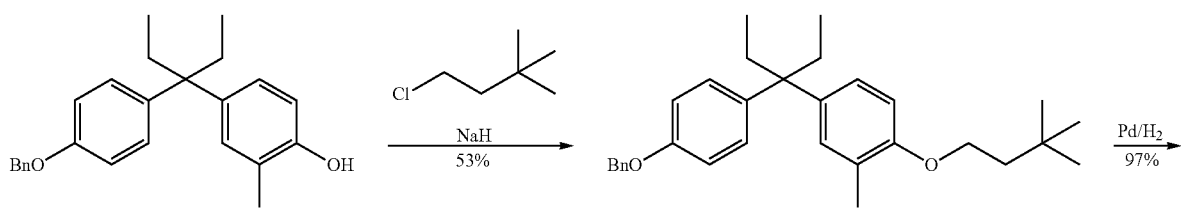

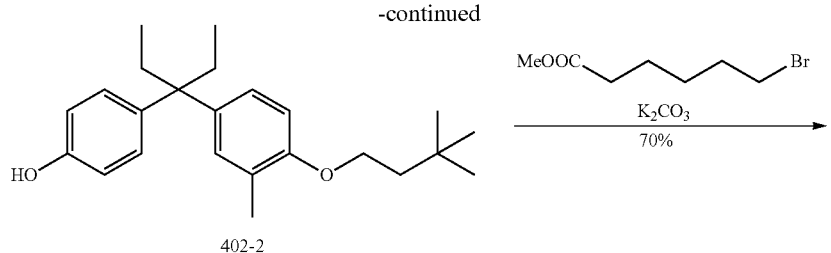

-continued

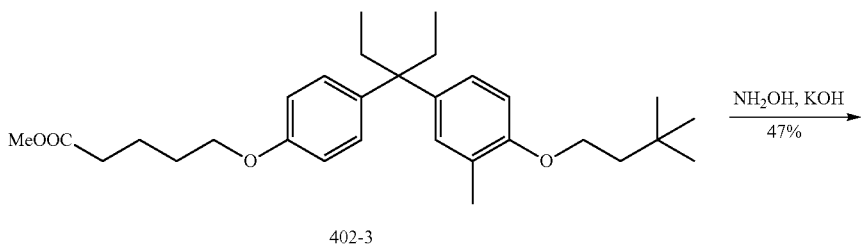

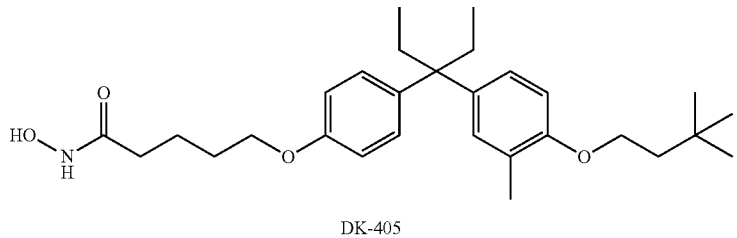

The compounds of the above scheme are characterized as follows:

4-(3-(4-(benzyloxy)phenyl)pentan-3-yl)-1-(3,3-dimethylbutoxy)-2-methylbenzene Compound 402-1: colourless oil: $R_f$ 0.90 (20:80 EtOac/Hex); IR (thin film) ν 3034, 2958, 2875, 1608, 1581, 1506, 1182 cm$^{-1}$; $^1$H NMR (500 MHz, CDCl$_3$) δ 7.45 (d, J=8.4 Hz, 2H), 7.39 (t, J=7.4 Hz, 2H), 7.33 (t, J=7.2 Hz, 1H), 7.10 (d, J=8.9 Hz, 2H), 6.96 (dd, J=8.5, 2.2 Hz, 1H), 6.90 (d, J=2.4 Hz, 1H), 6.88 (d, J=8.9 Hz, 2H), 6.71 (d, J=8.5 Hz, 1H), 5.04 (s, 2H), 4.00 (t, J=7.0 Hz, 2H), 2.19 (s, 3H), 2.05 (q, J=7.3 Hz, 4H), 1.74 (t, J=7.0 Hz, 2H), 0.99 (s, 9H), 0.62 (t, J=7.3 Hz, 6H) ppm; $^{13}$C NMR (75 MHz, CDCl$_3$) δ 156.4, 154.9, 141.6, 140.1, 137.3, 130.5, 129.1, 128.5, 127.9, 127.6, 126.0, 125.5, 113.7, 109.5, 70.0, 65.0, 48.5, 42.7, 29.9, 29.8, 29.4, 16.7, 8.5 ppm; HRMS (ESI) Calc. for C$_{31}$H$_{40}$O$_2$Na [M+Na]$^+$: 467.2921, found 467.2930.

4-(3-(4-(3,3-dimethylbutoxy)-3-methylphenyl)pentan-3-yl)phenol

Compound 402-2: colourless oil: $R_f$ 0.40 (20:80 EtOac/Hex); IR (thin film) ν 3378, 2958, 2876, 1610, 1506, 1178 cm$^{-1}$; $^1$H NMR (400 MHz, CDCl$_3$) δ 7.03 (d, J=8.8 Hz, 2H), 6.93 (d, J=8.2 Hz, 1H), 6.87 (s, 1H), 6.71 (m, 3H), 3.98 (t, J=7.0 Hz, 2H), 2.15 (s, 3H), 2.02 (q, J=7.4 Hz, 4H), 1.73 (t, J=7.0 Hz, 2H), 0.99 (s, 9H), 0.60 (t, J=7.3 Hz, 6H) ppm. $^{13}$C NMR (75 MHz, CDCl$_3$) δ 154.9, 152.9, 141.4, 140.1, 130.4, 129.2, 125.9, 125.5, 114.4, 109.5, 65.1, 48.4, 42.6, 29.8, 29.3, 16.7, 8.4 ppm; HRMS (ESI) Calc. for C$_{24}$H$_{34}$O$_2$Na [M+Na]$^+$: 377.2451, found 377.2468.

Methyl 5-(4-(3-(4-(3,3-dimethylbutoxy)-3-methylphenyl)pentan-3-yl)phenoxy)pentanoate Compound 402-3: colourless oil: $R_f$ 0.80 (20:80 EtOac/Hex); IR (thin film) ν 2957, 2869, 1741, 1606, 1508, 1245 cm$^{-1}$; $^1$H NMR (500 MHz, CDCl$_3$) δ 7.06 (d, J=9.0 Hz, 2H), 6.94 (dd, J=8.5, 2.2 Hz, 1H), 6.88 (d, J=3.0 Hz, 1H), 6.76 (d, J=8.9 Hz, 2H), 6.69 (d, J=8.5 Hz, 1H), 3.98 (t, J=7.0 Hz, 2H), 3.94 (t, J=5.9 Hz, 2H), 3.67 (s, 3H), 2.40 (t, J=5.9 Hz, 2H), 2.14 (s, 3H), 2.02 (q, J=7.3 Hz, 4H), 1.81 (m, 4H), 1.73 (t, J=7.0 Hz, 2H), 0.99 (s, 9H), 0.60 (t, J=7.3 Hz, 6H) ppm; $^{13}$C NMR (75 MHz, CDCl$_3$) δ 174.0, 156.4, 154.9, 141.2, 140.1, 130.5, 129.0, 126.0, 125.4, 113.3, 109.4, 67.1, 65.0, 51.5, 48.4, 42.7, 33.7, 29.8, 29.4, 28.8, 21.7, 16.7, 8.5 ppm;

5-(4-(3-(4-(3,3-dimethylbutoxy)-3-methylphenyl)pentan-3-yl)phenoxy)-N-hydroxypentanamide Compound DK-405: colourless film: IR (thin film) ν 3206, 2958, 2875, 1647, 1609, 1508, 1474, 1249 cm$^{-1}$; $^1$H NMR (500 MHz, cd$_3$od) δ 7.03 (d, J=6.9 Hz, 2H), 6.94 (d, J=8.6 Hz, 1H), 6.82 (s, 1H), 6.76 (d, J=6.9 Hz, 2H), 6.73 (d, J=8.6 Hz, 1H), 3.99 (t, J=6.9 Hz, 2H), 3.94 (t, J=5.8 Hz, 2H), 2.15 (t, J=7.0 Hz, 2H), 2.09 (s, 3H), 2.03 (q, J=7.3 Hz, 4H), 1.84-1.75 (m, 4H), 1.72 (t, J=6.9 Hz, 2H), 0.99 (s, 9H), 0.58 (t, J=7.3 Hz, 6H) ppm; $^{13}$C NMR (125 MHz, CDCl$_3$) δ 171.3, 156.7, 154.9, 140.9, 140.1, 130.1, 128.6, 125.8, 125.0, 113.1, 109.4, 66.9, 64.8, 42.4, 32.0, 29.2, 28.9, 28.9, 28.4, 22.1, 15.4, 7.4 ppm; LRMS (ESI) m/z 468.5 [M−H]$^-$.

EXAMPLE 44

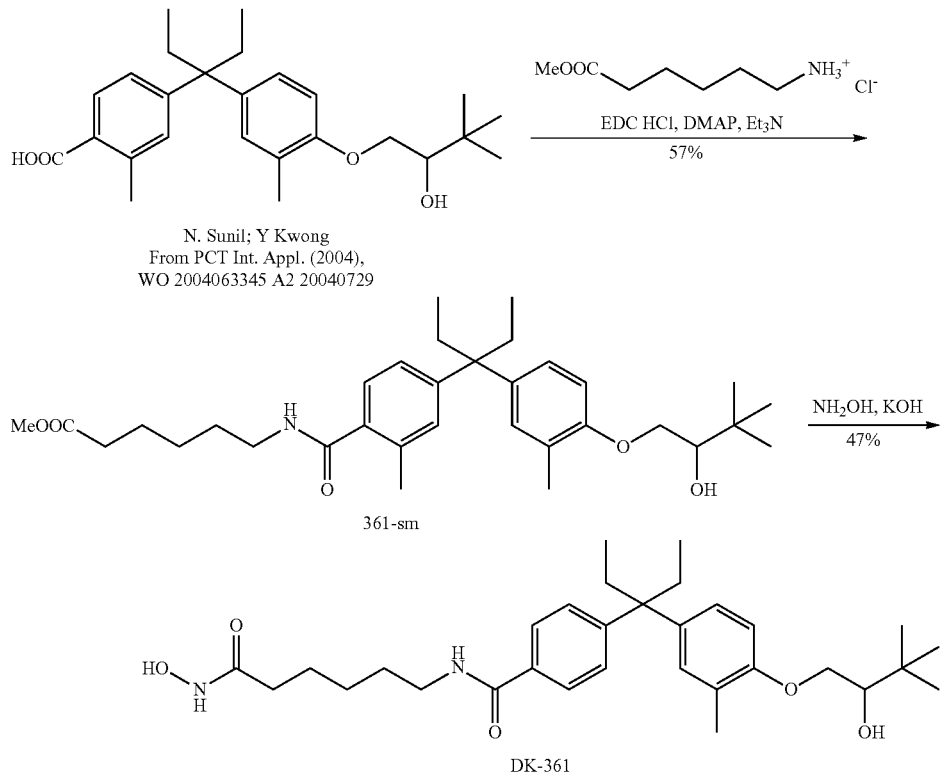

N. Sunil; Y Kwong
From PCT Int. Appl. (2004),
WO 2004063345 A2 20040729

The compounds of the above scheme are characterized as follows:

Compound DK-362 were prepared according to this scheme

Methyl 6-(4-(3-(4-(2-hydroxy-3,3-dimethylbutoxy)-3-methylphenyl)pentan-3-yl)-2-methylbenzamido)hexanoate Compound 361-sm: colourless oil: $R_f$ 0.30 (20:80 EtOac/Hex); IR (thin film) ν 3309, 2935, 2874, 1738, 1639, 1502, 1245 cm$^{-1}$; $^1$H NMR (400 MHz, CDCl$_3$) δ 7.20 (d, J=8.0 Hz, 1H), 7.01 (s, 1H), 6.98 (d, J=8.0 Hz, 1H), 6.94 (d, J=6.1 Hz, 1H), 6.86 (d, J=2.2 Hz, 1H), 6.69 (d, J=8.5 Hz, 1H), 5.73 (t, J=5.7 Hz, 1H), 4.09 (dd, J=9.2, 2.6 Hz, 1H), 3.85 (t, J=8.9 Hz, 1H), 3.66 (dd, J=8.7, 2.6 Hz, 1H), 3.66 (s, 3H), 3.41 (dd, J=13.2, 6.9 Hz, 2H), 2.39 (s, 3H), 2.33 (t, J=7.5 Hz, 2H), 2.16 (s, 3H), 2.04 (q, J=7.3 Hz, 4H), 1.75-1.55 (m, 4H), 1.45-1.32 (m, 2H), 1.01 (s, 9H), 0.59 (t, J=7.3 Hz, 6H) ppm; $^{13}$C NMR (75 MHz, CDCl$_3$) δ 174.0, 170.4, 154.5, 151.0, 140.4, 135.1, 133.5, 130.7, 130.6, 126.1, 125.65, 125.51, 110.1, 69.2, 51.5, 49.0, 39.5, 33.9, 33.6, 29.4, 29.0, 26.4, 26.1, 24.5, 20.2, 16.6, 8.3 ppm; HRMS (ESI) Calc. for C$_{33}$H$_{50}$O$_5$N [M+H]$^-$: 540.36835, found 540.36910.

4-(3-(4-(2-hydroxy-3,3-dimethylbutoxy)-3-methylphenyl)pentan-3-yl)-N-(6-(hydroxyamino)-6-oxohexyl)-2-methylbenzamide Compound DK-361: colourless film: IR (thin film) ν 3269, 2960, 2935, 2873, 1635, 1609, 1505, 1220 cm$^{-1}$; $^1$H NMR (500 MHz, CD$_3$OD) δ 7.21 (d, J=7.9 Hz, 1H), 7.04 (d, J=7.9 Hz, 1H), 7.03 (s, 1H) 6.98 (d, J=8.6 Hz, 1H), 6.80 (s, 1H), 6.76 (d, J=8.6 Hz, 1H), 4.11 (dd, J=10.0, 2.9 Hz, 1H), 3.86 (dd, J=10.0, 7.8 Hz, 1H), 3.61 (dd, J=7.7, 2.9 Hz, 1H), 3332 (t, J=7.0 Hz, 2H), 2.32 (s, 3H), 2.13 (s, 3H), 2.12-2.09 (m, 6H), 1.77-1.51 (m, 4H), 1.44-1.38 (m, 2H), 1.00 (s, 9H), 0.60 (t, J=7.3 Hz, 6H) ppm; $^{13}$C NMR (125 MHz, CD$_3$OD) δ 172.0, 155.0, 151.0, 139.8, 134.4, 133.8, 130.1, 130.1, 126.0, 125.6, 125.1, 109.8, 77.2, 69.5, 48.7, 39.1, 33.7, 32.2, 28.6, 28.4, 26.0, 25.2, 25.0, 18.6, 15.4, 7.2 ppm; HRMS (ESI) Calc. for C$_{31}$H$_{45}$O$_5$N$_2$ [M-H]$^-$: 539.34905, found: 539.35040; LRMS (ESI) m/z 541.5 [M+H]$^+$.

Methyl 7-(4-(3-(4-(2-hydroxy-3,3-dimethylbutoxy)-3-methylphenyl)pentan-3-yl)-2-methylbenzamido)heptanoate Compound 362-sm: colourless oil: $R_f$ 0.32 (20:80 EtOac/Hex); IR (thin film) ν 3309, 2926, 2857, 1738, 1639, 1608, 1536, 1461, 1246 cm$^{-1}$; $^1$H NMR (400 MHz, CDCl$_3$) δ 7.21 (d, J=8.0 Hz, 1H), 7.00 (s, 1H), 6.98 (d, J=8.0 Hz, 1H), 6.93 (d, J=6.1 Hz, 1H), 6.85 (d, J=2.2 Hz, 1H), 6.69 (d, J=8.5 Hz, 1H), 5.73 (t, J=5.7 Hz, 1H), 4.09 (dd, J=9.2, 2.6 Hz, 1H), 3.85 (t, J=8.9 Hz, 1H), 3.70 (dd, J=8.7, 2.6 Hz, 1H), 3.66 (s, 3H), 3.41 (dd, J=13.2, 6.9 Hz, 2H), 2.39 (s, 3H), 2.31 (t, J=7.5 Hz, 2H), 2.16 (s, 3H), 2.04 (q, J=7.3 Hz, 4H), 1.75-1.55 (m, 4H), 1.45-1.32 (m, 4H), 1.01 (s, 9H), 0.59 (t, J=7.3 Hz, 6H) ppm; $^{13}$C NMR (75 MHz, CDCl$_3$) δ 174.2, 170.3, 154.4, 151.0, 140.4, 135.1, 133.6, 130.6, 126.1, 125.7, 125.5, 110.1, 69.2, 51.5, 49.0, 39.7, 33.9, 33.6, 29.5, 29.0, 28.8, 26.6, 26.1, 24.8, 20.2, 16.6, 8.3 ppm; HRMS (ESI) Calc. for C$_{34}$H$_{52}$O$_5$N [M+H]$^+$: 554.38400, found 554.28423.

4-(3-(4-(2-hydroxy-3,3-dimethylbutoxy)-3-methyl-phenyl)pentan-3-yl)-N-(7-(hydroxyamino)-7-oxo-heptyl)-2-methylbenzamide
Compound DK-362: colourless film: $^1$H NMR (500 MHz, CD$_3$OD) δ 7.21 (d, J=7.9 Hz, 1H), 7.05 (d, J=7.9 Hz, 1H), 7.03 (s, 1H), 6.98 (dd, J=8.4, 2.4 Hz, 1H), 6.80 (s, 1H), 6.76 (d, J=8.4 Hz, 1H), 4.11 (dd, J=10.0, 2.9 Hz, 1H), 3.86 (dd, J=10.0, 7.8 Hz, 1H), 3.61 (dd, J=7.8, 2.9 Hz, 1H), 3.34 (s, 1H), 3.32 (t, J=7.3 Hz, 2H), 2.32 (s, 3H), 2.13 (s, 3H), 2.09 (, J=6.9 Hz, 4H), 2.07 (t, overlap, 2H), 1.78-1.50 (m, 4H), 1.48-1.29 (m, 4H), 1.00 (s, 9H), 0.60 (t, J=7.3 Hz, 6H) ppm; $^{13}$C NMR (75 MHz, CD$_3$OD) δ 172.0, 155.0, 151.0, 139.8, 134.4, 133.9, 130.1, 130.1, 126.0, 125.6, 125.1, 109.8, 77.2, 69.5, 48.7, 39.2, 33.7, 32.3, 28.8, 28.4, 28.3, 26.3, 25.2, 25.1, 18.5, 15.3, 7.2 ppm; LRMS (ESI) m/z 555.5 [M+H]$^+$.
EXAMPLE 45
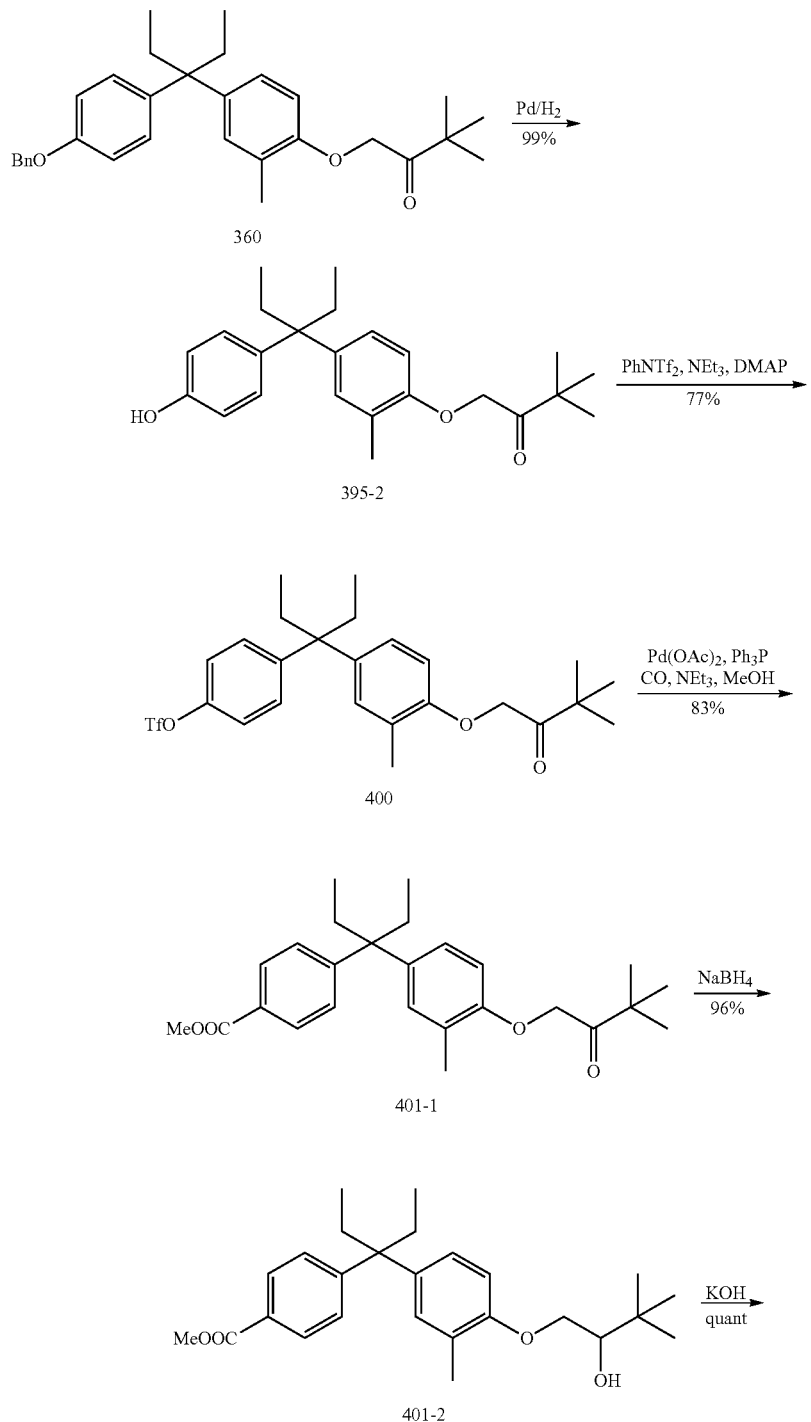

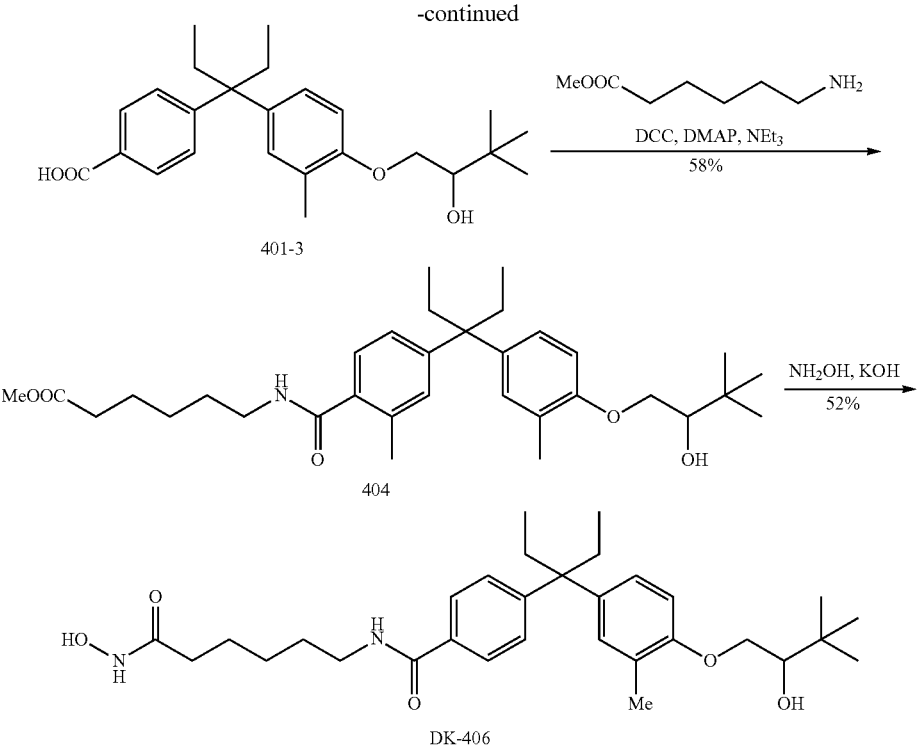

The compounds of the above scheme are characterized as follows:

1-(4-(3-(4-hydroxyphenyl)pentan-3-yl)-2-methyl-phenoxy)-3,3-dimethylbutan-2-one

Compound 395-2: yellow oil: R$_f$ 0.35 (20:80 EtOAc/Hex); IR (thin film) ν 3413, 2967, 2935, 2876, 1717, 1611, 1502, 1236, 1179 cm$^{-1}$; $^1$H NMR (400 MHz, CDCl$_3$) δ 7.00 (d, J=8.7 Hz, 2H), 6.93-6.87 (m, 2H), 6.70 (d, J=8.7 Hz, 2H), 6.49 (d, J=8.4 Hz, 1H), 5.32 (bs, 1H), 4.84 (s, 2H), 2.22 (s, 3H), 2.00 (q, J =7.3 Hz, 4H), 1.26 (s, 8H), 0.59 (t, J=7.3 Hz, 6H) ppm; $^{13}$C NMR (75 MHz, CDCl$_3$) δ 210.5, 153.9, 153.2, 141.5, 141.0, 130.8, 129.2, 126.1, 126.0, 114.4, 110.2, 69.6, 48.5, 43.3, 29.3, 26.4, 16.7, 8.4 ppm.

4-(3-(4-(3,3-dimethyl-2-oxobutoxy)-3-methylphenyl)pentan-3-yl)phenyl trifluoromethanesulfonate Compound 400: colourless oil: R$_f$ 0.80 (20:80 EtOAc/Hex); IR (thin film) ν 3202, 2971, 2880, 1717, 1599, 1204 cm$^{-1}$; $^1$H NMR (400 MHz, CDCl$_3$) δ 7.23 (d, J=9.0 Hz, 2H), 7.13 (d, J=8.9 Hz, 2H), 6.91-6.83 (m, 2H), 6.50 (d, J=8.2 Hz, 1H), 4.85 (s, 2H), 2.24 (s, 3H), 2.05 (q, J=7.3 Hz, 4H), 1.26 (s, 9H), 0.59 (t, J=7.3 Hz, 6H) ppm; $^{13}$C NMR (75 MHz, CDCl$_3$) δ 210.0, 154.3, 149.7, 147.3, 140.1, 130.6, 129.9, 126.4, 126.1, 120.3, 110.3, 69.4, 49.1, 43.2, 29.3, 26.5, 26.3, 16.6, 8.3 ppm.

Methyl 4-(3-(4-(3,3-dimethyl-2-oxobutoxy)-3-methylphenyl)pentan-3-yl)benzoate

Compound 401-1: colourless oil: R$_f$ 0.67 (20:80 EtOAc/Hex); IR (thin film) ν 2968, 2879, 1722, 1608, 1501, 1281, 1143 cm$^{-1}$; $^1$H NMR (300 MHz, CDCl$_3$) δ 7.90 (d, J=8.4 Hz, 2H), 7.24 (d, J=8.4 Hz, 2H), 6.94-6.76 (m, 2H), 6.49 (d, J=9.2 Hz, 1H), 4.83 (s, 2H), 3.89 (s, 3H), 2.21 (s, 3H), 2.07 (q, J=7.2 Hz, 4H), 1.25 (s, 9H), 0.59 (t, J=7.3 Hz, 6H) ppm; $^{13}$C NMR (75 MHz, CDCl$_3$) δ 210.3, 167.4, 154.8, 154.2, 140.4, 130.7, 129.6, 129.0, 128.2, 127.2, 126.3, 126.0, 123.5, 110.3, 69.5, 52.0, 49.5, 43.2, 29.1, 26.3, 16.6, 8.3 ppm.

Methyl 4-(3-(4-(2-hydroxy-3,3-dimethylbutoxy)-3-methylphenyl)pentan-3-yl)benzoate Compound 401-2: colourless oil: R$_f$ 0.65 (20:80 EtOAc/Hex); IR (thin film) ν 3523, 2962, 2877, 1721, 1609, 1505, 1115 cm$^{-1}$; $^1$H NMR (500 MHz, CDCl$_3$) δ 7.91 (d, J=8.7 Hz, 2H), 7.24 (d, J=8.7 Hz, 2H), 6.93 (d, J=8.5 Hz, 1H), 6.86 (s, 1H), 6.71 (d, J=8.5 Hz, 1H), 4.09 (dd, J=9.2, 2.7 Hz, 1H), 3.89 (s, 3H), 3.85 (t, J=9.0 Hz, 1H), 3.70 (dd, J=9.2, 2.7 Hz, 1H), 2.46 (d, J=2.9 Hz, 1H), 2.16 (s, 3H), 2.09 (q, J=7.4 Hz, 4H), 1.01 (s, 9H), 0.60 (t, J=7.3 Hz, 6H) ppm; $^{13}$C NMR (125 MHz, CDCl$_3$) δ 167.2, 154.7, 154.6, 140.1, 130.6, 128.9, 128.1, 127.2, 126.1, 125.81, 110.2, 69.2, 51.9, 49.5, 33.6, 29.1, 26.1, 16.6, 8.3 ppm.

4-(3-(4-(2-hydroxy-3,3-dimethylbutoxy)-3-methylphenyl)pentan-3-yl)benzoic acid

Compound 401-3: colourless oil: R$_f$ 0.29 (40:60 EtOAc/Hex); IR (thin film) ν 3413, 2964, 2877, 2667, 2552, 1682, 1505, 1245, cm$^{-1}$; $^1$H NMR (300 MHz, CDCl$_3$) δ 7.99 (d, J=8.3 Hz, 1H), 7.29 (d, J=8.4 Hz, 1H), 6.94 (d, J=8.5 Hz, 1H), 6.87 (s, 1H), 6.72 (d, J=8.5 Hz, 1H), 4.10 (dd, J=9.1, 2.3 Hz, 1H), 3.87 (t, J=8.9 Hz, 1H), 3.72 (dd, J=8.6, 2.3 Hz, 1H), 2.17 (s, 1H), 2.11 (q, J=7.1 Hz, 2H), 1.02 (s, 4H), 0.62 (t, J=7.1 Hz, 3H) ppm; $^{13}$C NMR (75 MHz, cdcl$_3$) δ 172.1, 155.8, 154.6, 140.0, 130.6, 129.6, 128.2, 126.4, 126.1, 125.9, 110.3, 69.2, 49.6, 33.6, 29.1, 26.1, 16.6, 8.3 ppm.

Methyl 6-(4-(3-(4-(2-hydroxy-3,3-dimethylbutoxy)-3-methylphenyl)pentan-3-yl)benzamido)hexanoate Compound 404: colourless oil: $R_f$ 0.30 (20:80 EtOac/Hex); IR (thin film) ν 3336, 2938, 2875, 1737, 1637, 1500, 1245 cm$^{-1}$; $^1$H NMR (500 MHz, CDCl$_3$) δ 7.63 (d, J=8.4 Hz, 2H), 7.22 (d, J=8.4 Hz, 2H), 6.93 (d, J=8.3 Hz, 1H), 6.84 (s, 1H), 6.69 (d, J=8.3 Hz, 1H), 6.12 (t, J=5.7 Hz, 1H), 4.08 (dd, J=10.0, 3.0 Hz, 1H), 3.85 (t, J=9.1 Hz, 1H), 3.70 (dd, J=9.1 and 3.0 Hz, 1H), 3.66 (s, 3H), 3.45 (q, J=6.6 Hz, 2H), 2.33 (t, J=6.6 Hz, 2H), 2.15 (s, 3H), 2.08 (q, J=7.9 Hz, 4H), 1.72-1.52 (m, 4H), 1.46-1.35 (m, 2H), 1.00 (s, 9H), 0.60 (t, J=7.9 Hz, 6H) ppm; $^{13}$C NMR (125 MHz, CDCl$_3$) δ 174.1, 167.6, 154.5, 152.9, 140.2, 131.8, 130.6, 128.3, 126.2, 126.1, 125.8, 110.2, 69.2, 51.5, 49.4, 39.7, 33.8, 33.6, 29.3, 29.1, 26.4, 26.1, 24.4, 16.6, 8.3 ppm.

4-(3-(4-(2-hydroxy-3,3-dimethylbutoxy)-3-methylphenyl)pentan-3-yl)-N-(6-(hydroxyamino)-6-oxohexyl)benzamide Compound DK-406: colourless film: IR (thin film) ν 3294, 2960, 2865, 1633, 1500, 1275, 1259 cm$^{-1}$; $^1$H NMR (300 MHz, CD$_3$OD) δ 7.68 (d, J=8.4 Hz, 2H), 7.25 (d, J=8.3 Hz, 2H), 6.97 (d, J=8.3 Hz, 1H), 6.84 (s, 1H), 6.78 (d, J=8.3 Hz, 1H), 4.11 (dd, J=10.0, 3.0 Hz, 1H), 3.86 (dd, J=9.5 and 7.5 Hz, 1H), 3.61 (dd, J=7.5 and 2.8 Hz, 1H), 3.36 (t, J=7.5 Hz, 1H), 2.17-2.06 (m, 9H), 1.71-1.57 (m, 4H), 1.44-1.34 (m, 2H), 0.99 (s, 9H), 0.61 (t, J=7.1 Hz, 6H) ppm; $^{13}$C NMR (75 MHz, CD$_3$OD) δ 171.5, 155.1, 153.2, 139.5, 131.4, 130.1, 127.9, 126.2, 125.8, 125.7, 109.9, 77.2, 69.5, 49.0, 46.7, 39.3, 33.7, 32.2, 28.8, 28.6, 26.1, 25.2, 25.0, 15.3, 7.2 ppm; HRMS (ESI) Calc. for $C_{31}H_{45}O_5N_2$ [M−H]$^−$: 525.33340, found: 525.33398; LRMS (ESI) m/z 527.5 [M+H]$^+$.

The compounds described herein have several advantages. They can be prepared in 5-10 steps from inexpensive starting materials which is interesting from an industrial synthesis standpoint. In addition, because they differ structurally from 1,25D they are very likely to be resistance to catabolism by CYP24 activity, which is strongly induced by VDR agonists.

Biology Experimental Protocols

Cell culture. Human head and neck squamous carcinoma cell lines SCC4 and SCC45 and mouse HNSCC line AT84 were purchased from American Type Culture Collection (Manassas, Va.) and cultured under recommended conditions. Cells were split at 60-70% confluence, as follows: cells were washed with filtered PBS, split with a 5-10 min incubation with 1 ml Trypsin-EDTA (Invitrogen, Carlsbad, Calif.) in PBS, collected with medium. Following centrifugation, the supernatant was removed. Cell pellets were resuspended with DMEM-F12, and distributed on fresh media-containing dishes. For treatments, AT84 cells were split and 24 h later medium was changed to DMEM+10% charcoal-stripped FBS. 24 h after that media was changed and cells were incubated in DMEM-F12+10% charcoal-stripped FBS and 1,25D (Sigma) or hybrid compounds, as indicated in the figures.

RNA isolation and RT/PCR analysis. PCR primers against CYP24 (forward, 5',5'-ggcaacagttctgggtgaat, reverse, 5'-tatttgeggacaatccaaca) were designed using Primer3 software as described and used in Tavera-Mendoza, Quach, T., Dabbas, B., Hudon, J., Liao, X., Palijan, A., Gleason, J. L., and White, J. H. (2008) Incorporation of histone deacetylase inhibition into the structure of a nuclear receptor agonist. *Proc. Nat. Acad. Sci. U.S.A.* 105, 8250-55. and Lamblin, M. et al *Bioorganic & Medicinal Chemistry* (2010) 18:4119-4137. After treatment, cells were washed with PBS, homogenized with 1 ml TRIzol Reagent (Invitrogen, Carlsbad, Calif.), kept at room temperature for 2-5 min, collected and kept at −80° C. for at least 1 h. After, thawing 0.2 ml chloroform was added. After vigorous mixing and storing for 10 min, mixtures were centrifuged (10,000 rpm, 15 min, 4° C.) and the upper transparent layer was transferred to a new tube. 0.5 ml isopropanol was added and the new solution was mixed. After centrifuging at 4° C., the supernatant was discarded and 1 ml of 75% ethanol was added. After centrifuging and discarding the supernatant, the pellet was air-dried for 5-10 min, and then dissolved in ddH2O. RNA concentrations were measured using a spectrophotometer, and 1-3 μg of RNA were loaded for reverse transcriptase reactions (total volume: 20 μl). 80 μl of ddH2O was added to the RT-product, and 1.5 μl of that was used as template for the PCR reaction. Reverse transcriptase (Super Script II) was purchased from Invitrogen (Carlsbad, Calif.). DNA polymerase and dNTP's were ordered from Fermentas (Glen Burnie, Md.).

Chromatin immunoprecipitation assays. ChIP assays were performed with sonicated extracts of SCC25 cells as described (see Wang, T.-T. et al. *J Immunol* (2004) 173: 2909-2912). Cells were treated for 1 h with 1,25D (100 nM), or vehicle. Immunoprecipitations were performed using normal rabbit IgG, anti-VDR antibody (c-20) (Santa Cruz Biotechnology, Santa Cruz, Calif.). The CYP24 promoter region was amplified with the following primers: forward, 5'-cgaagcacacccggtgaact, and reverse, 5'-ccaatgagcaegeagaggag.

Fluorescence polarization (FP) competition assay. The assay was performed using a vitamin D receptor competitor assay kit (Polarscreen, Invitrogen, Carlsbad, Calif.) set up using 0.5 nM fluorescent tracer. The assay measures the decrease in FP accompanying loss of binding to the relatively high molecular weight VDR ligand binding domain of the fluorescent tracer due to the presence of a competitor. FP was measured using an Analyst HT fluorimeter (Molecular Devices) configured with absorption and emissions filters as recommended by the kit manufacturers. Dose response curves and IC50 determination were determined using XLfit (IDBS) Sigmoidal Dose-Response Model [fit=(A+((B−A)/(1+((C/x)^D)))); inv=(C/(((((B−A)/(y−A))−1)^(1/D))); res=(y−fit)]. Note that use of concentrations of some analogues at 1 mM or greater was precluded in the assay likely due to their insolubility under assay conditions.

Fluorogenic HDAC inhibition assay. Boc-Lys(Ac)-7-amino-4-methylcoumarin (Boc-Lys(Ac)-AMC) was used as substrate for the HDAC assays. Substrate solution was prepared as follow: Boc(Lys-Ac)-AMC was dissolved in DMSO and diluted with HDAC buffer (15 mM Tris-HCl [pH 8.1], 250 μM EDTA, 250 mM NaCl, 10% glycerol) to give 1 mM solutions containing 1.7% DMSO. Trypsin was used to stop the reaction, releasing free AMC. The trypsin solution was prepared as follow: trypsin was dissolved in HDAC buffer to give a concentration of 10 mg/mL. Release of AMC was monitored by measuring the fluorescence at 460 nm (lex=390 nm) with a microplate reader (SpectraMax Gemini) at 37° C. The AMC signals were recorded against a blank with buffer, substrate and trypsin but without the enzyme. All experiments were carried out at least in triplicate.

For standard HDAC assays, 50 μL of HDAC buffer was mixed with 10 μL of diluted enzyme solution in HDAC buffer at room temperature. The HDAC reaction was started by adding 40 μL of substrate solution in HDAC buffer followed by 30 min of incubation with stirring at 37° C. The reaction was stopped by adding 100 µL of trypsin solution. After a 10 min incubation with stirring at 37° C., the release of AMC was monitored by measuring the fluorescence.

For HDAC inhibition assays, inhibitor diluted in 50 µL of HDAC buffer was mixed with 10 µL of diluted enzyme solution in HDAC buffer at room temperature. The HDAC reaction was started by adding 40 µL of substrate solution in HDAC buffer followed by 30 min of incubation with stirring at 37° C. The reaction was stopped by adding 100 µL, of trypsin solution. After a 10 min incubation with stirring at 37° C., the release of AMC was monitored by measuring the fluorescence.

EdU Cell Growth Assay. Click-iT EdU Alexa Fluor high-throughput imaging (HCS) assay for cell proliferation. HCS assays were performed on AT84 mouse squamous carcinoma cell line (ATCC) following the manufacturer's instruction (Molecular Probes, Invitrogen). Images were analyzed for Hoechst 33342 (350/460 nm) and Alexa Fluro 647 (620/700 nm) using Image Xpress Micro (Molecular Devices, CA, USA). All samples were in triplicate.

Expression and Purification of the zVDR. The LBD of the zebrafish VDR (residues 156-453) in pET28b expression vector was over-produced in *E. coli* BL21 (DE3) strain. Cells were grown in LB medium and subsequently incubated for three hours at 25° C. with 1 mM isopropyl thio-β-D-galactoside. The protein purification included a metal affinity chromatography step on a cobalt-chelating resin (TALON, Clontech). The tag was removed by thrombin digestion at 4° C., and the protein was further purified by gel filtration on a Superdex 5200 16/60 column. The protein buffer prior to concentration of the protein contains 20 mM Tris, pH 7.5, 200 mM NaCl, and 2 mM TCEP. The protein was concentrated to 3.5 mg/ml and incubated in the presence of a 3-fold excess of ligand and SRC-1 peptide (686-RHKILHRLLQEGSPS-700). The purity and homogeneity of the protein were assessed by SDS-PAGE. Crystals of complexes were obtained at 17° C. by vapor diffusion method. The reservoir solution contained BisTris 0.1M pH 6.5, lithium sulfate 1.6M and magnesium sulfate 50 mM.

The chemical structure of certain compounds referred to in the following discussion are illustrated in the following table.

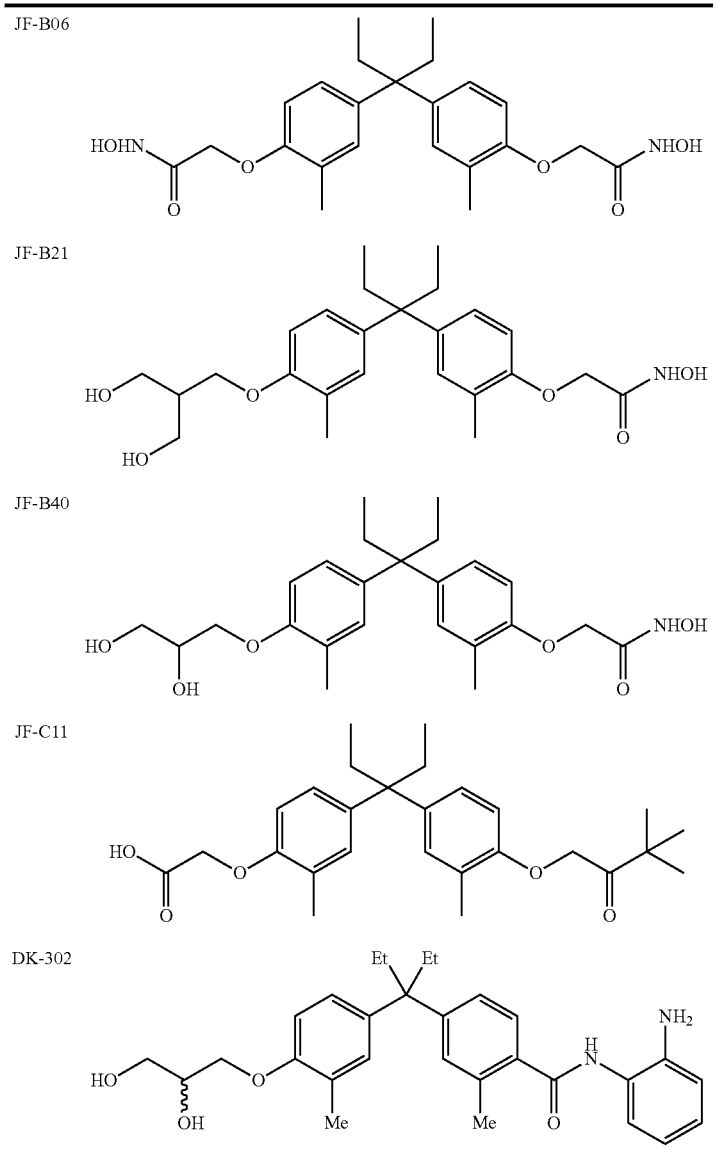

Test compounds (10 µM) were first screened for VDR agonism by analysis of induction of CYP24 gene expression in 1,25D-sensitive human SCC25 cells. CYP24 was chosen because its expression is highly induced and exquisitely sensitive to the presence of hormonal vitamin D. Only compound JF-B01 showed any agonist activity against VDR (FIG. 1a). In contrast, compounds JF-B21, JF-B40 and compound JF-B52, as well as symmetric JF-B06, were completely inactive as VDR agonists at 10 µM. compound JF-B01 is an efficacious agonist, with a potency equal to or greater than that of LG190178, and approximately 10-fold lower than that of 1,25D (FIG. 1 b). The carboxylic acid JF-C11 also showed some agonist activity.

Figure 1B:
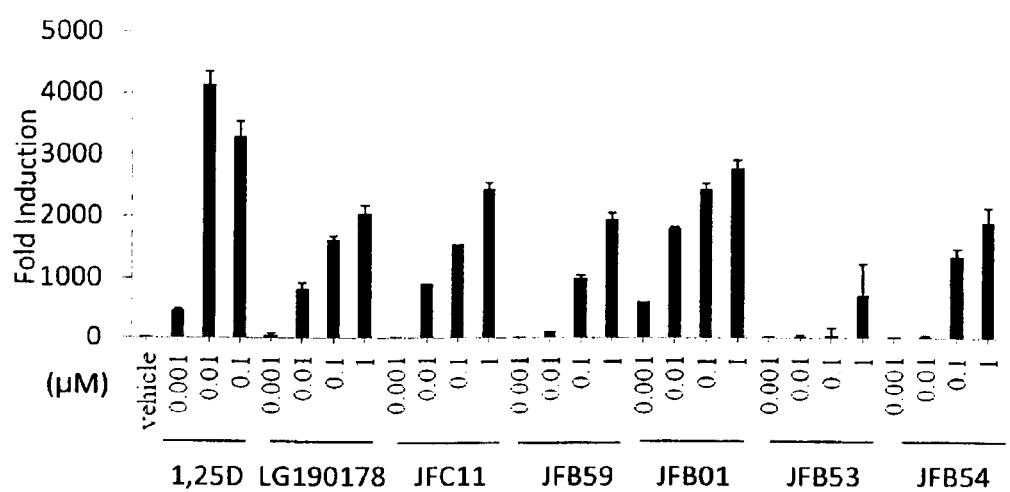
Figure 1C:
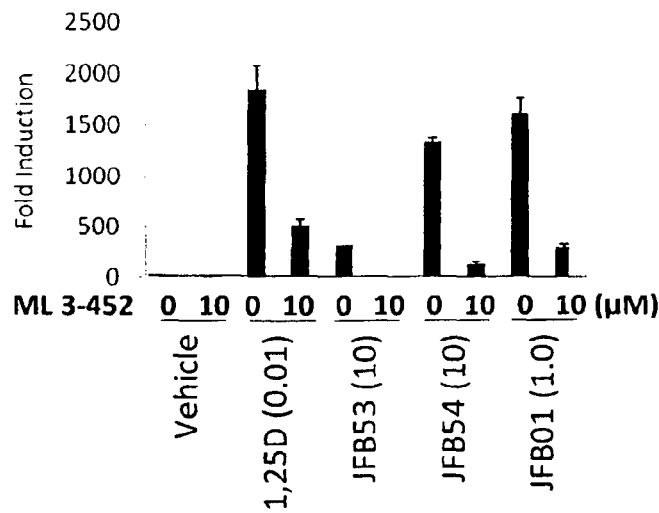
Figure 1D:
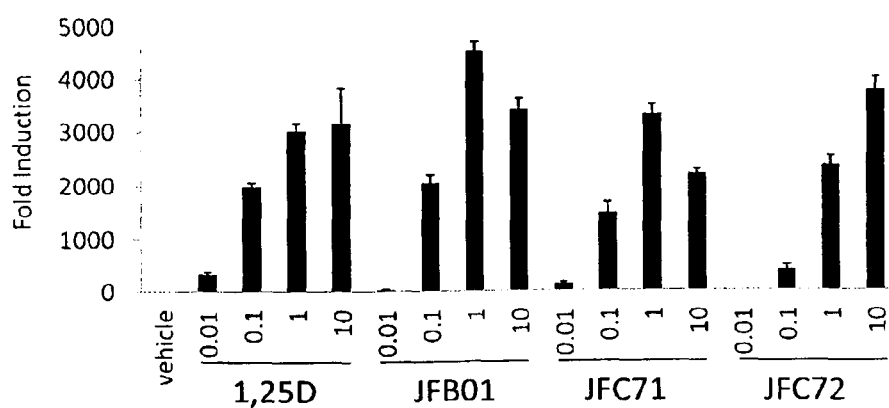
Figure 1E:
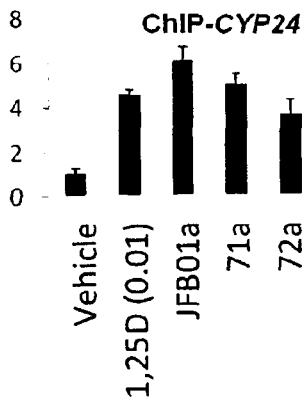
FIG. 1*e* is the chromatin immunoprecipitation (ChIP) assay obtained for certain compounds.
Figure 1F:
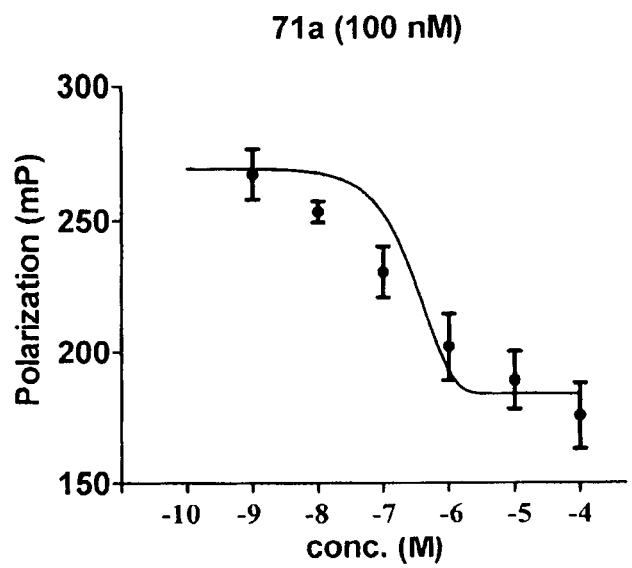
FIGS. 1*f* and 1*g*: represents two compounds described herein (JF-C71 and -C72) compete for binding of a fluorescent tracer to the VDR ligand binding domain with apparent IC50's measured by fluorescence polarization assay.
Figure 1G:
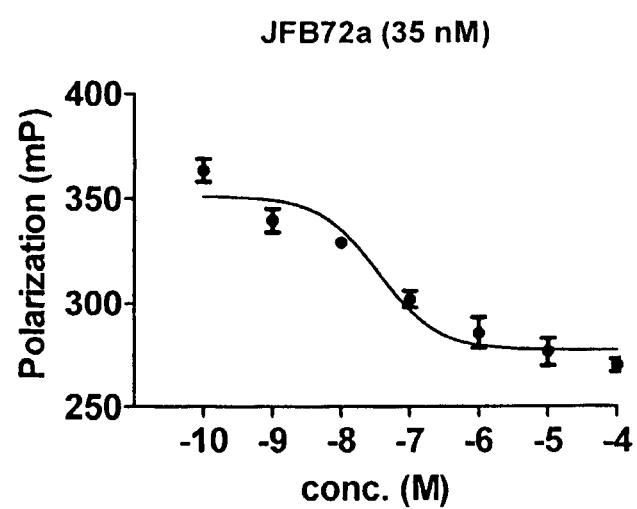

Compared to compound JF-B01 it's the ketone compound JF-B59 functioned with a >10-fold lower potency (FIG. 1b). Similarly, compounds compound JF-B53 and compound JF-B54 also showed VDR agonist activity, but with reduced potency (FIG. 1b). Consistent with binding to the VDR, induction of CYP24 by compound JF-B01, compound JF-B53 or compound 16 (JF-B54) was blocked (FIG. 1 c).

Compounds JF-C71 and JF-C72 both proved to be VDR agonists with similar potencies (FIG. 1d), suggesting that the sidechain can adopt multiple binding conformations in the VDR ligand binding pocket. Moreover, both enantiomers induced binding of the VDR to the vitamin D response element located in the proximal promoter of the CYP24 gene, as assessed by chromatin immunoprecipitation (ChIP) assay (FIG. 1e), consistent with their function as VDR agonists. Direct binding to the VDR of compounds JF-C71 and JF-C72 was confirmed by a fluorescence polarization competition assay which showed a binding with an IC50 of approximately 100 and 35 nM (FIG. 1 d), respectively, or less than one order of magnitude lower than the 13 nM IC50 of 1,25D in this assay and in excellent agreement with studies of VDR agonism above.

Compounds were tested for their capacity to inhibit purified class I HDAC3 and class 11 enzyme HDAC6 in vitro using SAHA as a positive control. Compounds tested inhibited HDAC3 in vitro with IC50s between 17 and 36 µM, which compares very favourably with the IC50 of triciferol for this enzyme (13.3 µM;), but about 500- to 1000-fold lower than that of SAHA (see Table 1). IC50s for inhibition of HDAC6 in vitro were in a very similar range at around 30 µM, or 50-fold lower than SAHA, with the possible exception of JF-B06 having two hydroxamic ZBGs groups for which the IC50 for HDAC was 4.7 µM. It is possible that the hydroxamic acid replacing the 2-hydroxy-3,3-dimethylbutyl group in LG-190178 may confer somewhat higher potency for inhibition of HDAC6. Other compounds in table 1 below were also tested. Subsequent studies showed it was possible to modulate the potency for HDAC and VDR agonism by altering the aromatic ring and linking chain bearing the hydroxamic acid unit.

TABLE 1

| Compound | HDAC3 | HDAC6 |
|---|---|---|
| SAHA | 33.8 nM | 580 nM |
| JF-B06 | — | 4.7 µM |
| JF-B21 | 36.1 µM | 37.9 µM |
| JF-B53 | 17.0 µM | 33.3 µM |
| JF-B54 | 29.9 µM | 31.5 µM |
| JF-C71 | 22.0 µM | 26.1 µM |
| JFD-15 | 9.83 µM | 47.1 µM |
| JFD-50 | 45.1 µM | 36.1 µM |
| DK-178 | 47.3 µM | 24.9 µM |
| DK-201 | 30.5 µM | — |

TABLE 1-continued

| Compound | HDAC3 | HDAC6 |
|---|---|---|
| DK-305 | — | 29.2 uM |
| DK-319 | — | 2.65 µM |
| DK-320 | — | 5.03 µM |
| DK-347 | — | 3.94 µM |
| DK-361 | — | 3.40 µM |
| DK-362 | — | 1.08 µM |
| DK-366 | — | 6.60-8.20 µM |
| DK-367 | — | 1.57 µM |
| DK-381 | — | 3.13 µM |
| DK-405 | — | 1.97 uM |
| DK-406 | — | 557 nM |

Figure 2A:
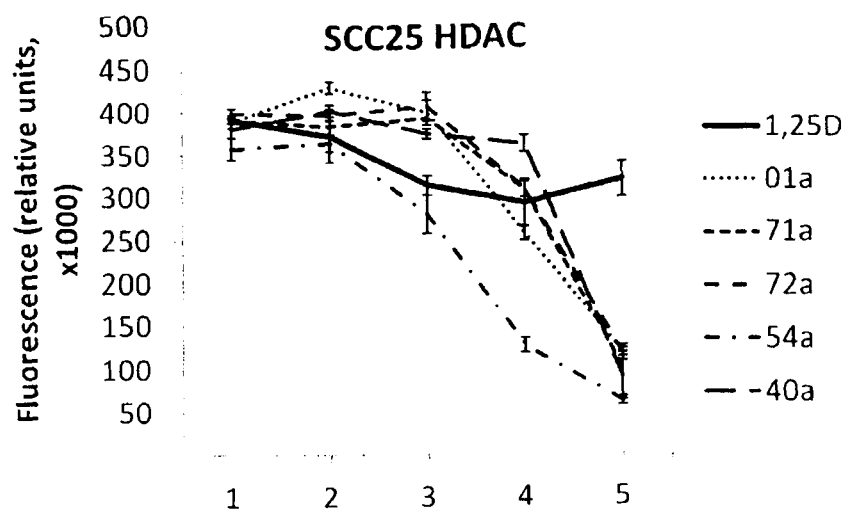
FIG. 2*a-b* is a representation of HDACi activity of certain compounds measured in live SCC25 or SCC4 cells.
Figure 2B:
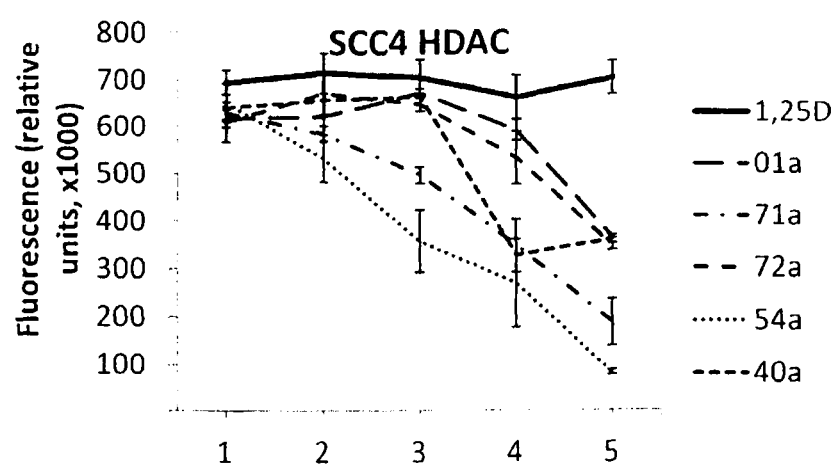

Compounds were also tested along with 1,25D for HDACi activity using a fluorogenic substrate in vivo in SCC25 and SCC4 cells (FIGS. 2a, b). This assay measures the inhibition of total intracellular HDAC activity and determines the capacity of compounds to inhibit HDACs in the form of their naturally occurring complexes. While an increasing concentration of 1,25D had no effect on substrate deacetylation in either cell line, all compounds tested displayed dose-dependent HDAC inhibition, with compound JF-B54 being the most potent.

Figure 2C:
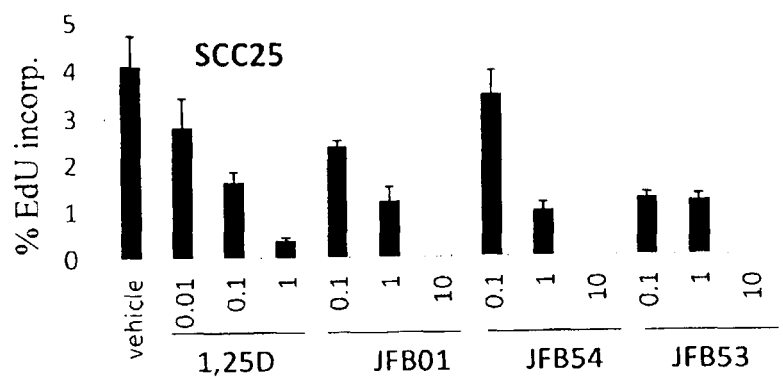
FIG. 2*c-f*: represent the dose-dependent antiproliferative activities by measuring incorporation of fluorescent nucleoside analogue EdU in 1,25D-sensitive SCC25 cells, AT84 cells or 1,25D-resistant SCC4 cells.
Figure 2D:
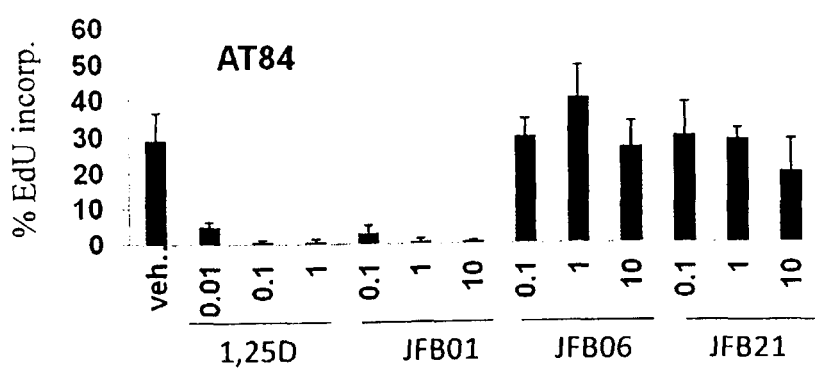
Figure 2E:
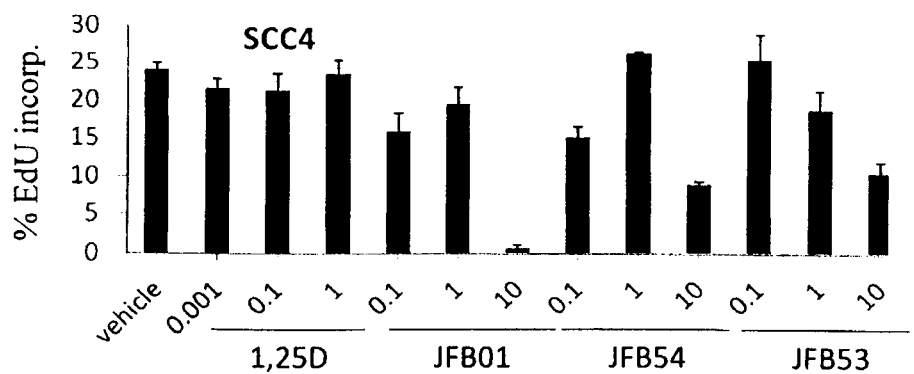
Figure 2F:
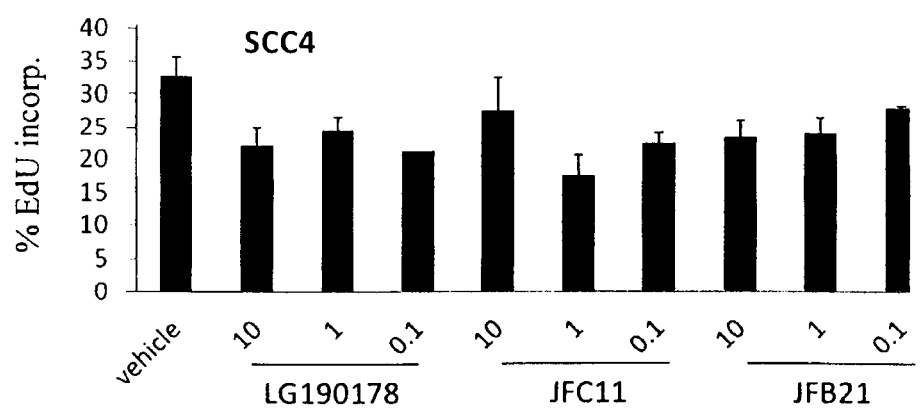
Figure 3A:
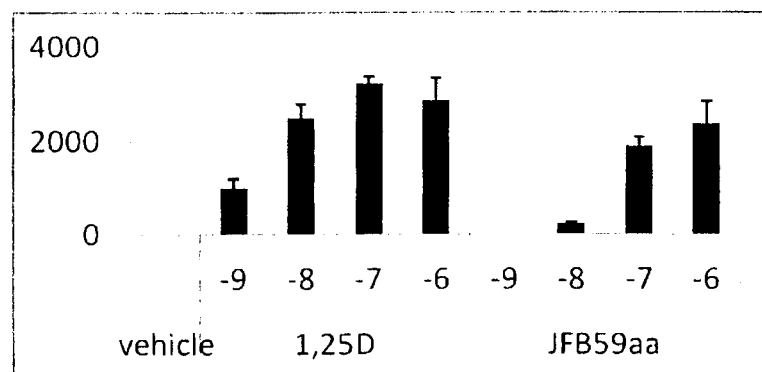
FIGS. 3 to 5 are representations of the activity in a VDR agonism model by analysis of induction of CYP24 gene expression in 1,25D-sensitive human SCC25 cells.
Figure 3B:
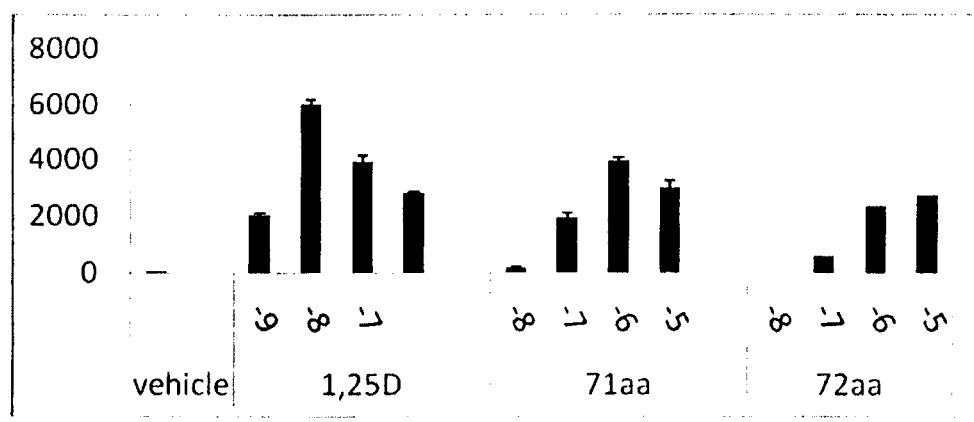
Figure 3C:
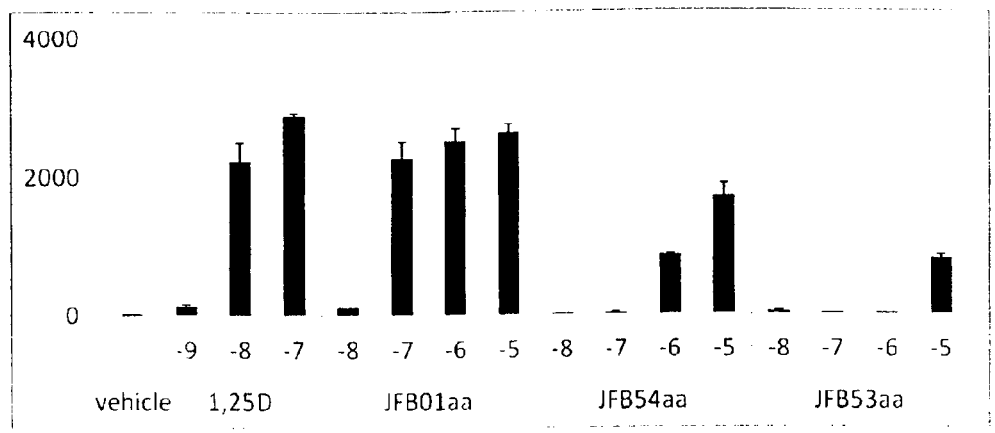
Figure 3D:
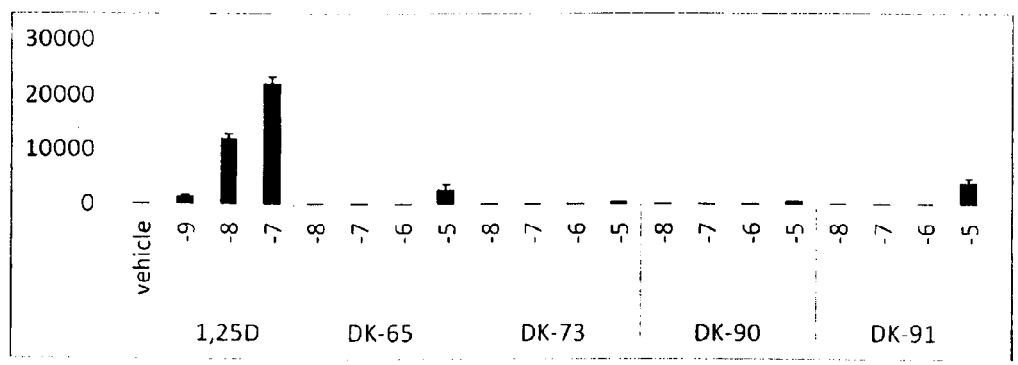
Figure 4A:
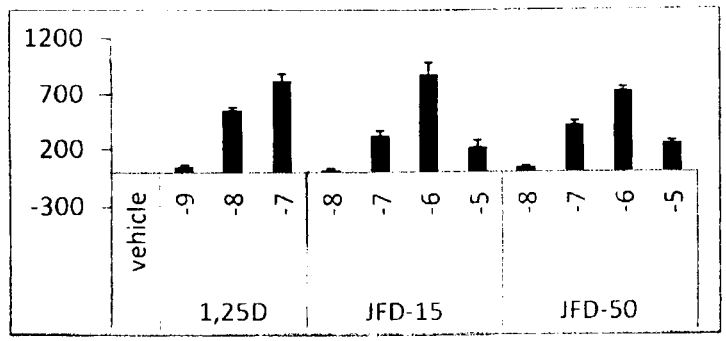
Figure 4B:
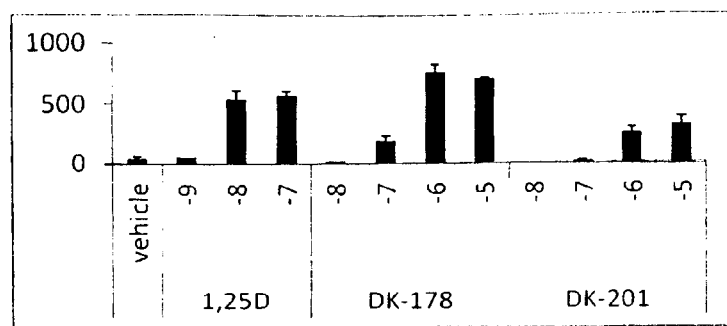
Figure 4C:
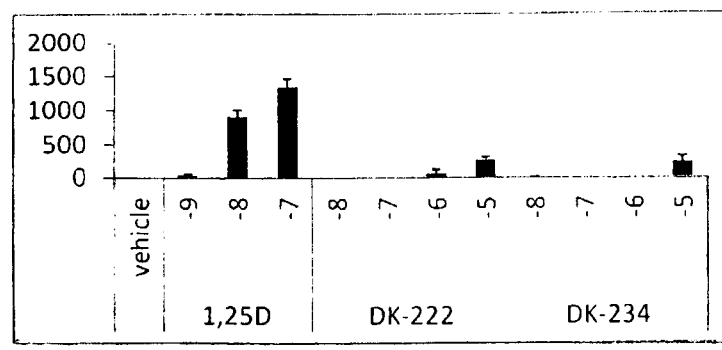
Figure 4D:
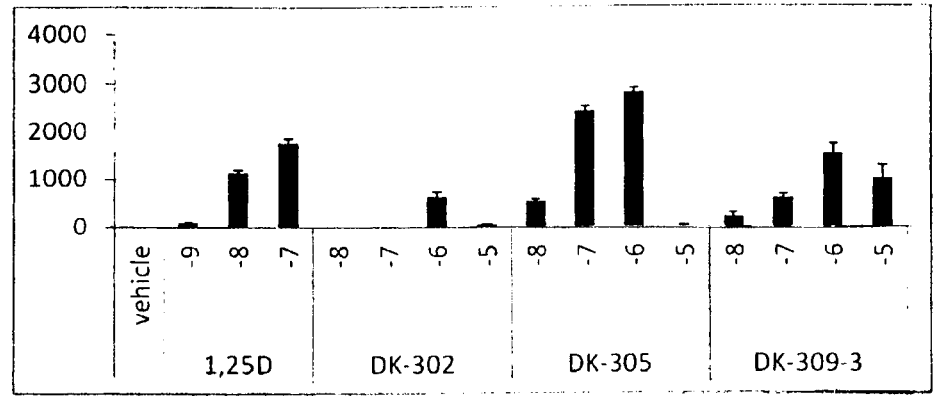
Figure 5A:
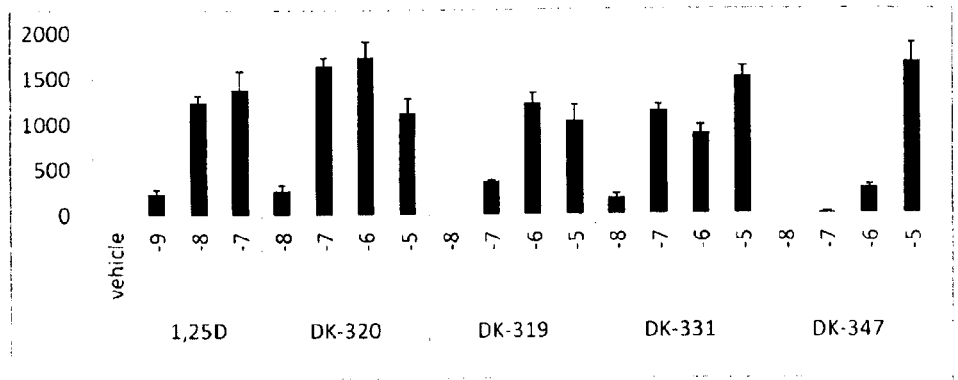
Figure 5B:
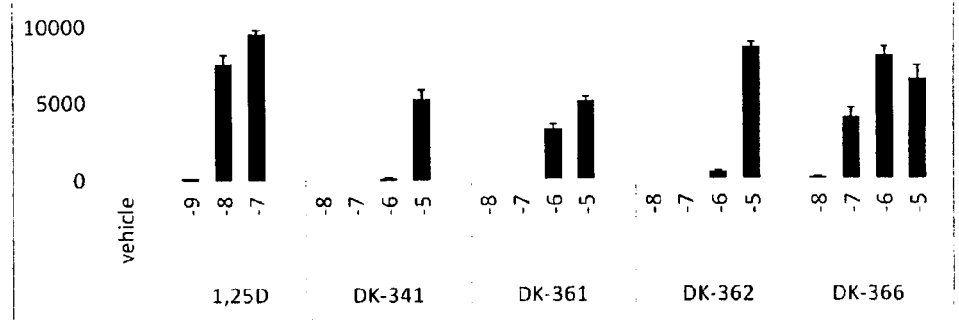
Figure 5D:
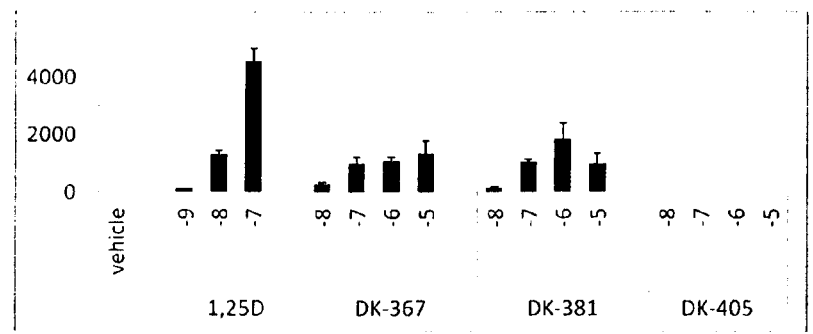
Figure 5C:
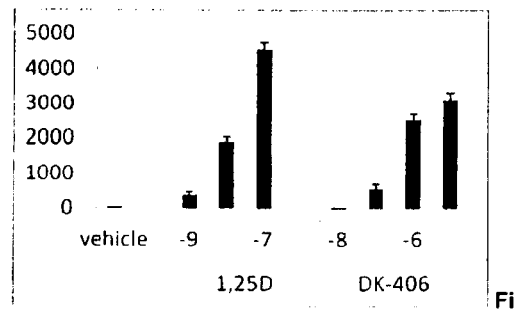
Figure 6A:
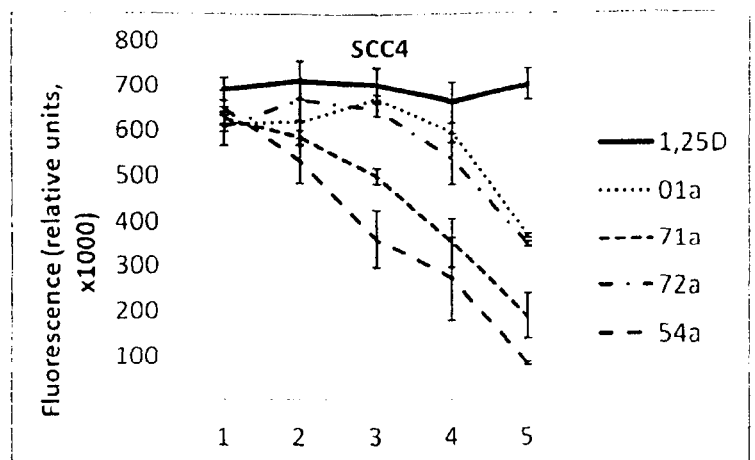
FIGS. 6 and 7*a-b* are representations of HDACi activity of certain compounds measured in live SCC25 or SCC4 cells.
Figure 6B:
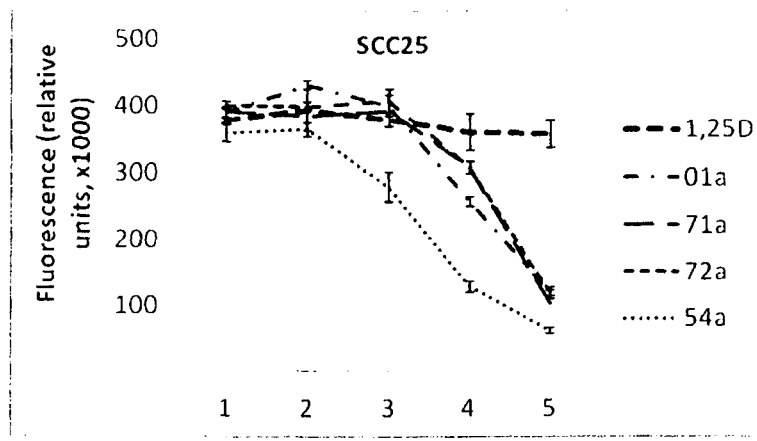
Figure 6C:
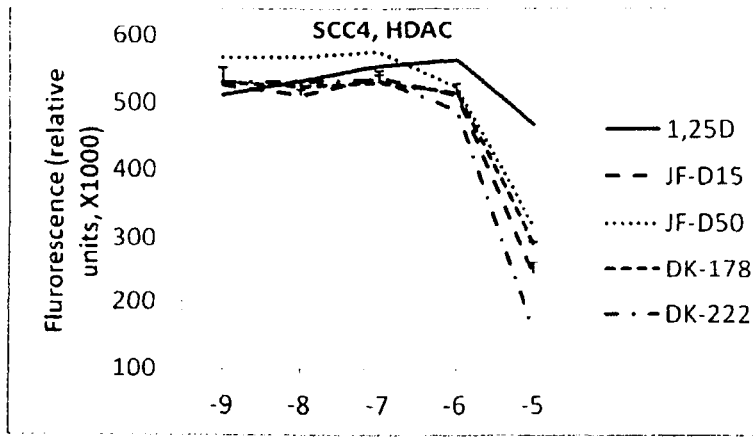
Figure 6D:
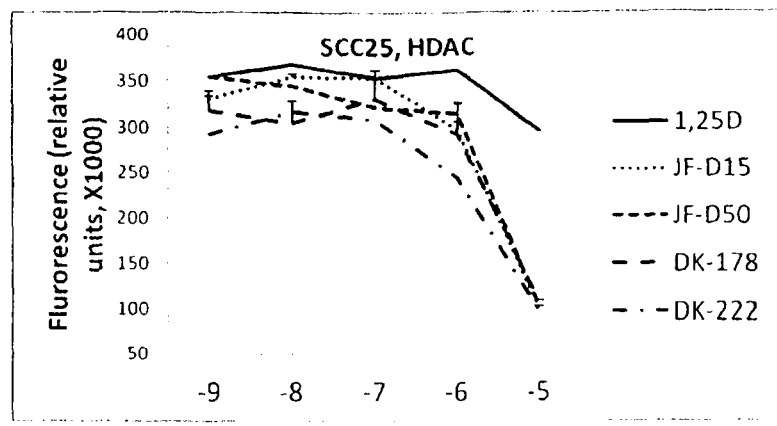
Figure 6E:
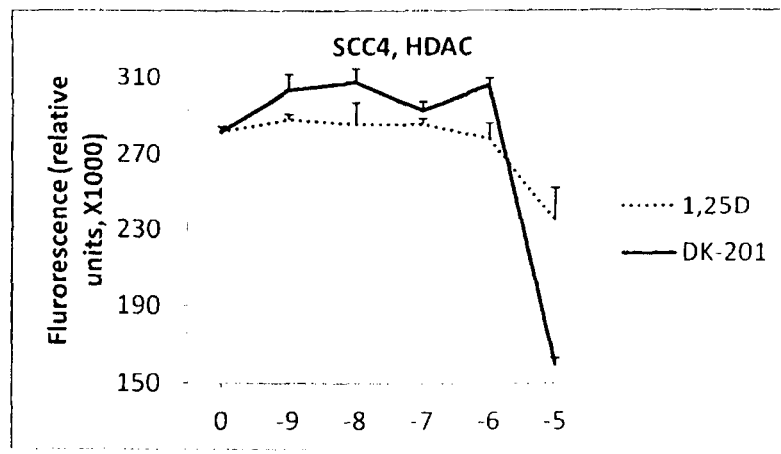
Figure 6F:
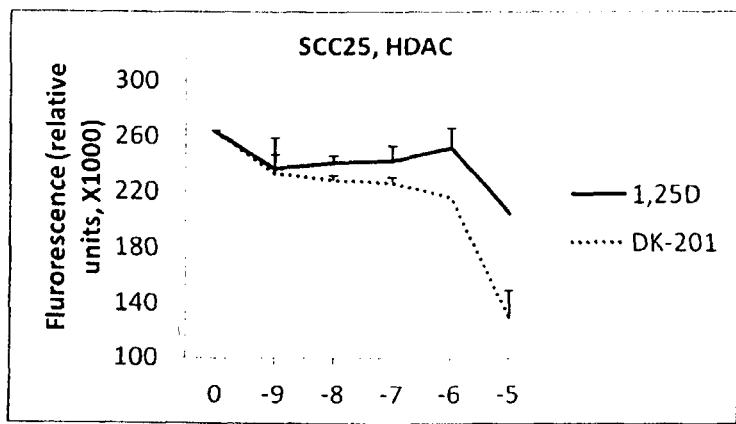
Figure 6G:
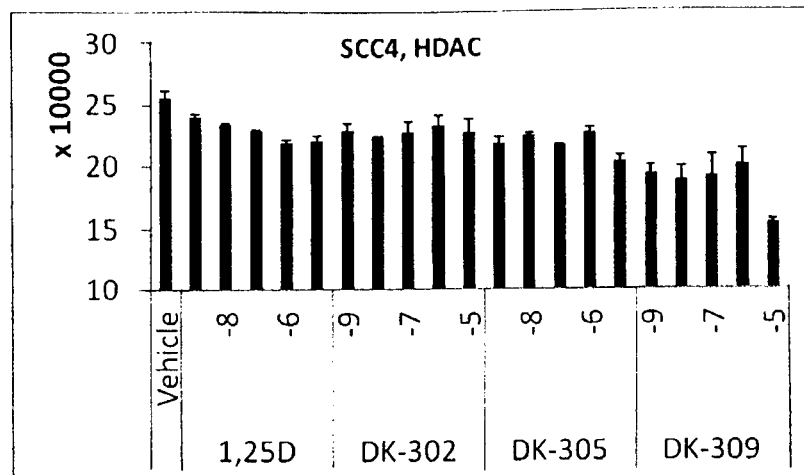
Figure 6H:
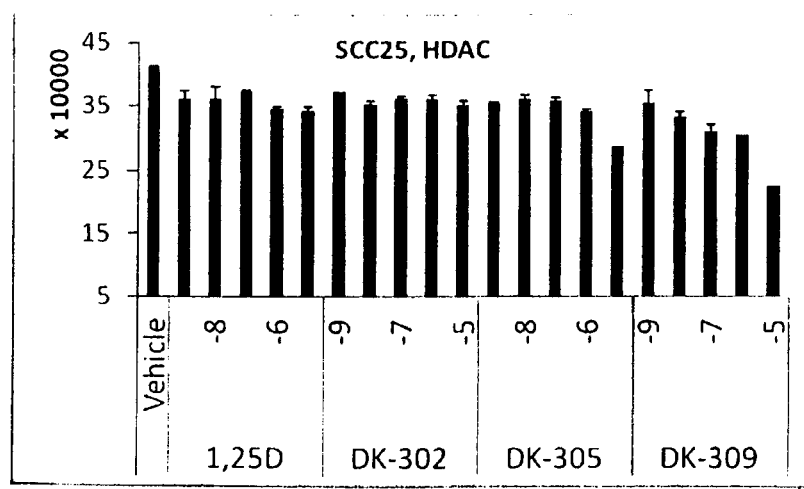

Compounds JF-B01, JF-B53, and JF-B54 were further tested for their capacity to inhibit the proliferation of 1,25D-sensitive (SCC25 and AT84) or 1,25D-resistant (SCC4) HNSCC lines. Proliferation of SCC25 or AT84 cells was strongly inhibited by 1,25D (FIGS. 2c, d), as measured by incorporation of the nucleoside analogue EdU. All test compounds blocked EdU incorporation with relative potencies that were roughly parallel to their capacity to induce CYP24 expression. Compound (2RS)-10 was 10-fold less potent than 1,25D in these assays. JF-B06 and JF-B21, which possess HDACi activity but are devoid of VDR agonism, failed to block AT84 proliferation (FIG. 2d). Remarkably, whereas SCC4 cell proliferation was resistant to 1,25D (FIG. 2e), Compounds JF-B01 and JF-B54 completely and JF-B53 partially blocked EdU incorporation. LG-190178, JF-C11 and JF-B21 all failed to block SCC4 proliferation (FIG. 2f), consistent with the efficacy of compound JF-B01 having both VDR agonist and HDACi activity. It is also noteworthy that, unlike 1,25D, compound JF-B01 and compound JF-B54 completely abolished EdU incorporation in SCC25 cells and in SCC4 cells at higher concentrations. Corresponding plates treated with the three test compounds were free of cells after 48 h of treatment, consistent with induction of cell death.

It may be possible that the compounds described herein be less potent for a primary target, however the addition of activity against a second, sympathetic biochemical target, would be expected to increase clinical efficacy by virtue of having VDR agonism/HDACi.

Compound JF-B01 was assessed by the National Cancer Institute in their 60 cell panel of human carcinoma cell lines. The results are summarized in Table 2. It displayed antiproliferative activity in all cell lines, with the most promising results in melanoma cell lines with full growth inhibition at 7 µM or less in 8 out of 9 cell lines.

TABLE 2

| Panel/Cell Line | GI50 | TGI | LC50 |
|---|---|---|---|
| Leukemia | | | |
| CCRF-CEM | 5.76E−7 | 4.80E−6 | 4.22E−5 |
| HL-60(TB) | 9.44E−7 | 2.93E−6 | 8.80E−6 |
| MOLT-4 | 1.15E−6 | 4.60E−6 | 4.09E−5 |

TABLE 2-continued

| Panel/Cell Line | GI50 | TGI | LC50 |
|---|---|---|---|
| RPMI-8226 | 1.12E−6 | 8.68E−6 | 8.25E−5 |
| SR | 1.21E−6 | 3.91E−6 | 2.49E−5 |
| Non-Small Cell Lung Cancer | | | |
| A549/A/TCC | 3.62E−6 | 1.43E−5 | 4.08E−5 |
| EKVX | 2.87E−6 | 1.24E−5 | 3.53E−5 |
| HOP-62 | 3.69E−6 | 1.47E−5 | 3.83E−5 |
| HOP-92 | 3.08E−6 | 1.53E−5 | 4.92E−5 |
| NCI-H226 | 1.98E−6 | 1.07E−5 | 3.30E−5 |
| NCI-H322M | 2.86E−6 | 1.08E−5 | 3.30E−5 |
| NCI-H460 | 1.60E−6 | 3.90E−6 | 9.51E−6 |
| NCI-H522 | 1.96E−7 | 5.18E−7 | 1.95E−5 |
| Colon Cancer | | | |
| COLO 205 | 2.33E−6 | 5.94E−6 | 2.03E−5 |
| HCC-2998 | 4.23E−6 | 1.55E−5 | 4.12E−5 |
| HCT-116 | 2.13E−6 | 1.09E−5 | 3.34E−5 |
| HCT-15 | 1.94E−6 | 1.12E−5 | 3.36E−5 |
| HT29 | 1.93E−6 | 1.00E−5 | 3.17E−5 |
| KM12 | 2.15E−6 | 8.17E−6 | 2.88E−5 |
| SW-620 | 2.30E−6 | 1.25E−5 | 3.54E−5 |
| CNS Cancer | | | |
| SF-268 | 2.26E−6 | 1.06E−5 | 3.46E−5 |
| SF-295 | 7.61E−6 | 2.02E−5 | 4.49E−5 |
| SF-539 | 1.37E−5 | 2.74E−5 | 5.49E−5 |
| SNB-19 | 2.41E−6 | 1.12E−5 | 3.35E−5 |
| SNB-75 | 4.82E−8 | 1.90E−5 | 6.20E−5 |
| U251 | 2.34E−6 | 1.23E−5 | 4.00E−5 |
| Melanoma | | | |
| LOX IMVI | 1.83E−7 | 3.32E−7 | 6.02E−7 |
| MALME-3M | 2.33E−6 | 1.07E−5 | 3.57E−5 |
| M14 | 2.30E−6 | 5.33E−6 | 1.65E−5 |
| MDA-MB-435 | 2.08E−6 | 5.20E−6 | 1.67E−5 |
| SK-MEL-2 | 1.90E−6 | 5.24E−6 | 3.00E−5 |
| SK-MEL-28 | 4.75E−6 | 1.75E−5 | 4.25E−5 |
| SK-MEL-5 | 1.39E−6 | 2.79E−6 | 5.58E−6 |
| UACC-257 | 3.34E−6 | 1.27E−5 | 3.88E−5 |
| UACC-62 | 1.68E−6 | 4.22E−6 | 1.15E−5 |
| Ovarian Cancer | | | |
| IGROV1 | 2.08E−6 | 5.25E−6 | 1.92E−5 |
| OVCAR-3 | 1.73E−6 | 5.59E−6 | 2.16E−5 |
| OVCAR-4 | 1.88E−6 | 9.44E−6 | 3.20E−5 |
| OVCAR-5 | 1.29E−5 | 2.56E−5 | 5.06E−5 |
| OVCAR-8 | 6.27E−6 | 2.03E−5 | 5.11E−5 |
| NCI/ADR-RES | 4.39E−6 | 1.67E−5 | 4.19E−5 |
| SK-OV-3 | 1.22E−5 | 2.46E−5 | 4.96E−5 |
| Renal Cancer | | | |
| 786-0 | 1.13E−5 | 2.41E−5 | 5.13E−5 |
| A498 | 4.56E−6 | 2.08E−5 | 4.56E−5 |
| ACHN | 3.20E−6 | 1.27E−5 | 3.56E−5 |
| CAKI-1 | 4.98E−6 | 1.71E−5 | 4.13E−5 |
| RXF 393 | 5.34E−6 | 1.91E−5 | 4.75E−5 |
| SN12C | 3.87E−6 | 1.59E−5 | 4.03E−5 |
| TK-10 | 2.83E−6 | 1.60E−5 | 4.28E−5 |
| UO-31 | 1.92E−6 | 6.95E−6 | 2.62E−5 |
| Prostate Cancer | | | |
| PC-3 | 3.04E−6 | 1.23E−5 | 4.18E−5 |
| DU-145 | 1.30E−5 | 2.56E−5 | 5.06E−5 |
| Breast Cancer | | | |
| MCF7 | 3.33E−7 | 2.70E−6 | 1.28E−5 |
| MDA-MB-231/ATCC | 2.18E−6 | 8.45E−6 | 3.16E−5 |
| HS 578T | 8.80E−6 | 2.65E−5 | 7.25E−5 |
| BT-549 | 2.03E−6 | 7.74E−6 | 2.85E−5 |
| T-47D | 2.21E−6 | 6.69E−6 | 2.71E−5 |
| MDA-MB-468 | 1.57E−6 | 3.53E−6 | 7.92E−6 |

Cell Proliferation

Dose-dependent effects of compounds on cell cycle progression was monitored using a CellTiter 96 Aqueous Non-Radioactive Cell Proliferation Assay Kit (Promega). The assay composed of solutions of a novel tetrazolium compound (MTS) and an electron coupling reagent (phenazine methosulfate; PMS). MTS is reduced by metabolically active cells into a soluble formazan product that absorbs at 490 nm. The quantity of formazan product absorbing at 490 nm is directly proportional to the number of living cells.

Figure 7A:
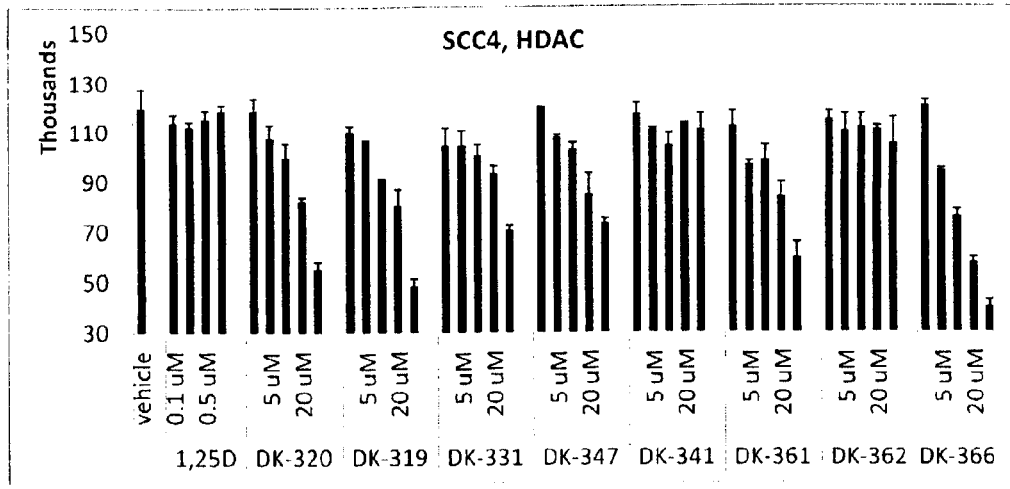
Figure 7B:
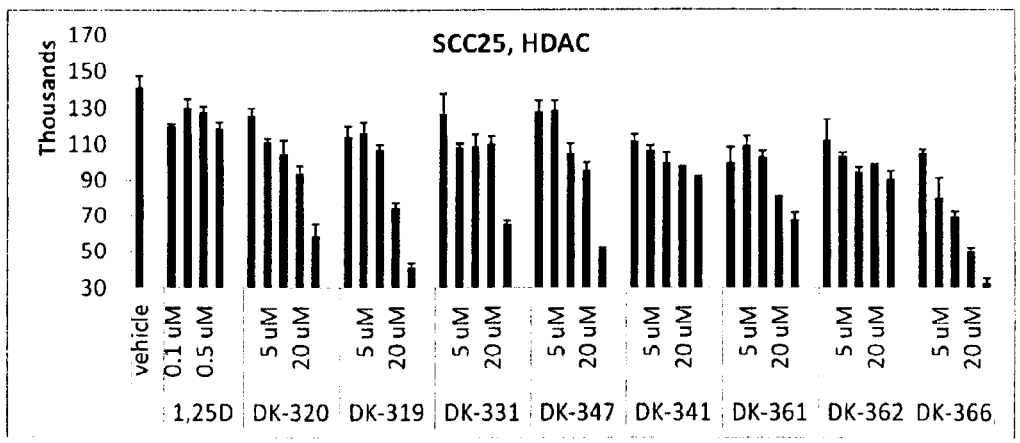
Figure 7C:
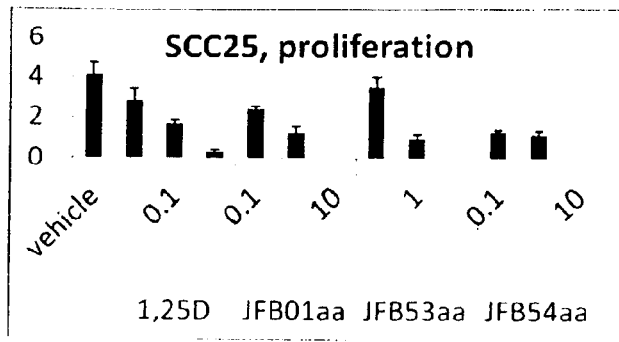
FIGS. 7*c*, 8 and 9 are showing the cell proliferation in an assay composed of solutions of a novel tetrazolium compound (MTS) and an electron coupling reagent.
Figure 8A:
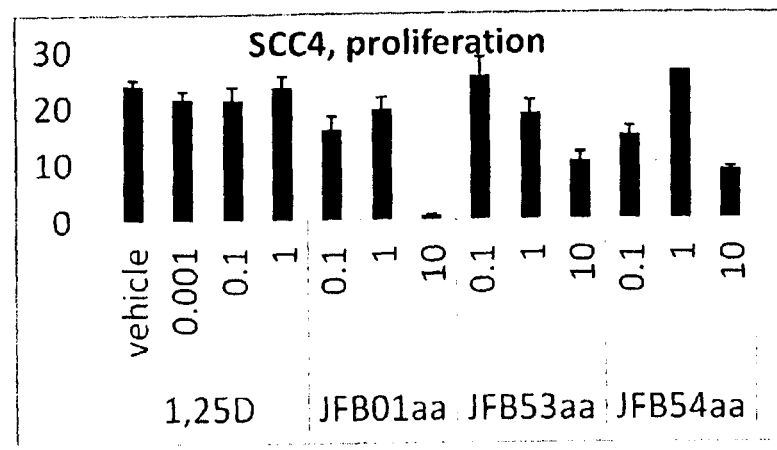
Figure 8B:
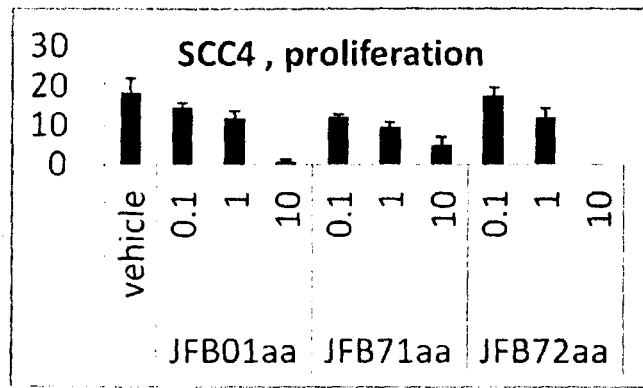
Figure 8C:
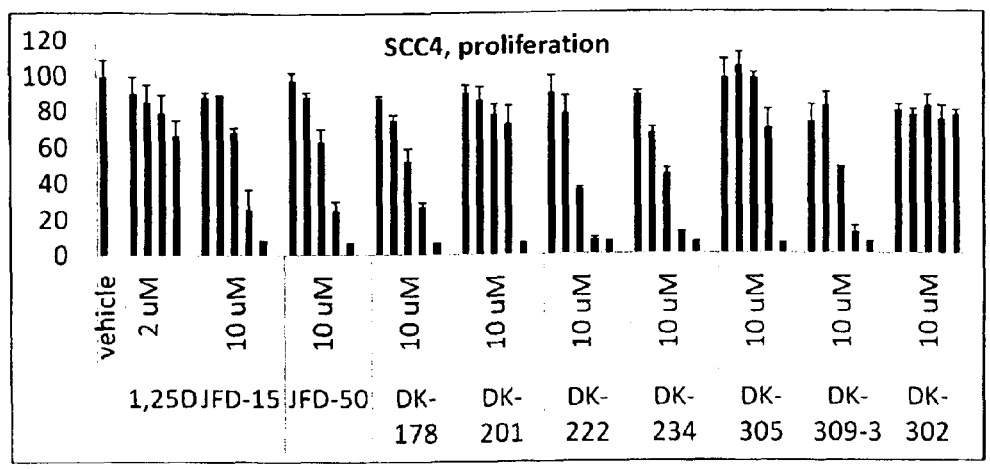
Figure 8D:
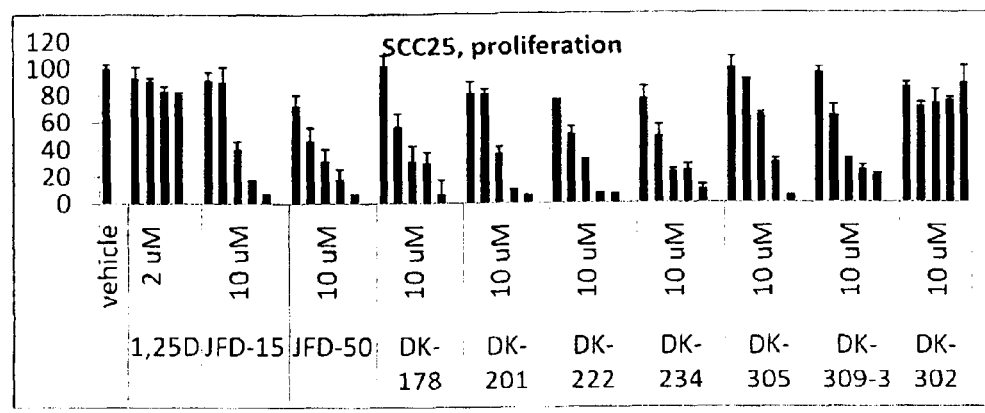
Figure 9A:
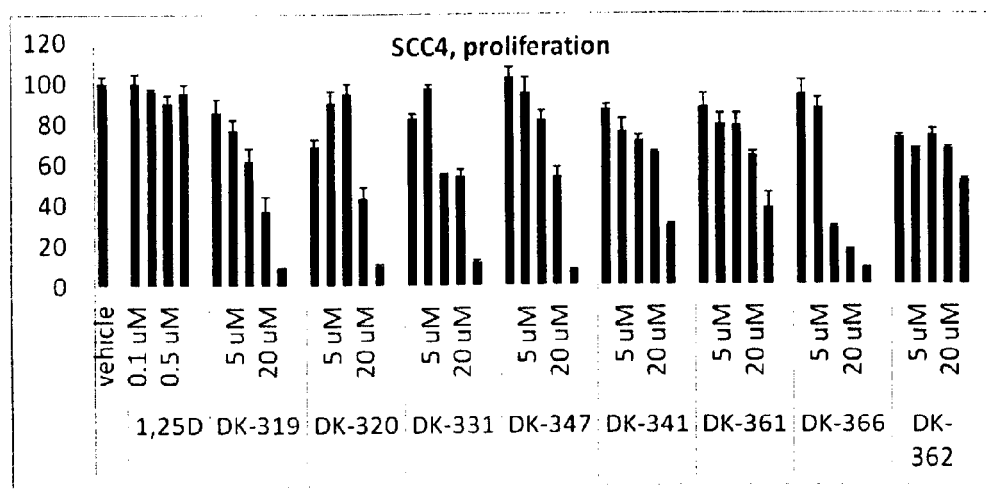
Figure 9B:
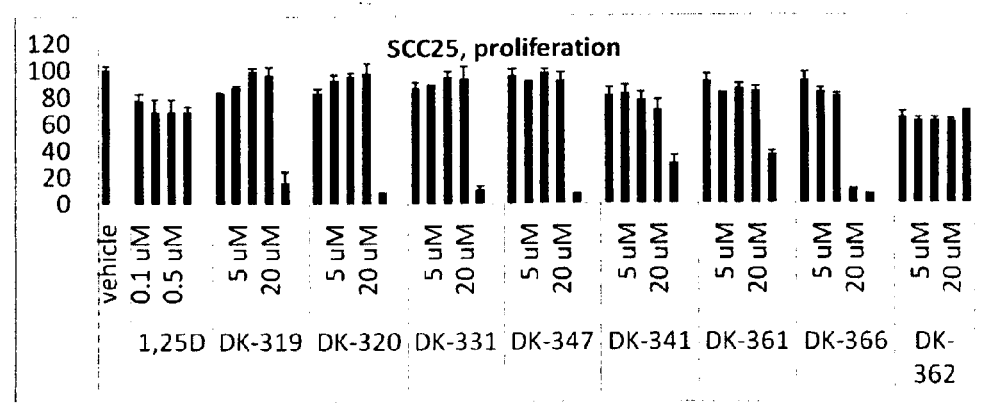
Figure 9C:
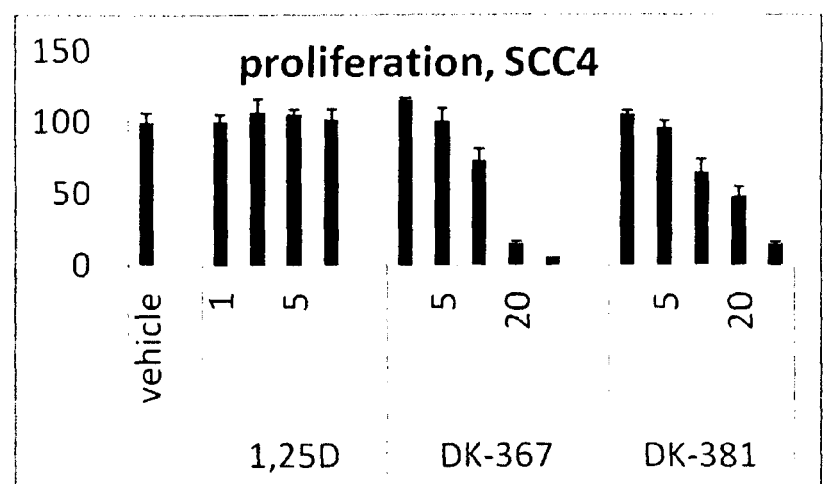
Figure 9D:
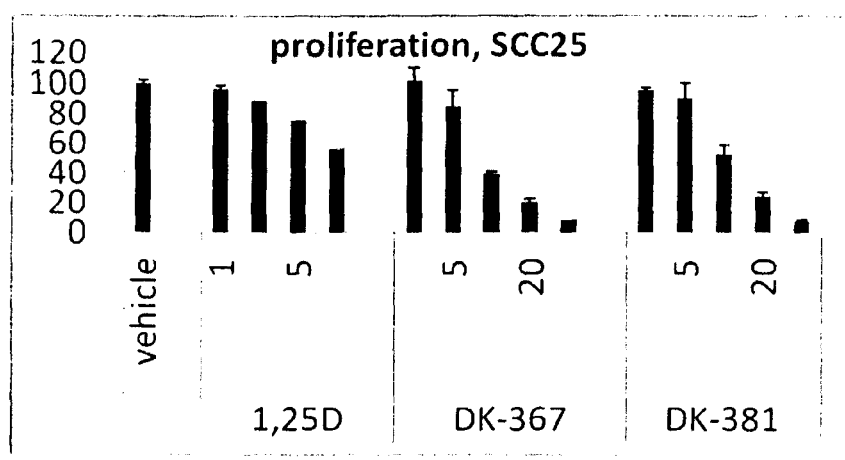

Cellular proliferation assays (FIGS. 7c, 8 and 9) showed that many compounds were active against both vitamin D responsive SCC25 and vitamin D resistant SCC4 cells. In particular, JF-B01 and its enantiomers, JF-C71 and C72, JF-D15, JF-D50, DK178, DK-222, DK-234, DK-366 and DK-367, among others, showed low micromolar potency against SCC4 cells. This antiproliferative effect again results from the combination of VDR agonism and HDACi activity of the molecules, as molecules lacking strong VDR agonism or HDACi activity (e.g. 1,25D) are ineffective. Notably, the onset of antiproliferative activity roughly coincided with the IC50s of the hybrids towards HDAC in vitro.

LDH Assay

The cytotoxic effects of compounds were screened using a Cytotoxicity Assay Kit (Cayman Chemical), which measures release of the soluble mitochondrial enzyme lactate dehydrogenase (LDH) from dying cells into the culture medium using a coupled two-step reaction. LDH in the media catalyzes the reduction of NAD+ to NADH and H+ by oxidation of lactate to pyruvate. LDH-catalyzed NADH production is then measured by following diaphorase catalyzed NADH-dependent reduction of a tetrazolium salt (INT) to highly-colored formazan which absorbs strongly at 490-520 nm.

Figure 10A:
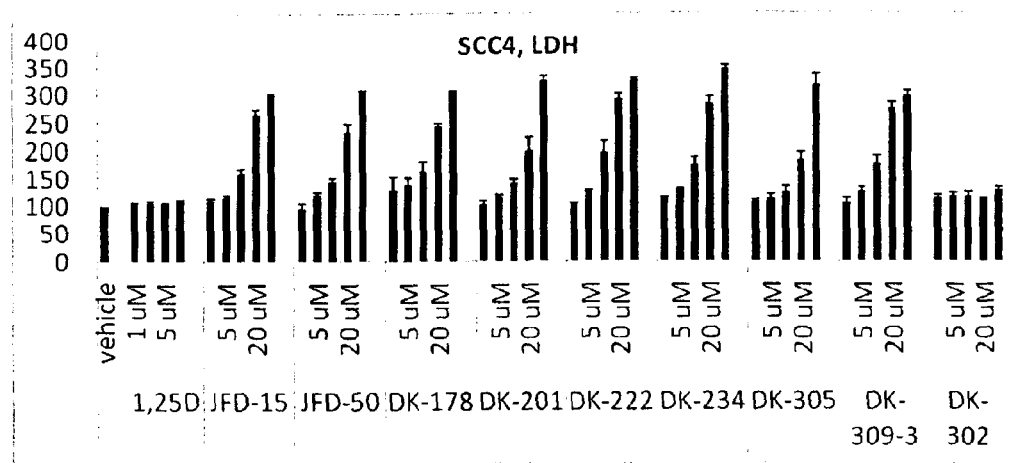
FIGS. 10 and 11 are LDH assay results which measures release of the soluble mitochondrial enzyme lactate dehydrogenase (LDH) from dying cells into the culture medium.
Figure 10B:
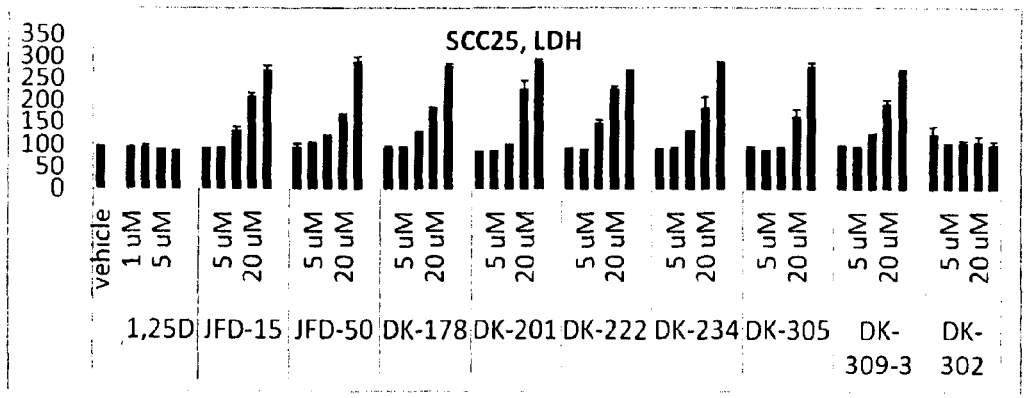
Figure 10C:
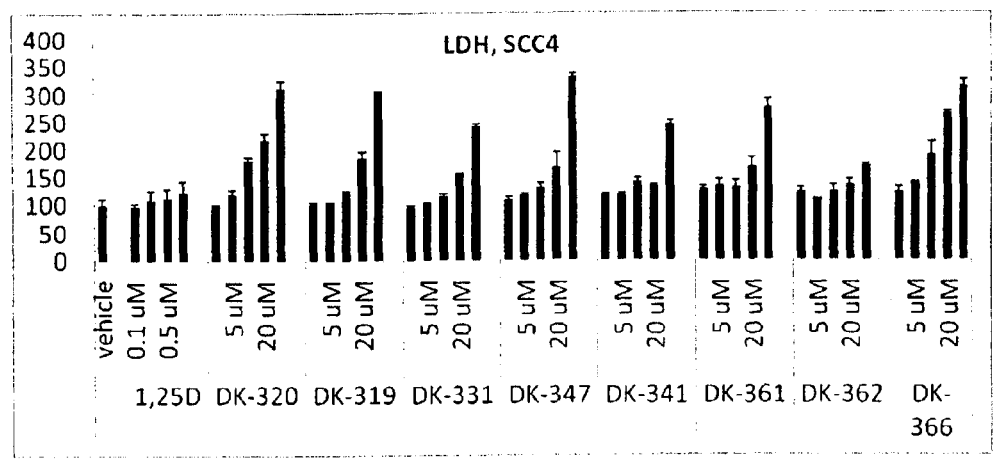
Figure 11A:
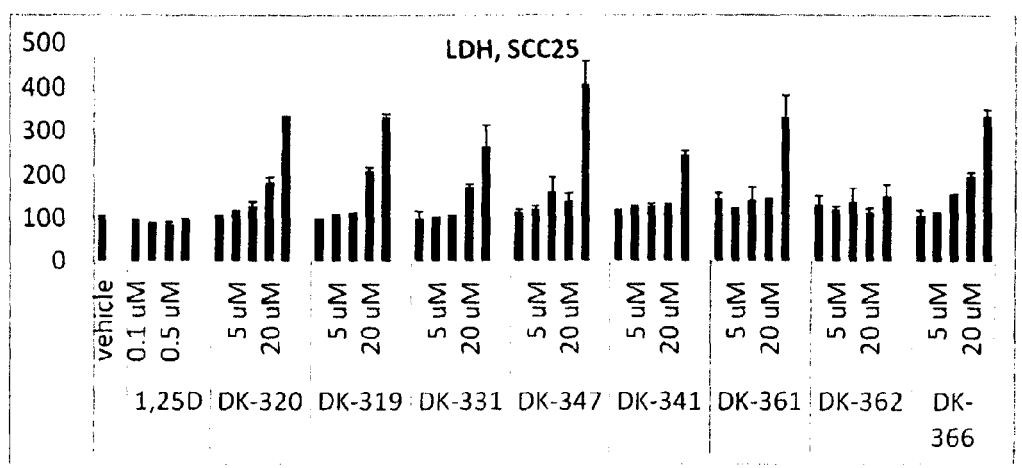
Figure 11B:
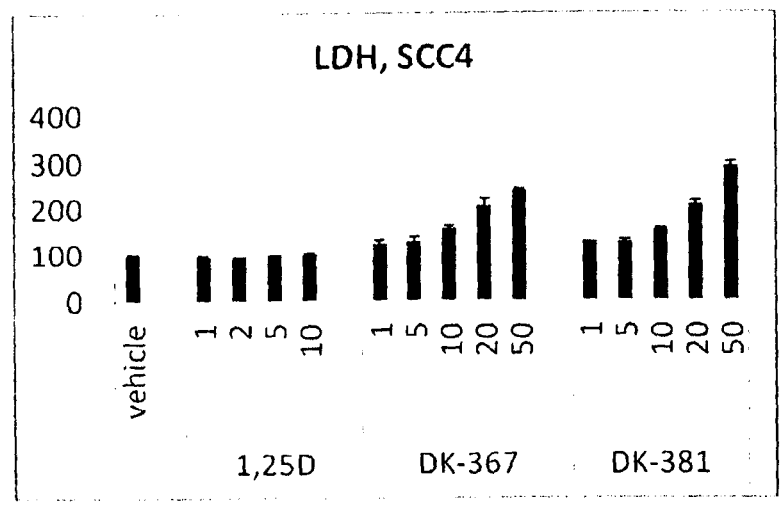
Figure 11C:
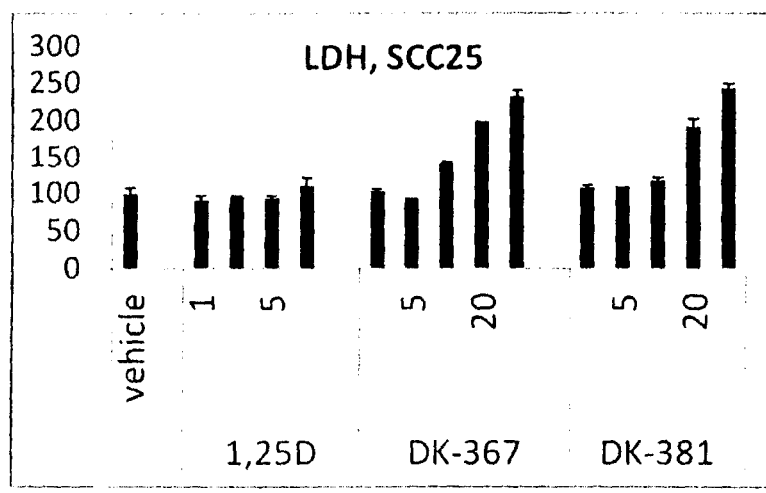

The proliferation assays above indicated the cessation of growth. The LDH assay results (FIGS. 10 and 11) showed that the compounds additionally cytotoxic to both SCC4 and SCC25 cells. The activity of compounds in this assay generally paralleled the proliferation assay; compounds which halted cell growth generally proved to be cytotoxic as well. In particular, DK-222, DK-309 and DK-366 showed good cytotoxicity against vitamin D resistant SCC4 cells.

While the invention has been described in connection with specific embodiments thereof, it is understood that it is capable of further modifications and that this application is intended to cover any variation, use, or adaptation of the invention following, in general, the principles of the invention and including such departures from the present disclosure that come within known, or customary practice within the art to which the invention pertains and as may be applied to the essential features hereinbefore set forth.

The invention claimed is:
1. A compounds of formula

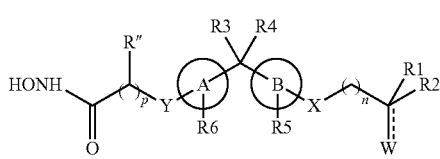

or a pharmaceutically acceptable salt thereof, wherein
the dotted line is an optional double bond;
A and B are each independently an aryl;
R1 is hydrogen, an alkyl or cycloalkyl;
R2 is absent when the dotted line is a double bond or R2 is hydrogen, an alkyl or cycloalkyl when the dotted line is absent;
W is OH when the dotted line is absent or W is O when the dotted line is a double bond;

X is O, CH$_2$, CHR7 or CR7R7, where R7 is in an alkyl or fluoroalkyl;

Y is NR10(CO), (CO)NR10, O, CH$_2$, CHR7 or CR7R7, where R7 is in an alkyl or fluoroalkyl and R10 is H or an alkyl;

R3 and R4 are each independently hydrogen, an alkyl or fluoroalkyl;

R5 and R6 are each independently an optional substituent;

when p is greater than 0, R" is H and one of said R" is optionally OH;

n and p are each an integer from 0 to 6.

2. The compound of claim 1, having the formula

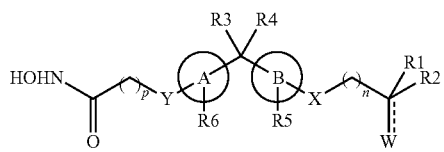

or a pharmaceutically acceptable salt thereof, wherein R1 to R6, n, p, X, Y, W, A and B are as defined in claim 1.

3. The compound of claim 1, or a pharmaceutically acceptable salt thereof, wherein X is O and Y is O or NR10(CO).

4. The compound of claim 1, or a pharmaceutically acceptable salt thereof, wherein W is OH.

5. The compound of 1, or a pharmaceutically acceptable salt thereof, wherein R1 is an alkyl or cycloalkyl and R2 is hydrogen, an alkyl or cycloalkyl.

6. The compound of claim 1, or a pharmaceutically acceptable salt thereof, wherein R3 and R4 are independently hydrogen, an alkyl.

7. A pharmaceutical composition comprising a compound or a pharmaceutically acceptable salt thereof, as defined in claim 1, and a pharmaceutically acceptable carrier.

8. The compound of claim 1 or a pharmaceutically acceptable salt thereof, having the following structure:

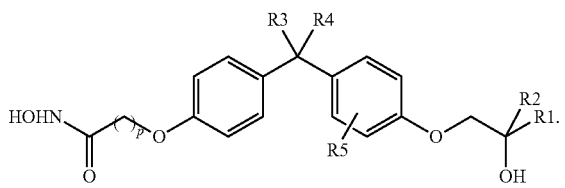

9. The compound of claim 1 or a pharmaceutically acceptable salt thereof, wherein A and B are both a phenyl.

10. The compound of claim 1 or a pharmaceutically acceptable salt thereof, wherein X and Y are both O.

11. The compound of claim 1 or a pharmaceutically acceptable salt thereof, wherein R1 is an alkyl and R2 is hydrogen.

12. The compound of claim 1 or a pharmaceutically acceptable salt thereof, wherein R3 and R4 are both a C1-4alkyl.

13. The compound of claim 1 or a pharmaceutically acceptable salt thereof, wherein when the optional substituent R5 and R6 are present, each is independently an alkyl.

14. The compound of claim 1 or a pharmaceutically acceptable salt thereof, wherein n is 1 or 2.

15. A compound selected from the following list:

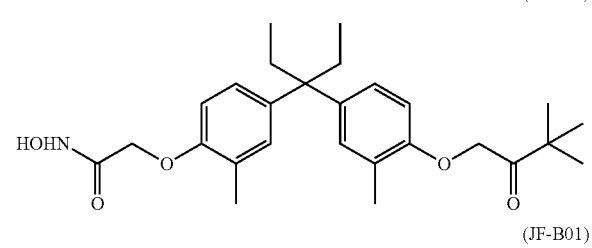
(JF-B59)

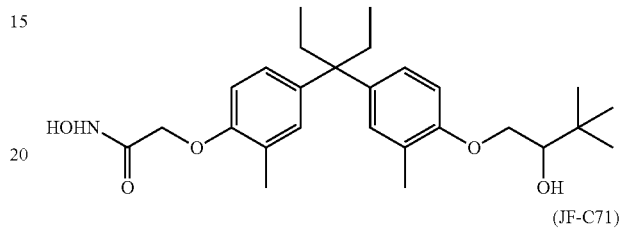
(JF-B01)

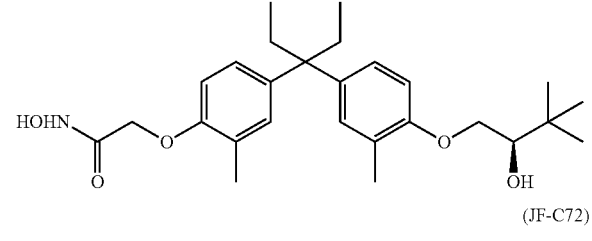
(JF-C71)

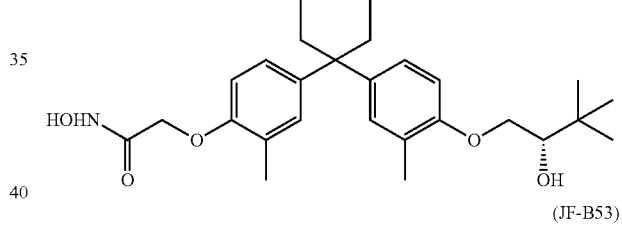
(JF-C72)

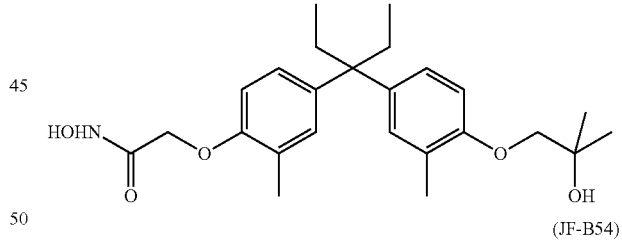
(JF-B53)

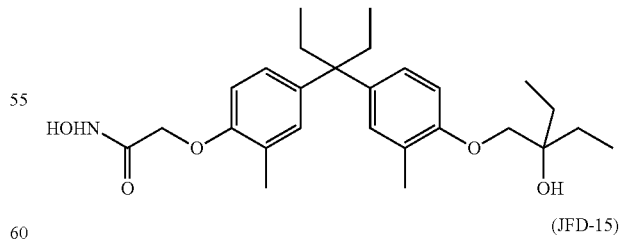
(JF-B54)

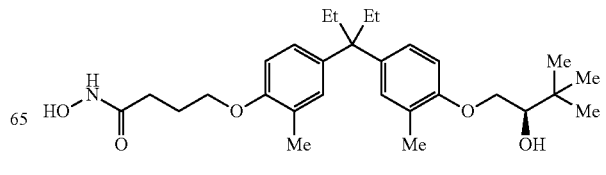
(JFD-15)

(JFD-50)
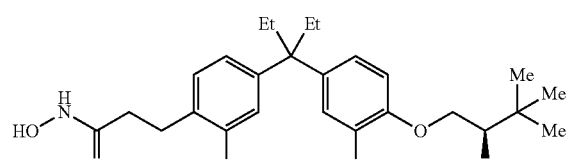

(DK-305)
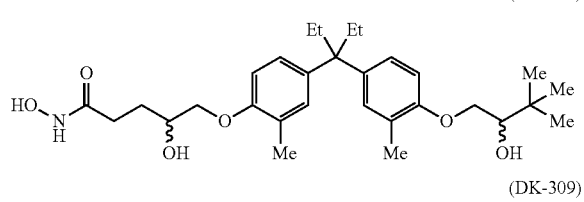

(DK-309)
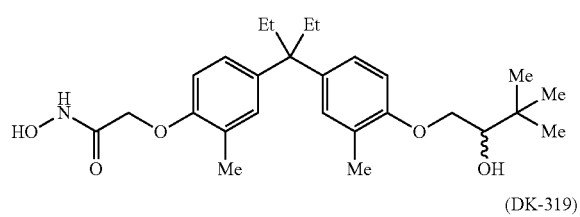

(DK-319)
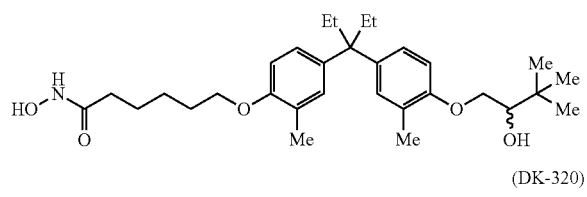

(DK-320)
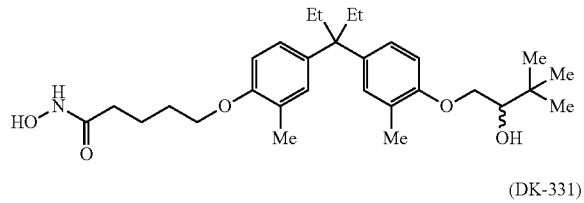

(DK-331)
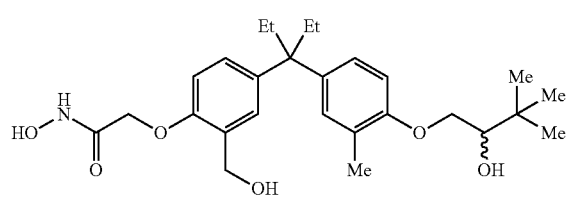

(DK-341)
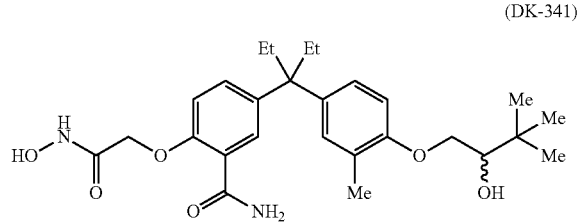

(DK-347)
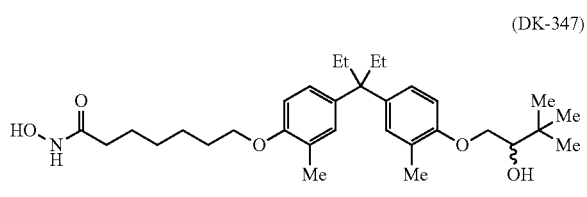

(DK-361)
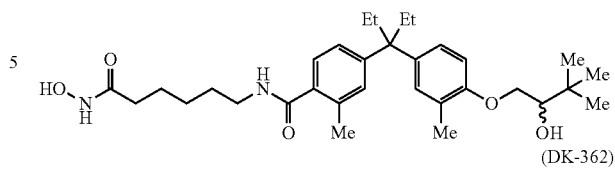

(DK-362)
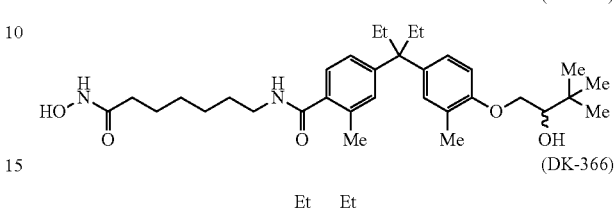

(DK-366)
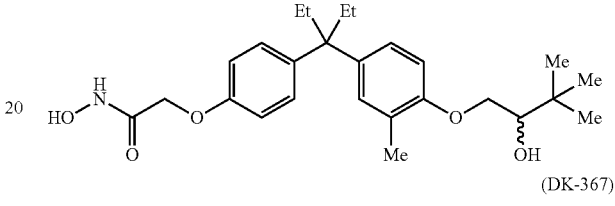

(DK-367)
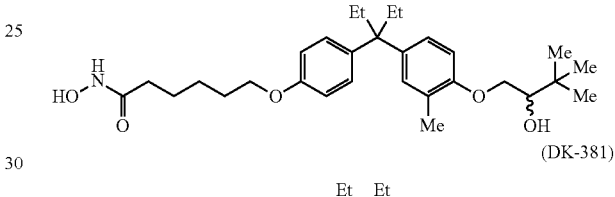

(DK-381)
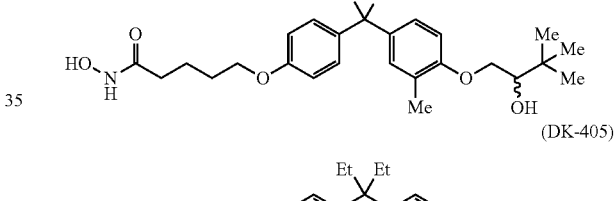

(DK-405)
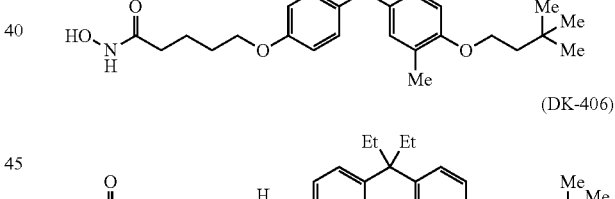

(DK-406)
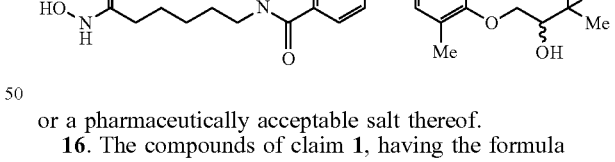

or a pharmaceutically acceptable salt thereof.

16. The compounds of claim 1, having the formula

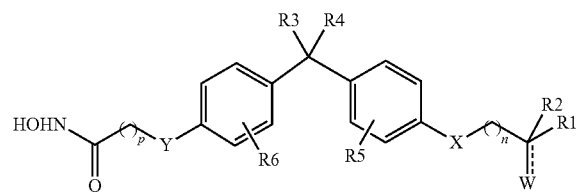

or a pharmaceutically acceptable salt thereof, wherein
the dotted line is an optional double bond;
R1 is hydrogen, or an alkyl;
R2 is absent when the dotted line is a double bond or R2 is hydrogen, or an alkyl when the dotted line is absent;
W is OH when the dotted line is absent or W is O when the dotted line is a double bond;

X is O;
Y is NR10(CO) or O where R10 is H or an alkyl;
R3 and R4 are an alkyl;
R5 is a C1-3 alkyl and R6 is H or is a C1-3 alkyl;
n and p are each an integer from 1 to 5.

17. The compounds of claim 1, having the formula

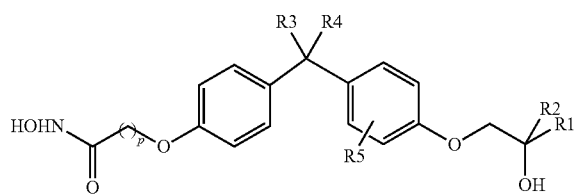

or a pharmaceutically acceptable salt thereof,
wherein R1 is alkyl, R2 is hydrogen, R3 and R4 are each independently a C1-4 alkyl; R5 is a C1-3 alkyl and p is 1-5.

18. The compounds of claim 1, having the formula

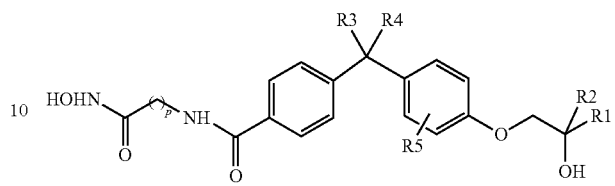

or a pharmaceutically acceptable salt thereof,
wherein R1 is alkyl, R2 is hydrogen, R3 and R4 are each independently a C1-4 alkyl; R5 is a C1-3 alkyl and p is 1-5.

* * * * *